(12) United States Patent
Panstruga et al.

(10) Patent No.: US 7,928,289 B2
(45) Date of Patent: Apr. 19, 2011

(54) METHOD FOR PRODUCTION OF TRANSGENIC PLANTS WITH INCREASED PATHOGENIC RESISTANCE BY ALTERING THE CONTENT AND/OR ACTIVITY OF ACTIN-DEPOLYMERISING FACTORS

(75) Inventors: Ralph Panstruga, Aachen (DE); Marco Miklis, Köln (DE); Paul Schulze-Lefert, Köln (DE); Markus Frank, Mannheim (DE)

(73) Assignees: BASF Plant Science GmbH, Ludwigshafen (DE); Max-Planck-Gesellschaft zür Förderung der Wissenschaften e.V., Munich (DE)

( * ) Notice: Subject to any disclaimer, the term of this patent is extended or adjusted under 35 U.S.C. 154(b) by 467 days.

(21) Appl. No.: 11/658,431

(22) PCT Filed: Jul. 14, 2005

(86) PCT No.: PCT/EP2005/007688
§ 371 (c)(1),
(2), (4) Date: Apr. 23, 2007

(87) PCT Pub. No.: WO2006/012985
PCT Pub. Date: Feb. 9, 2006

(65) Prior Publication Data
US 2008/0050825 A1 Feb. 28, 2008

(30) Foreign Application Priority Data
Jul. 28, 2004 (DE) .......................... 10 2004 036 456

(51) Int. Cl.
*C12N 15/09* (2006.01)
*C12N 15/82* (2006.01)
*C12N 15/29* (2006.01)
*A01H 5/00* (2006.01)

(52) U.S. Cl. ........ 800/279; 800/278; 800/298; 800/286; 800/287; 800/320; 800/317; 536/23.6; 435/418; 435/419; 435/468; 435/320.1

(58) Field of Classification Search .................. None
See application file for complete search history.

(56) References Cited

U.S. PATENT DOCUMENTS
6,506,559 B1 * 1/2003 Fire et al. ..................... 435/6

FOREIGN PATENT DOCUMENTS
| WO | WO-9519443 A2 | 7/1995 |
| WO | WO-03004521 A2 | 1/2003 |
| WO | WO-2004046357 A1 | 6/2004 |

OTHER PUBLICATIONS

Chuang et al. PNAS (2000) 97(9): 4985-4990.*
Wesley et al. Plant Journal (2001) 27(6), 581-590.*
Miklis, M. et al., "Actin Depolymerising Factor 3", poster presentation at "2nd International Workshop on Molecular Phytopathology" organized by the DFG-Research Group For 343 on "Mechanisms of Disease Susceptibility", Dec. 3-Dec. 5, 2003, Castle Rauischholzhausen, Germany, website http://www.uni-giessen.de/IPAZ-Workshop/workshop-2003/home.htm.
Miklis, M. et al., "Highway to Hell: The Role of the Actin-Cytoskeleton in Pathogen Defence in Barley", poster presentation in German at the conference "Molekularbiologie der Pflanzen" in Dabringhausen, Germany, Mar. 9- Mar. 12, 2004, website http://www.ruhr-uni-bochum.de/dabr2004/testposter04.htm, and in English at the conference "The International Joint Workshop on PR-Proteins and Induced Resistance" In Helsingborg, Sweden, May 5-May 9, 2004, website http://pr-ir2004.risoe.dk/index.htm.
Schmelzer, E., "Cell Polarization, A Crucial Process in Fungal Defence", Trends in Plant Science, 2002, vol. 7, No. 9, pp. 411-415.
Kobayashi, Y. et al., "Dynamic Reorganization of Microfilaments and Microtubules is Necessary for the Expression of Non-Host Resistance in Barley Coleoptile Cells", The Pant Journal, 1997, vol. 11, No. 3, pp. 525-537.
Dong, C. H. et al., "Molecular Identification and Characterization of the *Arabidopsis AtADF1, AtADF5* and *AtADF6* Genes", Plant Molecular Biology, 2001, vol. 45, pp. 517-527.
"*Arabidopsis thaliana* Actin Depolymerizing Factor 3 (ADF3) mRNA, Complete Cds.", EMBL Database Accession No. AF102821, Jan. 25, 1999.
Dong, C. H. et al., "ADF Proteins Are Involved in the Control of Flowering and Regulate F-Actin Organization, Cell Expansion, and Organ Growth in Arabidopsis", The Plant Cell, 2001, vol. 13, pp. 1333-1346.
"HB107F05_Sk.ab1 HB Hordeum vulgare cDNA Clone HB107F05_SK.ab1 Similar to (AF183903) Actin-Depolymerizing Factor 1 [Petunia x Hybrida], mRNA Sequence", EMBL Database Accession No. BM816985, Mar. 9, 2002.
Anonymous, "2nd International Workshop on Molecular Phytopathology" Organized by the DFG-Research Group for 343 on "Mechanisms of Disease Susceptibility", Dec. 3-5, 2003, Castle of Rauischholzhausen, Germany.

* cited by examiner

*Primary Examiner* — Medina A Ibrahim
(74) *Attorney, Agent, or Firm* — Connolly Bove Lodge & Hutz, LLP

(57) ABSTRACT

The invention relates to a method for production of transgenic plants and/or plant cells with increased pathogenic resistance, whereby the transgenic plants or plant cells have an altered content or an altered activity of at least one actin-depolymerising factor (ADF) with relation to the wild type. The invention also relates to the use of nucleic acids, coding for at least one ADF, for the production of transgenic plants or plant cells with increased pathogenic resistance and, furthermore, nucleic acid sequences coding for an ADF.

29 Claims, 11 Drawing Sheets

```
At1g01750        -------MANSASGMHVSDECKLKFLELKAKRNYRFIVFKIDEKAQQVMIDK------LG  47
At4g00680        -------MANSASGMHVNDECKIKFLELKAKRTYRFIYFKIDEKAQQVQIEK------LG  47
At5g52360        -------MANAASGMAVEDECKLKFLELKAKRNYRFIIFRIDG--QQVVVEK------LG  45
At4g25590        ---------------MAVEDECKLKFLELKSKRNYRFIIFRIDG--QQVVVEK------LG  38
At5g59890        -------MANAASGMAVHDDCKLRFLELKAKRTHRFIVYKIEEKQKQVIVEK------VG  47
At3g46010        -------MANAASGMAVHDDCKLRFLELKAKRTHRFIVYKIEEKQKQVVVEK------VG  47
At3g46000        -------MANAASGMAVHDDCKLKFMELKAKRTFRTIVYKIEDKQ--VIVEK------LG  45
At5g59880        -------MANAASGMAVHDDCKLKFMELKTKRTHRFIIYKIEELQKQVIVEK------IG  47
At3g45990        --------------MVLHDDCKLTFLELKERRTFRSIVYKIEDNM-QVIVEKHHYKKMHG  45
HvADF3           -------MANASSGAGIHDDCKLRFVELKSKRMHRFITYRLENQK-EVIVDQ------TG  46
At4g34970        --------------MTDDCKKSFMEMKWKKVHRYVVYKLEEKSRKVTVDK------VG  38
At2g16700        ---MAMAFKMATTGMRVTDECTSSFMDMKWKKVHRYIVFKIEEKSRKVTVDK------VG  51
At2g31200        MSFRGLSRPNAISGMGVADESKTTFLELQRKKTHRYVVFKIDESKKEVVVEK------TG  54
                                : :.  : *:..  *::::  ::  .*  : ::::         .*  :::          *

At1g01750        NPEETYEDFTRSIPEDECRYAVYDYDFTTPENCQKSKIFFIAWSPDTSRVRSKMLYASSK  107
At4g00680        NPEETYDDFTSSIPDDECRYAVYDFDFTTEDNCQKSKIFFIAWSPDTSRVRSKMLYASSK  107
At5g52360        SPQENYDDFTNYLPPNECRYAVYDFDFTTAENIQKSKIFFIAWSPDSSRVRMKMVYASSK  105
At4g25590        NPDETYDDFTASLPANECRYAVFDFDFITDENCQKSKIFFIAWSPDSSRVRMKMVYASSK   98
At5g59890        EPILTYEDFAASLPADECRYAIYDFDFVTAENCQKSKIFFIAWCPDVAKVRSKMIYASSK  107
At3g46010        QPIQTYEEFAACLPADECRYAIYDFDFVTAENCQKSKIFFIAWCPDIAKVRSKMIYASSK  107
At3g46000        EPEQSYDDFAASLPADDCRYCIYDFDFVTAENCQKSKIFFIAWSPDTAKVRDKMIYASSK  105
At5g59880        EPGQTHEDLAASLPADECRYAIFDFDFVSSEGVPRSRIFFVAWSPDTARVRSKMIYASSK  107
At3g45990        EREQSYEEFANSLPADECRYAILDIEFVPGE----RKICFIAWSPSTAKMRKKMIYSSTK  101
HvADF3           QRDATYEDFTKTLPENDCRFAVFDFDFTTPEDVPKSRIFYIFWSPDTAKVRSKMTYASN-  105
At4g34970        AAGESYDDLAASLPEDDCRYAVFDFDYVTVDNCRMSKIFFITWSPEASRIREKMMYATSK   98
At2g16700        GAGESYHDLEDSLPVDDCRYAVFDFDFVTVDNCRKSKIFFIAWSPEASKIRAKILYATSK  111
At2g31200        NPTESYDDFLASLPDNDCRYAVYDFDFVTSENCQKSKIFFFAWSPSTSGIRAKVLYSTSK  114
                  .:,::     :* ::**:.: * ::  . :.        :*  :. *.*.  :  :*  *: *::.

At1g01750        DRFKRELDGIQVELQATDPSEMSLDIIKGRVNL  140
At4g00680        DRFKREMEGIQVELQATDPSEMSLDIIKGRLNL  140
At5g52360        DRFKRELDGIQVELQATDPSEMSLDIIKSRAL-  137
At4g25590        DRFKRELDGIQVELQATDPSEMSFDIIKSRAL-  130
At5g59890        DRFKRELDGIQVELQATDPTEMDLDVLKSRVN-  139
At3g46010        DRFKRELDGIQVELQATDPTEMDLDVFRSRAN-  139
At3g46000        DRFKRELDGIQVELQATDPTEMGLDVFKSRTN-  137
At5g59880        DRFKRELDGIQVELQATDPTEMDLDVFKSRAN-  139
At3g45990        DRFKRELDGIQVEFHATDLTDISLDAIRRRIN-  133
ADF-Est          EKFKRTLDGIQIEMQATDPSEISLDVIKERAH-  137
At4g34970        SGLRRVLDGVHYELQATDPTEMGFDKIQDRAK-  130
At2g16700        DGLRRVLEGIHYELQATDPTEMGFDIIQDRAK-  143
At2g31200        DQLSRELQGIHYEIQATDPTEVDLEVLRERAN-  146
                 . : *  ::*::  *::***   :::.::  :: *
```

Figure 1

A
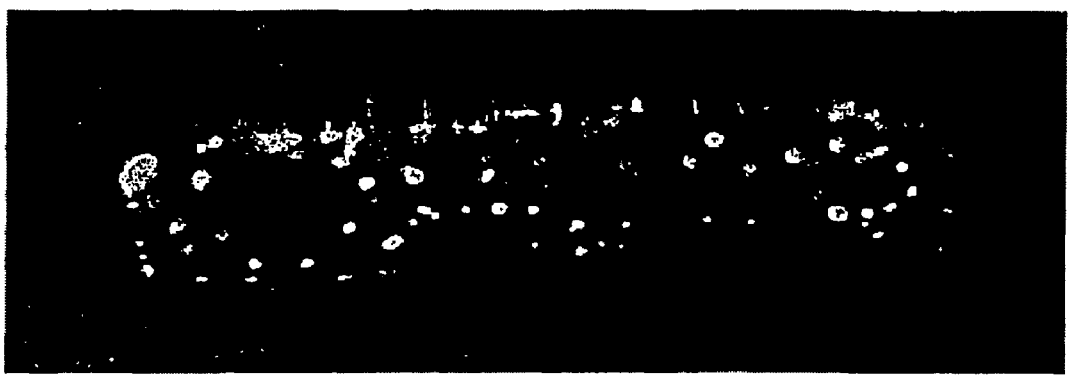
B
Figure 7

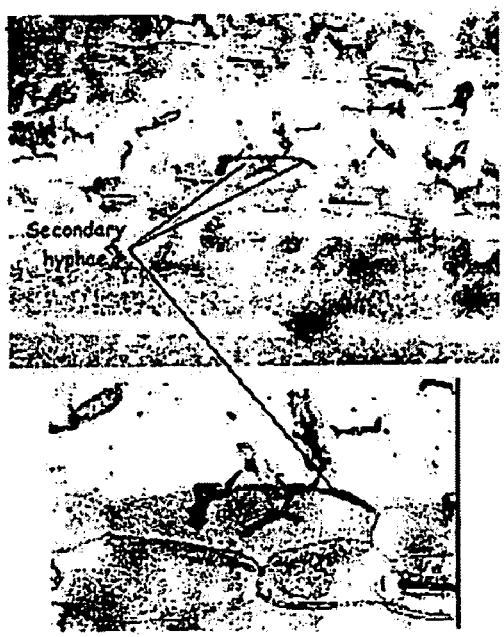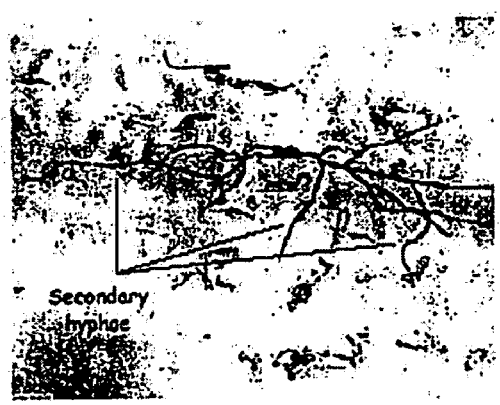
Figure 8

SEQUENCE LISTING

<160> NUMBER OF SEQ ID NOS: 101

<210> SEQ ID NO 1
<211> LENGTH: 138
<212> TYPE: PRT
<213> ORGANISM: Hordeum vulgare

<400> SEQUENCE: 1

Met Ala Asn Ala Ser Ser Gly Ala Gly Ile His Asp Asp Cys Lys Leu
1               5                   10                  15

Arg Phe Val Glu Leu Lys Ser Lys Arg Met His Arg Phe Ile Thr Tyr
            20                  25                  30

Arg Leu Glu Asn Gln Lys Glu Val Ile Val Asp Gln Thr Gly Gln Arg
        35                  40                  45

Asp Ala Thr Tyr Glu Asp Phe Thr Lys Thr Leu Pro Glu Asn Asp Cys
    50                  55                  60

Arg Phe Ala Val Phe Asp Phe Asp Phe Thr Thr Pro Glu Asp Val Pro
65                  70                  75                  80

Lys Ser Arg Ile Phe Tyr Ile Phe Trp Ser Pro Asp Thr Ala Lys Val
                85                  90                  95

Arg Ser Lys Met Thr Tyr Ala Ser Thr Asn Glu Lys Phe Lys Arg Thr
                100                 105                 110

Leu Asp Gly Ile Gln Ile Glu Met Gln Ala Thr Asp Pro Ser Glu Ile
            115                 120                 125

Ser Leu Asp Val Ile Lys Glu Arg Ala His
    130                 135

<210> SEQ ID NO 2
<211> LENGTH: 137
<212> TYPE: PRT
<213> ORGANISM: Hordeum vulgare

<400> SEQUENCE: 2

Met Ala Asn Ala Ser Ala Gly Ala Gly Ile His Asp Asp Cys Lys Leu
1               5                   10                  15

Arg Phe Val Glu Leu Lys Ser Lys Arg Met His Arg Phe Ile Thr Tyr
            20                  25                  30

Arg Leu Glu Asn Gln Lys Glu Val Ile Val Asp Gln Thr Gly Gln Arg
        35                  40                  45

Asp Ala Thr Tyr Glu Asp Phe Thr Lys Thr Leu Pro Glu Asn Asp Cys
    50                  55                  60

Arg Phe Ala Val Phe Asp Phe Asp Phe Thr Thr Pro Glu Asp Val Pro
65                  70                  75                  80

Lys Ser Arg Ile Phe Tyr Ile Phe Trp Ser Pro Asp Thr Ala Lys Val
                85                  90                  95

Arg Ser Lys Met Thr Tyr Ala Ser Asn Glu Lys Phe Lys Arg Thr Leu
                100                 105                 110

Asp Gly Ile Gln Ile Glu Met Gln Ala Thr Asp Pro Ser Glu Ile Ser
            115                 120                 125

Leu Asp Val Ile Lys Glu Arg Ala His
    130                 135

<210> SEQ ID NO 3
<211> LENGTH: 139
<212> TYPE: PRT
<213> ORGANISM: Hordeum vulgare

<400> SEQUENCE: 3

Met Ala Asn Ala Ala Ser Gly Met Ala Val Asp Asp Glu Cys Lys Leu
1               5                   10                  15

Lys Phe Leu Glu Leu Lys Ala Lys Arg Thr His Arg Phe Ile Ile Tyr
            20                  25                  30

Lys Ile Asp Asp Lys Lys Lys Met Val Val Val Glu Lys Val Gly Glu
        35                  40                  45

Pro Ala Leu Asn Tyr Glu Asp Phe Ala Ala Ser Leu Pro Thr Asn Glu

```
                    50                    55                    60
Cys Arg Tyr Ala Ile Phe Asp Tyr Asp Phe Val Thr Glu Glu Asn Cys
 65                  70                  75                  80

Gln Lys Ser Lys Ile Phe Phe Val Ala Trp Ser Pro Asp Thr Ala Arg
                 85                  90                  95

Val Arg Ser Lys Met Ile Tyr Ala Ser Ser Lys Glu Arg Phe Lys Arg
                100                 105                 110

Glu Leu Asp Gly Ile Gln Val Glu Leu Gln Ala Thr Asp Pro Thr Glu
                115                 120                 125

Val Gly Phe Asp Val Ile Gln Gly Arg Ala Asn
                130                 135

<210> SEQ ID NO 4
<211> LENGTH: 156
<212> TYPE: PRT
<213> ORGANISM: Hordeum vulgare

<400> SEQUENCE: 4

Met Ala Leu Ala Ala Ala Pro Ala Ala Leu Ala Trp Pro Ser Leu Gly
  1               5                  10                  15

Gly Asn Ser Pro Ala Trp Ile Asp Val Pro Glu Arg Ser Lys Ser Ala
                 20                  25                  30

Phe Met Glu Leu Lys Arg Arg Lys Val His Arg Tyr Val Ile Phe Lys
                 35                  40                  45

Ile Asp Asp Ser Thr Glu Glu Val Val Glu Lys Thr Gly Ser Pro
 50                  55                  60

Gly Glu Ser Tyr Asp Asp Phe Thr Ala Ser Leu Pro Val Asp Asp Cys
 65                  70                  75                  80

Arg Tyr Ala Val Tyr Asp Leu Asp Phe Val Ser Asp Asp Asn Cys Arg
                 85                  90                  95

Lys Ser Lys Ile Phe Phe Ile Ser Trp Ser Pro Asp Asp Ser Arg Ile
                100                 105                 110

Arg Ala Lys Thr Ile Tyr Ala Val Ser Arg Asn Gln Phe Arg His Glu
                115                 120                 125

Leu Asp Gly Val His Phe Glu Ile Gln Ala Thr Asp Pro Asp Asp Met
                130                 135                 140

Asp Leu Glu Val Leu Arg Val Arg Ala Asn Arg Thr
145                 150                 155

<210> SEQ ID NO 5
<211> LENGTH: 143
<212> TYPE: PRT
<213> ORGANISM: Hordeum vulgare

<400> SEQUENCE: 5

Met Ala Met Ala Tyr Lys Met Ala Thr Glu Gly Met Asn Ile Lys Glu
  1               5                  10                  15

Glu Cys Lys Arg Trp Phe Thr Glu Met Lys Trp Lys Lys Val His Arg
                 20                  25                  30

Phe Val Val Tyr Lys Ile Asp Glu Arg Thr Arg Ala Val Leu Val Asp
                 35                  40                  45

Lys Val Gly Gly Pro Gly Glu Gly Tyr Glu Glu Leu Val Ala Ala Leu
                 50                  55                  60

Pro Thr Asp Asp Cys Arg Tyr Ala Val Phe Asp Phe Asp Phe Val Ser
 65                  70                  75                  80

Val Asp Asn Cys Gln Lys Ser Lys Ile Phe Phe Ile Ala Trp Ser Pro
                 85                  90                  95
```

```
Ala Ala Ser Arg Ile Arg Ala Lys Ile Leu Tyr Ala Thr Ser Lys Gln
            100                 105                 110

Gly Leu Arg Arg Val Leu Asp Gly Val His Tyr Glu Val Gln Ala Thr
        115                 120                 125

Asp Pro Ser Glu Met Gly Phe Asp Val Ile Arg Glu Arg Ala Gln
    130                 135                 140
```

<210> SEQ ID NO 6
<211> LENGTH: 145
<212> TYPE: PRT
<213> ORGANISM: Hordeum vulgare

<400> SEQUENCE: 6

```
Met Ala Phe Met Arg Thr Ser Ser Asn Ala Ser Ser Gly Met Gly Val
1               5                   10                  15

Ala Pro Asp Ile Arg Glu Thr Phe Leu Glu Leu Gln Met Lys Lys Ala
            20                  25                  30

Phe Arg Tyr Val Ile Phe Lys Ile Glu Glu Lys Gln Lys Gln Val Val
        35                  40                  45

Val Glu Lys Thr Gly Ala Thr Thr Glu Ser Tyr Asp Asp Phe Leu Ala
50                  55                  60

Cys Leu Pro Glu Asn Asp Cys Arg Tyr Ala Leu Tyr Asp Phe Asp Phe
65                  70                  75                  80

Val Thr Gly Glu Asn Val Gln Lys Ser Lys Ile Phe Phe Ile Ala Trp
                85                  90                  95

Ser Pro Asp Thr Ser Arg Ile Arg Ala Lys Met Leu Tyr Ser Thr Ser
            100                 105                 110

Lys Asp Arg Ile Lys Gln Glu Leu Asp Gly Phe His Tyr Glu Ile Gln
        115                 120                 125

Ala Thr Asp Pro Thr Glu Val Glu Leu Asp Val Leu Arg Asp Arg Ala
    130                 135                 140

His
145
```

<210> SEQ ID NO 7
<211> LENGTH: 139
<212> TYPE: PRT
<213> ORGANISM: Hordeum vulgare

<400> SEQUENCE: 7

```
Met Ser Asn Ser Ala Ser Gly Met Ala Val Cys Asp Glu Cys Lys Leu
1               5                   10                  15

Lys Phe Gln Glu Leu Lys Ala Lys Arg Ser Phe Arg Phe Ile Val Phe
            20                  25                  30

Lys Ile Asn Glu Lys Val Gln Gln Val Val Val Asp Arg Val Gly Glu
        35                  40                  45

Lys Asn Glu Ser Tyr Asp Asp Phe Ala Ala Cys Leu Pro Ala Asp Glu
    50                  55                  60

Cys Arg Tyr Ala Val Phe Asp Phe Asp Phe Val Thr Asp Glu Asn Cys
65                  70                  75                  80

Gln Lys Ser Lys Ile Phe Phe Ile Ser Trp Ala Pro Asp Thr Ser Arg
                85                  90                  95

Val Arg Ser Lys Met Leu Tyr Ala Ser Ser Lys Asp Arg Phe Lys Arg
            100                 105                 110

Glu Leu Asp Gly Ile Gln Val Glu Leu Gln Ala Thr Asp Pro Ser Glu
        115                 120                 125
```

```
Met Ser Met Asp Ile Val Lys Ala Arg Ala Leu
    130                 135
```

<210> SEQ ID NO 8
<211> LENGTH: 168
<212> TYPE: PRT
<213> ORGANISM: Hordeum vulgare

<400> SEQUENCE: 8

```
Met Ala Asn Ser Ala Ser Gly Met Ala Val Ser Asp Glu Cys Lys Leu
1               5                   10                  15

Lys Phe Gln Asp Leu Lys Ala Lys Arg Ser Phe Arg Phe Ile Thr Phe
            20                  25                  30

Lys Ile Asn Glu Asn Thr Gln Gln Val Val Asp Arg Val Gly Gln
        35                  40                  45

Pro Gly Asp Thr Tyr Ala Asp Phe Thr Ala Ser Met Pro Ala Asp Glu
    50                  55                  60

Cys Arg Tyr Ala Val Phe Asp Phe Asp Phe Val Thr Asp Glu Asn Cys
65                  70                  75                  80

Gln Lys Ser Lys Ile Phe Phe Ile Ser Trp Ser Pro Asp Ser Ser Arg
                85                  90                  95

Val Arg Ser Lys Met Leu Tyr Ala Ser Ser Lys Asp Arg Phe Lys Arg
            100                 105                 110

Glu Leu Asp Gly Ile Gln Val Glu Leu Gln Ala Thr Glu Pro Ser Glu
        115                 120                 125

Met Ser Met Gly His Arg Gln Gly Gln Ser Pro Leu Lys Gln Ser Leu
    130                 135                 140

Val Ala Pro Ser Ile Pro Asp Ser Lys Ala Ser Ser Trp Ile His Tyr
145                 150                 155                 160

Thr Ala Cys Ala Cys Pro Thr Tyr
                165
```

<210> SEQ ID NO 9
<211> LENGTH: 139
<212> TYPE: PRT
<213> ORGANISM: Arabidopsis thaliana

<400> SEQUENCE: 9

```
Met Ala Asn Ala Ala Ser Gly Met Ala Val His Asp Asp Cys Lys Leu
1               5                   10                  15

Arg Phe Leu Glu Leu Lys Ala Lys Arg Thr His Arg Phe Ile Val Tyr
            20                  25                  30

Lys Ile Glu Glu Lys Gln Lys Gln Val Val Glu Lys Val Gly Gln
        35                  40                  45

Pro Ile Gln Thr Tyr Glu Glu Phe Ala Ala Cys Leu Pro Ala Asp Glu
    50                  55                  60

Cys Arg Tyr Ala Ile Tyr Asp Phe Asp Phe Val Thr Ala Glu Asn Cys
65                  70                  75                  80

Gln Lys Ser Lys Ile Phe Phe Ile Ala Trp Cys Pro Asp Ile Ala Lys
                85                  90                  95

Val Arg Ser Lys Met Ile Tyr Ala Ser Ser Lys Asp Arg Phe Lys Arg
            100                 105                 110

Glu Leu Asp Gly Ile Gln Val Glu Leu Gln Ala Thr Pro Pro Thr Glu
        115                 120                 125

Met Asp Leu Asp Val Phe Arg Ser Arg Ala Asn
    130                 135
```

```
<210> SEQ ID NO 10
<211> LENGTH: 137
<212> TYPE: PRT
<213> ORGANISM: Arabidopsis thaliana

<400> SEQUENCE: 10

Met Ala Asn Ala Ala Ser Gly Met Ala Val His Asp Asp Cys Lys Leu
1               5                   10                  15

Lys Phe Met Glu Leu Lys Ala Lys Arg Thr Phe Arg Thr Ile Val Tyr
            20                  25                  30

Lys Ile Glu Asp Lys Gln Val Ile Val Glu Lys Leu Gly Glu Pro Glu
        35                  40                  45

Gln Ser Tyr Asp Asp Phe Ala Ala Ser Leu Pro Ala Asp Asp Cys Arg
    50                  55                  60

Tyr Cys Ile Tyr Asp Phe Asp Phe Val Thr Ala Glu Asn Cys Gln Lys
65                  70                  75                  80

Ser Lys Ile Phe Phe Ile Ala Trp Ser Pro Asp Thr Ala Lys Val Arg
                85                  90                  95

Asp Lys Met Ile Tyr Ala Ser Ser Lys Asp Arg Phe Lys Arg Glu Leu
            100                 105                 110

Asp Gly Ile Gln Val Glu Leu Gln Ala Thr Asp Pro Thr Glu Met Gly
        115                 120                 125

Leu Asp Val Phe Lys Ser Arg Thr Asn
    130                 135

<210> SEQ ID NO 11
<211> LENGTH: 139
<212> TYPE: PRT
<213> ORGANISM: Arabidopsis thaliana

<400> SEQUENCE: 11

Met Ala Asn Ala Ala Ser Gly Met Ala Val His Asp Asp Cys Lys Leu
1               5                   10                  15

Lys Phe Met Glu Leu Lys Thr Lys Arg Thr His Arg Phe Ile Ile Tyr
            20                  25                  30

Lys Ile Glu Glu Leu Gln Lys Gln Val Ile Val Glu Lys Ile Gly Glu
        35                  40                  45

Pro Gly Gln Thr His Glu Asp Leu Ala Ala Ser Leu Pro Ala Asp Glu
    50                  55                  60

Cys Arg Tyr Ala Ile Phe Asp Phe Asp Phe Val Ser Ser Glu Gly Val
65                  70                  75                  80

Pro Arg Ser Arg Ile Phe Phe Val Ala Trp Ser Pro Asp Thr Ala Arg
                85                  90                  95

Val Arg Ser Lys Met Ile Tyr Ala Ser Ser Lys Asp Arg Phe Lys Arg
            100                 105                 110

Glu Leu Asp Gly Ile Gln Val Glu Leu Gln Ala Thr Asp Pro Thr Glu
        115                 120                 125

Met Asp Leu Asp Val Phe Lys Ser Arg Ala Asn
    130                 135

<210> SEQ ID NO 12
<211> LENGTH: 139
<212> TYPE: PRT
<213> ORGANISM: Arabidopsis thaliana

<400> SEQUENCE: 12

Met Ala Asn Ala Ala Ser Gly Met Ala Val His Asp Asp Cys Lys Leu
1               5                   10                  15
```

-continued

```
Arg Phe Leu Glu Leu Lys Ala Lys Arg Thr His Arg Phe Ile Val Tyr
            20                  25                  30
Lys Ile Glu Glu Lys Gln Lys Gln Val Ile Val Glu Lys Val Gly Glu
        35                  40                  45
Pro Ile Leu Thr Tyr Glu Asp Phe Ala Ala Ser Leu Pro Ala Asp Glu
    50                  55                  60
Cys Arg Tyr Ala Ile Tyr Asp Phe Asp Phe Val Thr Ala Glu Asn Cys
65                  70                  75                  80
Gln Lys Ser Lys Ile Phe Phe Ile Ala Trp Cys Pro Asp Val Ala Lys
                85                  90                  95
Val Arg Ser Lys Met Ile Tyr Ala Ser Ser Lys Asp Arg Phe Lys Arg
            100                 105                 110
Glu Leu Asp Gly Ile Gln Val Glu Leu Gln Ala Thr Asp Pro Thr Glu
        115                 120                 125
Met Asp Leu Asp Val Leu Lys Ser Arg Val Asn
    130                 135

<210> SEQ ID NO 13
<211> LENGTH: 143
<212> TYPE: PRT
<213> ORGANISM: Arabidopsis thaliana

<400> SEQUENCE: 13

Met Ala Met Ala Phe Lys Met Ala Thr Thr Gly Met Arg Val Thr Asp
1               5                   10                  15
Glu Cys Thr Ser Ser Phe Met Asp Met Lys Trp Lys Lys Val His Arg
            20                  25                  30
Tyr Ile Val Phe Lys Ile Glu Glu Lys Ser Arg Lys Val Thr Val Asp
        35                  40                  45
Lys Val Gly Gly Ala Gly Glu Ser Tyr His Asp Leu Glu Asp Ser Leu
    50                  55                  60
Pro Val Asp Asp Cys Arg Tyr Ala Val Phe Asp Phe Asp Phe Val Thr
65                  70                  75                  80
Val Asp Asn Cys Arg Lys Ser Lys Ile Phe Phe Ile Ala Trp Ser Pro
                85                  90                  95
Glu Ala Ser Lys Ile Arg Ala Lys Ile Leu Tyr Ala Thr Ser Lys Asp
            100                 105                 110
Gly Leu Arg Arg Val Leu Glu Gly Ile His Tyr Glu Leu Gln Ala Thr
        115                 120                 125
Asp Pro Thr Glu Met Gly Phe Asp Ile Ile Gln Asp Arg Ala Lys
    130                 135                 140

<210> SEQ ID NO 14
<211> LENGTH: 146
<212> TYPE: PRT
<213> ORGANISM: Arabidopsis thaliana

<400> SEQUENCE: 14

Met Ser Phe Arg Gly Leu Ser Arg Pro Asn Ala Ile Ser Gly Met Gly
1               5                   10                  15
Val Ala Asp Glu Ser Lys Thr Thr Phe Leu Glu Leu Gln Arg Lys Lys
            20                  25                  30
Thr His Arg Tyr Val Val Phe Lys Ile Asp Glu Ser Lys Lys Glu Val
        35                  40                  45
Val Val Glu Lys Thr Gly Asn Pro Thr Glu Ser Tyr Asp Asp Phe Leu
    50                  55                  60
Ala Ser Leu Pro Asp Asn Asp Cys Arg Tyr Ala Val Tyr Asp Phe Asp
```

```
                65                  70                  75                  80
Phe Val Thr Ser Glu Asn Cys Gln Lys Ser Lys Ile Phe Phe Ala
                    85                  90                  95

Trp Ser Pro Ser Thr Ser Gly Ile Arg Ala Lys Val Leu Tyr Ser Thr
                100                 105                 110

Ser Lys Asp Gln Leu Ser Arg Glu Leu Gln Gly Ile His Tyr Glu Ile
            115                 120                 125

Gln Ala Thr Asp Pro Thr Glu Val Asp Leu Glu Val Leu Arg Glu Arg
        130                 135                 140

Ala Asn
145
```

<210> SEQ ID NO 15
<211> LENGTH: 137
<212> TYPE: PRT
<213> ORGANISM: Arabidopsis thaliana

<400> SEQUENCE: 15

```
Met Ala Asn Ala Ala Ser Gly Met Ala Val Glu Asp Glu Cys Lys Leu
1               5                   10                  15

Lys Phe Leu Glu Leu Lys Ala Lys Arg Asn Tyr Arg Phe Ile Ile Phe
                20                  25                  30

Arg Ile Asp Gly Gln Gln Val Val Val Glu Lys Leu Gly Ser Pro Gln
            35                  40                  45

Glu Asn Tyr Asp Asp Phe Thr Asn Tyr Leu Pro Pro Asn Glu Cys Arg
        50                  55                  60

Tyr Ala Val Tyr Asp Phe Asp Phe Thr Thr Ala Glu Asn Ile Gln Lys
65                  70                  75                  80

Ser Lys Ile Phe Phe Ile Ala Trp Ser Pro Asp Ser Ser Arg Val Arg
                85                  90                  95

Met Lys Met Val Tyr Ala Ser Ser Lys Asp Arg Phe Lys Arg Glu Leu
                100                 105                 110

Asp Gly Ile Gln Val Glu Leu Gln Ala Thr Asp Pro Ser Glu Met Ser
            115                 120                 125

Leu Asp Ile Ile Lys Ser Arg Ala Leu
        130                 135
```

<210> SEQ ID NO 16
<211> LENGTH: 140
<212> TYPE: PRT
<213> ORGANISM: Arabidopsis thaliana

<400> SEQUENCE: 16

```
Met Ala Asn Ser Ala Ser Gly Met His Val Asn Asp Glu Cys Lys Ile
1               5                   10                  15

Lys Phe Leu Glu Leu Lys Ala Lys Arg Thr Tyr Arg Phe Ile Val Phe
                20                  25                  30

Lys Ile Asp Glu Lys Ala Gln Gln Val Gln Ile Glu Lys Leu Gly Asn
            35                  40                  45

Pro Glu Glu Thr Tyr Asp Phe Thr Ser Ser Ile Pro Asp Asp Glu
        50                  55                  60

Cys Arg Tyr Ala Val Tyr Asp Phe Asp Phe Thr Thr Glu Asp Asn Cys
65                  70                  75                  80

Gln Lys Ser Lys Ile Phe Phe Ile Ala Trp Ser Pro Asp Thr Ser Arg
                85                  90                  95

Val Arg Ser Lys Met Leu Tyr Ala Ser Ser Lys Asp Arg Phe Lys Arg
                100                 105                 110
```

```
<210> SEQ ID NO 17
<211> LENGTH: 130
<212> TYPE: PRT
<213> ORGANISM: Arabidopsis thaliana

<400> SEQUENCE: 17

Met Thr Asp Asp Cys Lys Lys Ser Phe Met Glu Met Lys Trp Lys Lys
1               5                   10                  15

Val His Arg Tyr Val Val Tyr Lys Leu Glu Glu Lys Ser Arg Lys Val
                20                  25                  30

Thr Val Asp Lys Val Gly Ala Ala Gly Glu Ser Tyr Asp Asp Leu Ala
            35                  40                  45

Ala Ser Leu Pro Glu Asp Asp Cys Arg Tyr Ala Val Phe Asp Phe Asp
    50                  55                  60

Tyr Val Thr Val Asp Asn Cys Arg Met Ser Lys Ile Phe Phe Ile Thr
65                  70                  75                  80

Trp Ser Pro Glu Ala Ser Arg Ile Arg Glu Lys Met Met Tyr Ala Thr
                85                  90                  95

Ser Lys Ser Gly Leu Arg Arg Val Leu Asp Gly Val His Tyr Glu Leu
                100                 105                 110

Gln Ala Thr Asp Pro Thr Glu Met Gly Phe Asp Lys Ile Gln Asp Arg
            115                 120                 125

Ala Lys
    130

<210> SEQ ID NO 18
<211> LENGTH: 140
<212> TYPE: PRT
<213> ORGANISM: Arabidopsis thaliana

<400> SEQUENCE: 18

Met Ala Asn Ser Ala Ser Gly Met His Val Ser Asp Glu Cys Lys Leu
1               5                   10                  15

Lys Phe Leu Glu Leu Lys Ala Lys Arg Asn Tyr Arg Phe Ile Val Phe
                20                  25                  30

Lys Ile Asp Glu Lys Ala Gln Gln Val Met Ile Asp Lys Leu Gly Asn
            35                  40                  45

Pro Glu Glu Thr Tyr Glu Asp Phe Thr Arg Ser Ile Pro Glu Asp Glu
    50                  55                  60

Cys Arg Tyr Ala Val Tyr Asp Tyr Asp Phe Thr Thr Pro Glu Asn Cys
65                  70                  75                  80

Gln Lys Ser Lys Ile Phe Phe Ile Ala Trp Ser Pro Asp Thr Ser Arg
                85                  90                  95

Val Arg Ser Lys Met Leu Tyr Ala Ser Ser Lys Asp Arg Phe Lys Arg
                100                 105                 110

Glu Leu Asp Gly Ile Gln Val Glu Leu Gln Ala Thr Asp Pro Ser Glu
            115                 120                 125

Met Ser Leu Asp Ile Ile Lys Gly Arg Val Asn Leu
    130                 135                 140

<210> SEQ ID NO 19
<211> LENGTH: 130
```

<212> TYPE: PRT
<213> ORGANISM: Arabidopsis thaliana

<400> SEQUENCE: 19

Met Ala Val Glu Asp Glu Cys Lys Leu Lys Phe Leu Glu Leu Lys Ser
1               5                   10                  15

Lys Arg Asn Tyr Arg Phe Ile Ile Phe Arg Ile Asp Gly Gln Gln Val
            20                  25                  30

Val Val Glu Lys Leu Gly Asn Pro Asp Glu Thr Tyr Asp Asp Phe Thr
        35                  40                  45

Ala Ser Leu Pro Ala Asn Glu Cys Arg Tyr Ala Val Phe Asp Phe Asp
    50                  55                  60

Phe Ile Thr Asp Glu Asn Cys Gln Lys Ser Lys Ile Phe Phe Ile Ala
65                  70                  75                  80

Trp Ser Pro Asp Ser Ser Arg Val Arg Met Lys Met Val Tyr Ala Ser
                85                  90                  95

Ser Lys Asp Arg Phe Lys Arg Glu Leu Asp Gly Ile Gln Val Glu Leu
            100                 105                 110

Gln Ala Thr Asp Pro Ser Glu Met Ser Phe Asp Ile Ile Lys Ser Arg
        115                 120                 125

Ala Leu
    130

<210> SEQ ID NO 20
<211> LENGTH: 133
<212> TYPE: PRT
<213> ORGANISM: Arabidopsis thaliana

<400> SEQUENCE: 20

Met Val Leu His Asp Asp Cys Lys Leu Thr Phe Leu Glu Leu Lys Glu
1               5                   10                  15

Arg Arg Thr Phe Arg Ser Ile Val Tyr Lys Ile Glu Asp Asn Met Gln
            20                  25                  30

Val Ile Val Glu Lys His His Tyr Lys Lys Met His Gly Glu Arg Glu
        35                  40                  45

Gln Ser Tyr Glu Glu Phe Ala Asn Ser Leu Pro Ala Asp Glu Cys Arg
    50                  55                  60

Tyr Ala Ile Leu Asp Ile Glu Phe Val Pro Gly Glu Arg Lys Ile Cys
65                  70                  75                  80

Phe Ile Ala Trp Ser Pro Ser Thr Ala Lys Met Arg Lys Lys Met Ile
                85                  90                  95

Tyr Ser Ser Thr Lys Asp Arg Phe Lys Arg Glu Leu Asp Gly Ile Gln
            100                 105                 110

Val Glu Phe His Ala Thr Asp Leu Thr Asp Ile Ser Leu Asp Ala Ile
        115                 120                 125

Arg Arg Arg Ile Asn
    130

<210> SEQ ID NO 21
<211> LENGTH: 139
<212> TYPE: PRT
<213> ORGANISM: Oryza sativa

<400> SEQUENCE: 21

Met Ala Asn Ala Ala Ser Gly Met Ala Val Asp Asp Glu Cys Lys Leu
1               5                   10                  15

Lys Phe Leu Glu Leu Lys Ala Lys Arg Thr Tyr Arg Phe Ile Ile Tyr
            20                  25                  30

```
Lys Ile Asp Glu Lys Lys Lys Met Val Val Glu Lys Val Gly Glu
         35                  40                  45

Pro Val Leu Asn Tyr Asp Asp Phe Ala Ala Ser Leu Pro Ala Asn Glu
 50                  55                  60

Cys Arg Tyr Ala Ile Phe Asp Tyr Asp Phe Val Thr Glu Glu Asn Cys
 65                  70                  75                  80

Gln Lys Ser Lys Ile Phe Phe Ile Ala Trp Ser Pro Asp Thr Ser Arg
                 85                  90                  95

Val Arg Ser Lys Met Ile Tyr Ala Ser Ser Lys Asp Arg Phe Lys Arg
                100                 105                 110

Glu Leu Asp Gly Ile Gln Val Glu Leu Gln Ala Thr Asp Pro Thr Glu
            115                 120                 125

Val Gly Leu Asp Val Ile Arg Gly Arg Ala Asn
        130                 135

<210> SEQ ID NO 22
<211> LENGTH: 153
<212> TYPE: PRT
<213> ORGANISM: Oryza sativa

<400> SEQUENCE: 22

Met Val Ala Ala Ala Ala Val Leu Pro Trp Gly Gly Gly Ser
 1               5                  10                  15

Pro Ala Trp Ile Glu Val Pro Glu Lys Ser Lys Ser Ala Phe Trp Glu
                 20                  25                  30

Leu Lys Arg Arg Lys Val His Arg Tyr Val Ile Phe Lys Ile Asp Asp
             35                  40                  45

Arg Arg Glu Glu Ile Val Val Glu Lys Thr Gly Ala Pro Gly Glu Ser
 50                  55                  60

Tyr Asp Asp Phe Thr Ala Ser Leu Pro Ala Asp Cys Arg Tyr Ala
 65                  70                  75                  80

Val Tyr Asp Leu Asp Phe Val Ser Asp Asp Asn Cys Arg Lys Ser Lys
                 85                  90                  95

Ile Phe Phe Ile Ser Trp Ser Pro Ser Val Ser Arg Ile Arg Ala Lys
                100                 105                 110

Thr Ile Tyr Ala Val Ser Arg Asn Gln Phe Arg His Glu Leu Asp Gly
            115                 120                 125

Val His Phe Glu Ile Gln Ala Thr Asp Pro Asp Met Asp Leu Glu
        130                 135                 140

Val Leu Arg Gly Arg Ala Asn Arg Thr
145                 150

<210> SEQ ID NO 23
<211> LENGTH: 139
<212> TYPE: PRT
<213> ORGANISM: Oryza sativa

<400> SEQUENCE: 23

Met Ala Asn Ser Ser Ser Gly Val Ala Ile His Asp Asp Cys Lys Leu
 1               5                  10                  15

Lys Phe Asn Glu Leu Gln Ser Lys Arg Met His Arg Phe Ile Thr Phe
                 20                  25                  30

Met Met Asp Asn Lys Gly Lys Glu Ile Ile Val Asp Lys Ile Gly Asp
             35                  40                  45

Arg Thr Thr Ser Tyr Glu Asp Phe Thr Ser Ser Leu Pro Glu Gly Asp
 50                  55                  60
```

```
Cys Arg Phe Ala Ile Tyr Asp Phe Asp Phe Leu Thr Ala Glu Asp Val
 65                  70                  75                  80

Pro Lys Ser Arg Ile Phe Tyr Ile Leu Trp Ser Pro Asp Asn Ala Lys
                 85                  90                  95

Val Arg Ser Lys Met Leu Tyr Ala Ser Ser Asn Glu Arg Phe Lys Lys
            100                 105                 110

Glu Leu Asn Gly Ile Gln Leu Glu Val Gln Ala Thr Asp Ala Gly Glu
        115                 120                 125

Ile Ser Leu Asp Ala Leu Lys Asp Arg Val Lys
    130                 135
```

<210> SEQ ID NO 24
<211> LENGTH: 145
<212> TYPE: PRT
<213> ORGANISM: Oryza sativa

<400> SEQUENCE: 24

```
Met Ala Phe Val Arg Ser Arg Ala Asn Ala Ser Ser Gly Ile Gly Val
  1               5                  10                  15

Ala Ala Glu Cys Lys Gln Thr Phe Leu Glu Leu Gln Arg Lys Lys Ser
             20                  25                  30

His Arg Tyr Val Ile Phe Lys Ile Asp Asp Lys Cys Lys Glu Val Val
         35                  40                  45

Val Glu Lys Thr Gly Ser Ser Thr Glu Ser Phe Asp Asp Phe Met Asp
 50                  55                  60

Ser Leu Pro Glu Ser Asp Cys Arg Tyr Ala Ile Tyr Asp Phe Asp Phe
 65                  70                  75                  80

Val Thr Glu Glu Asn Cys Gln Lys Ser Lys Ile Phe Phe Val Ala Trp
                 85                  90                  95

Ser Pro Ser Val Ser Arg Ile Arg Ala Lys Met Leu Tyr Ala Thr Ser
            100                 105                 110

Lys Glu Arg Phe Arg Arg Glu Leu Asp Gly Val His Tyr Glu Ile Gln
        115                 120                 125

Ala Thr Asp Pro Ser Glu Leu Asp Ile Glu Leu Leu Arg Glu Arg Ala
    130                 135                 140

His
145
```

<210> SEQ ID NO 25
<211> LENGTH: 143
<212> TYPE: PRT
<213> ORGANISM: Oryza sativa

<400> SEQUENCE: 25

```
Met Ala Met Ala Tyr Lys Met Ala Thr Glu Gly Met Asn Val Lys Glu
  1               5                  10                  15

Glu Cys Gln Arg Trp Phe Met Glu Met Lys Trp Lys Lys Val His Arg
             20                  25                  30

Phe Val Val Tyr Lys Ile Asp Glu Arg Ser Arg Ala Val Leu Val Asp
         35                  40                  45

Lys Val Gly Gly Pro Gly Glu Gly Tyr Glu Glu Leu Val Ala Ala Leu
 50                  55                  60

Pro Thr Asp Asp Cys Arg Tyr Ala Val Phe Asp Phe Asp Phe Val Thr
 65                  70                  75                  80

Val Asp Asn Cys Gln Lys Ser Lys Ile Phe Phe Ile Ala Trp Ser Pro
                 85                  90                  95

Thr Ala Ser Arg Ile Arg Ala Lys Ile Leu Tyr Ala Thr Ser Lys Gln
```

```
              100                 105                 110
Gly Leu Arg Arg Val Leu Asp Gly Val His Tyr Glu Val Gln Ala Thr
            115                 120                 125

Asp Ser Ser Glu Met Gly Tyr Asp Val Ile Arg Gly Arg Ala Gln
        130                 135                 140

<210> SEQ ID NO 26
<211> LENGTH: 145
<212> TYPE: PRT
<213> ORGANISM: Oryza sativa

<400> SEQUENCE: 26

Met Ala Phe Met Arg Ser His Ser Asn Ala Ser Ser Gly Met Gly Val
1               5                   10                  15

Ala Pro Asp Ile Arg Asp Thr Phe Leu Glu Leu Gln Met Lys Lys Ala
            20                  25                  30

Phe Arg Tyr Val Ile Phe Lys Ile Glu Glu Lys Gln Lys Gln Val Val
        35                  40                  45

Val Glu Lys Thr Gly Ala Thr Thr Glu Ser Tyr Asp Asp Phe Leu Ala
    50                  55                  60

Ser Leu Pro Glu Asn Asp Cys Arg Tyr Ala Leu Tyr Asp Phe Asp Phe
65                  70                  75                  80

Val Thr Gly Glu Asn Val Gln Lys Ser Lys Ile Phe Phe Ile Ala Trp
                85                  90                  95

Ser Pro Ser Thr Ser Arg Ile Arg Ala Lys Met Leu Tyr Ser Thr Ser
            100                 105                 110

Lys Asp Arg Ile Lys Gln Glu Leu Asp Gly Phe His Tyr Glu Ile Gln
        115                 120                 125

Ala Thr Asp Pro Thr Glu Val Asp Leu Glu Val Leu Arg Glu Arg Ala
    130                 135                 140

His
145

<210> SEQ ID NO 27
<211> LENGTH: 139
<212> TYPE: PRT
<213> ORGANISM: Oryza sativa

<400> SEQUENCE: 27

Met Ala Asn Ser Ala Ser Gly Met Ala Val Gly Asp Glu Cys Lys Leu
1               5                   10                  15

Lys Phe Gln Glu Leu Lys Ser Lys Arg Ser Phe Arg Phe Ile Thr Phe
            20                  25                  30

Lys Ile Asp Glu Arg Thr Gln Gln Val Val Val Asp Arg Leu Gly Gln
        35                  40                  45

Pro Gly Asp Thr Tyr Asp Asp Phe Thr Ala Ser Met Pro Ala Ser Glu
    50                  55                  60

Cys Arg Tyr Ala Val Phe Asp Phe Asp Phe Val Thr Asp Glu Asn Cys
65                  70                  75                  80

Gln Lys Ser Lys Ile Phe Phe Ile Ser Trp Ser Pro Asp Thr Ser Lys
                85                  90                  95

Val Arg Ser Lys Met Leu Tyr Ala Ser Ser Lys Asp Arg Phe Lys Arg
            100                 105                 110

Glu Leu Asp Gly Ile Gln Val Glu Leu Gln Ala Thr Asp Pro Ser Glu
        115                 120                 125

Met Ser Met Asp Ile Val Lys Ala Arg Ala Leu
    130                 135
```

```
<210> SEQ ID NO 28
<211> LENGTH: 139
<212> TYPE: PRT
<213> ORGANISM: Oryza sativa

<400> SEQUENCE: 28

Met Ala Asn Ser Ala Ser Gly Leu Ala Val Asn Asp Glu Cys Lys Phe
1               5                   10                  15

Lys Phe Gln Glu Leu Lys Thr Arg Arg Gly Phe Arg Phe Ile Val Phe
            20                  25                  30

Lys Ile Asp Asp Lys Ala Met Glu Ile Lys Val Glu Arg Leu Gly Gln
        35                  40                  45

Thr Ala Glu Gly Tyr Glu Asp Phe Ala Ala Thr Leu Pro Ala Asp Glu
    50                  55                  60

Cys Arg Tyr Ala Val Tyr Asp Leu Asp Phe Val Thr Asp Glu Asn Cys
65                  70                  75                  80

Gln Lys Ser Lys Ile Phe Phe Phe Ser Trp Ser Pro Asp Thr Ala Arg
                85                  90                  95

Thr Arg Ser Lys Met Leu Tyr Ala Ser Ser Lys Asp Arg Phe Arg Arg
            100                 105                 110

Glu Leu Asp Gly Ile Gln Cys Glu Ile Gln Ala Thr Asp Pro Ser Glu
        115                 120                 125

Met Ser Leu Asp Ile Ile Arg Ala Arg Ala His
    130                 135

<210> SEQ ID NO 29
<211> LENGTH: 145
<212> TYPE: PRT
<213> ORGANISM: Oryza sativa

<400> SEQUENCE: 29

Met Ala Met Ala Tyr Lys Met Ala Thr Glu Gly Met Asn Val Lys Glu
1               5                   10                  15

Glu Cys Gln Arg Trp Phe Met Glu Met Lys Trp Lys Lys Val His Arg
            20                  25                  30

Phe Val Val Tyr Lys Ile Asp Glu Arg Ser Arg Ala Val Leu Val Asp
            35                  40                  45

Lys Val Gly Gly Pro Gly Glu Gly Tyr Glu Glu Leu Val Ala Ala Leu
    50                  55                  60

Pro Thr Asp Asp Cys Arg Tyr Ala Val Phe Arg Thr Phe Glu Phe Arg
65                  70                  75                  80

His Arg Arg Gln Leu Pro Glu Glu Ala Arg Ser Phe Phe Ile Ala Trp
                85                  90                  95

Ser Pro Thr Ala Ser Arg Ile Arg Ala Lys Ile Leu Tyr Ala Thr Ser
            100                 105                 110

Lys Gln Gly Leu Arg Arg Val Leu Asp Gly Val His Tyr Glu Val Gln
        115                 120                 125

Ala Thr Asp Ser Ser Glu Met Gly Tyr Asp Val Ile Arg Gly Arg Ala
    130                 135                 140

Gln
145

<210> SEQ ID NO 30
<211> LENGTH: 139
<212> TYPE: PRT
<213> ORGANISM: Oryza sativa
```

```
<400> SEQUENCE: 30

Met Ser Asn Ser Ala Ser Gly Met Ala Val Cys Asp Glu Cys Lys Leu
1               5                   10                  15

Lys Phe Leu Glu Leu Lys Ala Lys Arg Ser Phe Arg Phe Ile Val Phe
                20                  25                  30

Lys Ile Asn Glu Lys Val Gln Gln Val Val Asp Arg Leu Gly Gln
                35                  40                  45

Pro Gly Glu Ser Tyr Asp Phe Thr Ala Cys Leu Pro Ala Asp Glu
    50                  55                  60

Cys Arg Tyr Ala Val Phe Asp Phe Asp Phe Val Thr Asp Glu Asn Cys
65                  70                  75                  80

Gln Lys Ser Lys Ile Phe Phe Ile Ser Trp Ala Pro Asp Thr Ser Arg
                85                  90                  95

Val Arg Ser Lys Met Leu Tyr Ala Ser Ser Lys Asp Arg Phe Lys Arg
                100                 105                 110

Glu Leu Asp Gly Ile Gln Val Glu Leu Gln Ala Thr Pro Ser Glu
                115                 120                 125

Met Ser Met Asp Ile Val Lys Ser Arg Ala Leu
    130                 135

<210> SEQ ID NO 31
<211> LENGTH: 150
<212> TYPE: PRT
<213> ORGANISM: Oryza sativa

<400> SEQUENCE: 31

Met Ala Asn Ala Thr Ser Gly Val Ala Val Ser Glu Glu Cys Lys Ala
1               5                   10                  15

Arg Phe Gln Glu Leu Arg Ala Gly Arg Ala His Arg Phe Val Val Phe
                20                  25                  30

Lys Ile Asp Asp Ala Met Arg Gln Val Val Val Asp Arg Val Gly Pro
                35                  40                  45

Arg Asp Ala Gly Phe Asp Glu Leu Thr Ala Ser Leu Pro Ala Asp Gly
    50                  55                  60

Cys Arg Tyr Ala Val Tyr Asp His Asp Phe Thr Val Ser Asp Ala Thr
65                  70                  75                  80

Ala Thr Ala Ala Ala Gly Glu Gly Gly Glu Ala Pro Arg Ser Lys Ile
                85                  90                  95

Phe Phe Val Ser Trp Ser Pro Ala Ala Ala Asp Val Arg Ser Lys Met
                100                 105                 110

Val Tyr Ala Ser Ser Asn Glu Gly Phe Lys Lys Glu Leu Asp Gly Val
                115                 120                 125

Gln Ile Asp Leu Gln Ala Thr Asp Pro Ser Glu Leu Thr Leu Asp Val
    130                 135                 140

Leu Lys Asp His Thr Ser
145                 150

<210> SEQ ID NO 32
<211> LENGTH: 139
<212> TYPE: PRT
<213> ORGANISM: Triticum aestivum

<400> SEQUENCE: 32

Met Ala Asn Ala Ala Ser Gly Met Ala Val Asp Asp Glu Cys Lys Leu
1               5                   10                  15

Lys Phe Leu Glu Leu Lys Ala Lys Arg Thr His Arg Phe Ile Ile Tyr
                20                  25                  30
```

```
Lys Ile Asp Asp Lys Lys Met Val Val Glu Lys Val Gly Glu
            35                  40                  45

Pro Ala Leu Asn Tyr Glu Asp Phe Ala Ser Leu Pro Thr Asn Glu
 50                  55                  60

Cys Arg Tyr Ala Ile Phe Asp Tyr Asp Phe Thr Glu Glu Asn Cys
 65                  70                  75                  80

Gln Lys Ser Lys Ile Phe Phe Val Ala Trp Ser Pro Asp Thr Ala Arg
                85                  90                  95

Val Arg Ser Lys Met Ile Tyr Ala Ser Ser Lys Glu Arg Phe Lys Arg
                100                 105                 110

Glu Leu Asp Gly Ile Gln Val Glu Leu Gln Ala Thr Asp Pro Thr Glu
                115                 120                 125

Val Gly Phe Asp Val Ile Gln Gly Arg Ala Asn
                130                 135
```

```
<210> SEQ ID NO 33
<211> LENGTH: 139
<212> TYPE: PRT
<213> ORGANISM: Triticum aestivum

<400> SEQUENCE: 33

Met Ser Asn Ser Ala Ser Gly Met Ala Val Cys Asp Glu Cys Lys Leu
 1               5                  10                  15

Lys Phe Gln Glu Leu Lys Ala Lys Arg Ser Phe Arg Phe Ile Val Phe
                20                  25                  30

Lys Ile Asn Glu Lys Val Gln Gln Val Val Asp Arg Val Gly Glu
            35                  40                  45

Lys Thr Glu Ser Tyr Asp Asp Phe Thr Ala Cys Leu Pro Ala Asp Glu
 50                  55                  60

Cys Arg Tyr Ala Val Phe Asp Phe Asp Phe Val Thr Asp Glu Asn Cys
 65                  70                  75                  80

Gln Lys Ser Lys Ile Phe Phe Ile Ser Trp Ala Pro Asp Thr Ser Arg
                85                  90                  95

Val Arg Ser Lys Met Leu Tyr Ala Ser Ser Lys Asp Arg Phe Lys Arg
                100                 105                 110

Glu Leu Asp Gly Ile Gln Val Glu Leu Gln Ala Thr Asp Pro Ser Glu
                115                 120                 125

Met Ser Met Asp Ile Val Lys Gly Arg Ala Leu
                130                 135
```

```
<210> SEQ ID NO 34
<211> LENGTH: 138
<212> TYPE: PRT
<213> ORGANISM: Triticum aestivum

<400> SEQUENCE: 34

Met Ala Asn Ala Ser Ser Gly Ala Gly Ile His Asp Asp Cys Lys Leu
 1               5                  10                  15

Arg Phe Val Glu Leu Lys Ser Lys Arg Met His Arg Phe Ile Thr Tyr
                20                  25                  30

Arg Leu Glu Asn Gln Lys Glu Val Ile Val Asp Gln Thr Gly Glu Arg
            35                  40                  45

Glu Ala Thr Tyr Glu Asp Phe Thr Lys Thr Leu Pro Glu Asn Asp Cys
 50                  55                  60

Arg Phe Ala Val Phe Asp Phe Asp Phe Thr Thr Pro Glu Asp Val Pro
 65                  70                  75                  80
```

```
Lys Ser Arg Ile Phe Tyr Ile Phe Trp Ser Pro Asp Thr Ala Lys Val
            85                  90                  95

Arg Ser Lys Met Thr Tyr Ala Ser Thr Asn Glu Lys Phe Lys Arg Thr
            100                 105                 110

Leu Asp Gly Ile Gln Ile Glu Met Gln Ala Thr Asp Pro Ser Glu Ile
            115                 120                 125

Ser Leu Asp Val Ile Lys Glu Arg Ala His
            130                 135
```

<210> SEQ ID NO 35
<211> LENGTH: 139
<212> TYPE: PRT
<213> ORGANISM: Triticum aestivum

<400> SEQUENCE: 35

```
Met Ala Asn Ala Arg Ser Gly Val Ala Val Asn Asp Glu Cys Met Leu
1               5                   10                  15

Lys Phe Gly Glu Leu Gln Ser Lys Arg Leu His Arg Phe Ile Thr Tyr
            20                  25                  30

Lys Met Asp Asp Lys Phe Lys Glu Ile Val Val Asp Gln Val Gly Asp
            35                  40                  45

Arg Ala Thr Ser Tyr Glu Asp Phe Thr Asn Ser Leu Pro Glu Asn Asp
        50                  55                  60

Cys Arg Tyr Ala Ile Tyr Asp Phe Asp Phe Thr Ala Glu Asp Val
65                  70                  75                  80

Gln Lys Ser Arg Ile Phe Tyr Ile Leu Trp Ser Pro Asp Ser Ala Lys
            85                  90                  95

Val Lys Ser Lys Met Leu Tyr Ala Ser Ser Asn Gln Lys Phe Lys Ser
            100                 105                 110

Gly Leu Asn Gly Ile Gln Val Glu Leu Gln Ala Thr Asp Ala Ser Glu
            115                 120                 125

Ile Ser Ile Asp Gln Ile Lys Asp Arg Ala Arg
            130                 135
```

<210> SEQ ID NO 36
<211> LENGTH: 139
<212> TYPE: PRT
<213> ORGANISM: Triticum aestivum

<400> SEQUENCE: 36

```
Met Ala Asn Ser Ala Ser Gly Met Ala Val Ser Asp Glu Cys Lys Leu
1               5                   10                  15

Lys Phe Gln Glu Leu Lys Ala Lys Arg Thr Phe Arg Phe Ile Thr Phe
            20                  25                  30

Lys Ile Asn Glu His Ser Gln Gln Val Val Val Asp Arg Val Gly Gln
            35                  40                  45

Pro Gly Glu Thr Tyr Ala Asp Phe Thr Ala Thr Ile Pro Ala Asp Glu
        50                  55                  60

Cys Arg Tyr Ala Val Phe Asp Phe Asp Phe Val Thr Asp Glu Asn Cys
65                  70                  75                  80

Gln Lys Ser Lys Ile Phe Phe Ile Ser Trp Ser Pro Asp Thr Ser Arg
            85                  90                  95

Val Arg Ser Lys Met Leu Tyr Ala Ser Ser Lys Asp Arg Phe Lys Arg
            100                 105                 110

Glu Leu Asp Gly Tyr Gln Val Glu Leu Gln Ala Thr Glu Pro Ser Glu
            115                 120                 125

Met Thr Leu Asp Ile Val Lys Ala Arg Ala Leu
```

<210> SEQ ID NO 37
<211> LENGTH: 143
<212> TYPE: PRT
<213> ORGANISM: Triticum aestivum

<400> SEQUENCE: 37

Met Ala Met Ala Tyr Lys Met Ala Thr Glu Gly Met Asn Ile Lys Glu
1               5                   10                  15

Glu Cys Lys Arg Trp Phe Thr Glu Met Lys Trp Lys Lys Val His Arg
            20                  25                  30

Phe Val Val Tyr Lys Ile Asp Glu Arg Thr Arg Ala Val Leu Val Asp
        35                  40                  45

Lys Val Gly Gly Pro Gly Glu Gly Tyr Asp Glu Leu Val Ala Ala Leu
    50                  55                  60

Pro Gly Asp Asp Cys Arg Tyr Ala Val Phe Asp Phe Asp Phe Val Ser
65                  70                  75                  80

Val Asp Asn Cys Gln Lys Ser Lys Ile Phe Phe Ile Ala Trp Ser Pro
                85                  90                  95

Ala Ala Ser Arg Ile Arg Ala Lys Ile Leu Tyr Ala Thr Ser Lys Gln
            100                 105                 110

Gly Leu Arg Arg Val Leu Glu Gly Val His Tyr Glu Val Gln Ala Thr
        115                 120                 125

Glu Arg Ser Glu Met Gly Phe Asp Val Ile Arg Glu Arg Ala Gln
    130                 135                 140

<210> SEQ ID NO 38
<211> LENGTH: 145
<212> TYPE: PRT
<213> ORGANISM: Triticum aestivum

<400> SEQUENCE: 38

Met Ala Phe Met Arg Thr Ser Ser Asn Ala Ser Ser Gly Met Gly Val
1               5                   10                  15

Ala Pro Asp Ile Arg Glu Thr Phe Leu Glu Leu Gln Met Lys Lys Ala
            20                  25                  30

Phe Arg Tyr Val Ile Phe Lys Ile Glu Glu Lys Gln Lys Gln Val Val
        35                  40                  45

Val Glu Lys Thr Gly Ala Thr Thr Glu Ser Tyr Asp Asp Phe Leu Ala
    50                  55                  60

Cys Leu Pro Glu Lys Asp Cys Arg Tyr Ala Leu Tyr Asp Phe Asp Phe
65                  70                  75                  80

Val Thr Gly Glu Asn Val Gln Lys Ser Lys Ile Phe Phe Ile Ala Trp
                85                  90                  95

Ser Pro Asp Thr Ser Arg Ile Arg Ala Lys Met Leu Tyr Ser Thr Ser
            100                 105                 110

Lys Asp Arg Ile Lys Gln Glu Leu Asp Gly Phe His Tyr Glu Ile Gln
        115                 120                 125

Ala Thr Asp Pro Thr Glu Val Glu Leu Asp Val Leu Arg Asp Arg Ala
    130                 135                 140

His
145

<210> SEQ ID NO 39
<211> LENGTH: 139
<212> TYPE: PRT
<213> ORGANISM: Zea mays

```
<400> SEQUENCE: 39

Met Ala Asn Ala Ala Ser Gly Met Ala Val Asp Asp Cys Lys Arg
1               5                   10                  15

Arg Phe Leu Glu Leu Lys Ala Lys Arg Thr His Arg Phe Ile Ile Tyr
            20                  25                  30

Arg Ile Asp Glu Lys Lys Lys Met Val Val Glu Gln Val Gly Lys
            35                  40                  45

Pro Val Leu Gly Tyr Asp Asp Phe Ala Ala Ser Leu Pro Ala Asn Glu
            50                  55                  60

Cys Arg Tyr Ala Ile Phe Asp Tyr Asp Phe Val Thr Glu Glu Asn Cys
65                  70                  75                  80

Gln Lys Ser Lys Ile Phe Phe Ile Ala Trp Ser Pro Asp Thr Ala Arg
                85                  90                  95

Val Arg Ser Lys Met Ile Tyr Ala Ser Ser Lys Glu Arg Phe Lys Arg
            100                 105                 110

Glu Leu Asp Gly Ile Gln Val Asp Leu Gln Ala Thr Asp Ser Ala Glu
            115                 120                 125

Val Gly Leu Asp Val Ile Gln Gly Arg Ala Ser
            130                 135

<210> SEQ ID NO 40
<211> LENGTH: 139
<212> TYPE: PRT
<213> ORGANISM: Zea mays

<400> SEQUENCE: 40

Met Ala Asn Ser Ser Ser Gly Leu Ala Val Asn Asp Glu Cys Lys Val
1               5                   10                  15

Lys Phe Arg Glu Leu Lys Ser Arg Arg Ser Phe Arg Phe Ile Val Phe
            20                  25                  30

Arg Ile Asp Asp Thr Asp Met Glu Ile Lys Val Asp Arg Leu Gly Gly
            35                  40                  45

Pro Asn Gln Gly Tyr Gly Asp Phe Thr Asp Ser Leu Pro Ala Asn Glu
            50                  55                  60

Cys Arg Tyr Ala Ile Tyr Asp Leu Asp Phe Thr Thr Ile Glu Asn Cys
65                  70                  75                  80

Gln Lys Ser Lys Ile Phe Phe Phe Ser Trp Ser Pro Asp Thr Ala Arg
                85                  90                  95

Thr Arg Ser Lys Met Leu Tyr Ala Ser Ser Lys Asp Arg Phe Arg Arg
            100                 105                 110

Glu Leu Asp Gly Ile Gln Cys Glu Ile Gln Ala Thr Asp Pro Ser Glu
            115                 120                 125

Met Ser Leu Asp Ile Val Arg Ser Arg Thr Asn
            130                 135

<210> SEQ ID NO 41
<211> LENGTH: 139
<212> TYPE: PRT
<213> ORGANISM: Zea mays

<400> SEQUENCE: 41

Met Ala Asn Ala Arg Ser Gly Val Ala Val Asn Asp Glu Cys Met Leu
1               5                   10                  15

Lys Phe Gly Glu Leu Gln Ser Lys Arg Leu His Arg Phe Leu Thr Phe
            20                  25                  30

Lys Met Asp Asp Lys Phe Lys Glu Ile Val Val Asp Gln Val Gly Asp
```

```
                35                  40                  45
Arg Ala Thr Ser Tyr Glu Asp Phe Thr Asn Ser Leu Pro Glu Asn Asp
 50                  55                  60

Cys Arg Tyr Ala Ile Tyr Asp Phe Asp Phe Val Thr Ala Glu Asp Val
 65                  70                  75                  80

Gln Lys Ser Arg Ile Phe Tyr Ile Leu Trp Ser Pro Ser Ser Ala Lys
                 85                  90                  95

Val Lys Ser Lys Met Leu Tyr Ala Ser Ser Asn Gln Lys Phe Lys Ser
                100                 105                 110

Gly Leu Asn Gly Ile Gln Val Glu Leu Gln Ala Thr Asp Ala Ser Glu
                115                 120                 125

Ile Ser Leu Asp Glu Ile Lys Asp Arg Ala Arg
                130                 135

<210> SEQ ID NO 42
<211> LENGTH: 143
<212> TYPE: PRT
<213> ORGANISM: Zea mays

<400> SEQUENCE: 42

Met Ala Met Ala Tyr Lys Met Ala Thr Glu Gly Met Asn Val Lys Glu
  1               5                  10                  15

Glu Cys Gln Arg Trp Phe Met Glu Met Lys Trp Lys Lys Val His Arg
                 20                  25                  30

Phe Val Val Tyr Lys Ile Asp Glu Arg Ser Arg Ala Val Leu Val Asp
                 35                  40                  45

Lys Val Gly Gly Pro Gly Gly Tyr Glu Glu Leu Val Ala Ala Leu
 50                  55                  60

Pro Gly Asp Asp Cys Arg Tyr Ala Val Phe Asp Phe Asp Phe Val Thr
 65                  70                  75                  80

Val Asp Asn Cys Gln Lys Ser Lys Ile Phe Phe Ile Ala Trp Ser Pro
                 85                  90                  95

Ala Ala Ser Arg Ile Arg Ala Lys Ile Leu Tyr Ala Thr Ser Lys Gln
                100                 105                 110

Gly Leu Arg Arg Leu Leu Asp Gly Val His Tyr Glu Val Gln Ala Thr
                115                 120                 125

Asp Pro Ser Glu Met Gly Phe Asp Val Ile Arg Gly Arg Ala Gln
                130                 135                 140

<210> SEQ ID NO 43
<211> LENGTH: 145
<212> TYPE: PRT
<213> ORGANISM: Zea mays

<400> SEQUENCE: 43

Met Ala Phe Met Arg Ser Arg Ser Asn Ala Ser Ser Gly Met Gly Val
  1               5                  10                  15

Ala Pro Asn Ile Arg Glu Thr Phe Val Glu Leu Gln Met Lys Lys Ala
                 20                  25                  30

Phe Arg Tyr Val Ile Phe Lys Ile Glu Glu Lys Gln Lys Gln Val Val
                 35                  40                  45

Val Glu Lys Thr Gly Ala Thr Thr Glu Ser Tyr Asp Asp Phe Leu Ala
 50                  55                  60

Ser Leu Pro Glu Asn Asp Cys Arg Tyr Ala Leu Tyr Asp Phe Asp Phe
 65                  70                  75                  80

Val Thr Gly Glu Asn Val Gln Lys Ser Lys Ile Phe Phe Ile Ala Trp
                 85                  90                  95
```

```
Ser Pro Ser Thr Ser Arg Ile Arg Ala Lys Met Leu Tyr Ser Thr Ser
            100                 105                 110

Lys Asp Arg Ile Lys Tyr Glu Leu Asp Gly Phe His Tyr Glu Ile Gln
        115                 120                 125

Ala Thr Asp Pro Ser Glu Val Asp Ile Glu Val Leu Arg Glu Arg Ala
    130                 135                 140

His
145

<210> SEQ ID NO 44
<211> LENGTH: 139
<212> TYPE: PRT
<213> ORGANISM: Zea mays

<400> SEQUENCE: 44

Met Ser Asn Ser Ala Ser Gly Met Ala Val Cys Asp Glu Cys Lys Leu
1               5                   10                  15

Lys Phe Gln Glu Leu Lys Ala Lys Arg Ser Phe Arg Phe Ile Val Phe
            20                  25                  30

Lys Ile Asn Glu Asn Val Gln Gln Val Val Val Asp Arg Leu Gly Glu
        35                  40                  45

Pro Gly Glu Ser Tyr Asp Ala Phe Thr Ala Cys Phe Pro Ala Asn Glu
    50                  55                  60

Cys Arg Tyr Ala Val Phe Asp Phe Asp Phe Val Thr Asp Glu Asn Cys
65                  70                  75                  80

Gln Lys Ser Lys Ile Phe Phe Ile Ser Trp Ala Pro Thr Ser Arg
                85                  90                  95

Val Arg Ser Lys Met Leu Tyr Ala Ser Ser Lys Asp Arg Phe Lys Arg
            100                 105                 110

Glu Leu Asp Gly Ile Gln Val Glu Leu Gln Ala Thr Asp Pro Ser Glu
        115                 120                 125

Met Ser Met Asp Ile Val Lys Ser Arg Ala Leu
    130                 135

<210> SEQ ID NO 45
<211> LENGTH: 417
<212> TYPE: DNA
<213> ORGANISM: Hordeum vulgare

<400> SEQUENCE: 45
atggcaaacg cttcatcagg tgctgggatc catgacgact gcaagctgag gttcgtggag    60
ctcaagtcca agaggatgca ccgcttcata acctacaggc tggagaacca gaaggaggtc   120
attgtggacc aaaccgggca gcgcgatgcc acctatgagg atttcaccaa gaccctccct   180
gaaaacgact gccgattcgc agtgtttgac ttcgacttca ccaccccaga ggatgtgcca   240
aagagcagga tcttctatat cttctggtcc ccggacaccg caaaggtgag gagcaagatg   300
acgtacgcga gcaccaacga gaagttcaag aggaccctgg acggcatcca gatcgagatg   360
caggccaccg accccagcga aatcagcctg gacgtgatca aggagcgcgc acactag      417

<210> SEQ ID NO 46
<211> LENGTH: 417
<212> TYPE: DNA
<213> ORGANISM: Hordeum vulgare

<400> SEQUENCE: 46
atggcaaacg cttcagcagg tgctgggatc catgacgact gcaagctgag gttcgtggag    60
```

```
ctcaagtcca agaggatgca ccgcttcata acctacaggc tggagaacca gaaggaggtc    120
attgtggacc aaaccgggca gcgcgatgcc acctatgagg atttcaccaa gaccctccct    180
gaaaacgact gccgattcgc agtgtttgac ttcgacttca ccaccccgga ggatgtgcca    240
aagagcagga tcttctatat cttctggtcc ccggacaccg caaaggtgag gagcaagatg    300
acgtacgcga gcaccaacga gaagttcaag aggaccctgg acggcatcca gatcgagatg    360
caggccaccg accccagcga aatcagcctg gacgtgatca aggagcgcgc acactag       417
```

<210> SEQ ID NO 47
<211> LENGTH: 419
<212> TYPE: DNA
<213> ORGANISM: Hordeum vulgare

<400> SEQUENCE: 47

```
atggcaaacg ctgcgtcagg catggctgtg gacgacgaat gcaagctcaa gttcctggag     60
ctgaaggcga gcgaacccca ccgcttcatc atctacaaga tagatgacaa gaagaagatg    120
gttgtggtgg agaaggtcgg cgagcctgcc ctgaactatg aggacttcgc cgccagcctc    180
cccaccaatg aatgcagata cgcgatattc gactatgact ttgtcactga ggagaactgc    240
cagaagagca agatattctt cgtcgcatgg tctcctgaca ccgcacgcgt gaggagcaag    300
atgatctacg cgagctccaa ggagaggttc aagagggagc tcgatggcat ccaagtagag    360
ctgcaggcga cagacccgac cgaggtcggc tttgatgtca tccaaggccg cgccaactg     419
```

<210> SEQ ID NO 48
<211> LENGTH: 470
<212> TYPE: DNA
<213> ORGANISM: Hordeum vulgare

<400> SEQUENCE: 48

```
atggcgctgg cggcggcgcc ggcggccttg gcgtggccat ccctgggtgg gaactcgccg     60
gcgtggattg acgtcccgga gcggagcaag agcgcgttca tggagctcaa gaggaggaag    120
gtgcaccggt acgtgatatt caagatcgac gacagcacgg aggaggtcgt ggtcgagaag    180
accggctcac ccggggaaag ctacgacgac ttcacggcct cgttgcccgt cgacgactgc    240
cgctacgccg tttacgatct ggatttcgtc agcgacgaca actgccgcaa gagcaagatt    300
ttcttcatct cctggtctcc tgatgattct cgcatccgtg caaagaccat atatgctgtg    360
tccaggaatc aattccgcca tgagctcgac ggggtgcact ttgagatcca ggcaactgac    420
cctgatgaca tggacttgga agttctcagg gtccgtgcta atagaacctg                470
```

<210> SEQ ID NO 49
<211> LENGTH: 431
<212> TYPE: DNA
<213> ORGANISM: Hordeum vulgare

<400> SEQUENCE: 49

```
atggcaatgg cttacaagat ggcgacggag gggatgaaca tcaaggagga gtgcaagcgg     60
tggttcacgg agatgaagtg gaagaaggtg caccgcttcg tggtctacaa gatcgacgag    120
cgcacccgcg ccgtgctggt ggacaaggtg gcggccccg ggagggta cgaggagctc       180 gtcgccgcgc tgcccaccga cgactgccgc tacgccgtct cgacttcga cttcgtctcc     240 gtcgacaact gccagaagag caagatcttc ttcatcgcat ggtcgccggc ggcgtcgagg    300
atacgggcca agattctgta cgcgacgtcg aagcaaggcc tgcggcgggt gctggacggg    360
gtccactacg aggtgcaggc caccgacccc tccgagatgg gcttcgacgt catcagggag    420
```
cgcgcgcaat g                                                              431

<210> SEQ ID NO 50
<211> LENGTH: 438
<212> TYPE: DNA
<213> ORGANISM: Hordeum vulgare

<400> SEQUENCE: 50
atggccttca tgcgcacctc ctccaatgca tcctctggca tgggagttgc tcctgatatc      60
agggagacat tcctggagct tcagatgaag aaggcatttc gctatgttat cttcaagata     120
gaagaaaagc aaaagcaggt tgttgtggag aagacagggg ctacaactga gagttatgat     180
gatttcctgg cttgtctccc agagaacgac tgcagatatg cgctttatga ttttgacttt     240
gttactgggg agaatgtgca gaaaagcaag attttcttca ttgcctggtc ccctgacaca     300
tcccgcatcc gagccaagat gctgtactcc acctccaagg accgcatcaa gcaagagctc     360
gacgggttcc actacgagat ccaggcaact gacccgaccg aggtggagct cgacgtcctc     420
cgtgaccggg cgcactag                                                    438

<210> SEQ ID NO 51
<211> LENGTH: 419
<212> TYPE: DNA
<213> ORGANISM: Hordeum vulgare

<400> SEQUENCE: 51
atgtcgaatt ccgcgtcagg aatggctgtt tgcgacgaat gcaaactcaa gttccaggaa      60
ctcaaggcga agaggagctt ccgcttcatc gtgttcaaga tcaatgagaa ggtgcagcag     120
gtggtggtgg acagggtcgg ggaaaaaaac gagagctacg atgatttcgc tgcctgcttg     180
cctgctgacg agtgccgcta tgcggtattt gattttgact tcgtcactga tgagaactgc     240
cagaagagca agatcttctt catctcttgg gctcctgaca catccagggt gaggagcaag     300
atgctgtacg cgagctccaa ggaccgcttc aagagggagc tggacggcat ccaggtggag     360
ctacaggcga ctgacccgag cgagatgagc atggacatcg taaaggcgcg agccctctg     419

<210> SEQ ID NO 52
<211> LENGTH: 504
<212> TYPE: DNA
<213> ORGANISM: Hordeum vulgare

<400> SEQUENCE: 52
atggcgaact cggcgtcggg gatggccgtg agcgacgagt gcaagctcaa gttccaggac      60
ctcaaggcga agcggagctt ccggttcatc accttcaaga tcaacgagaa cacgcagcag     120
gtggtggtgg acagggtggg gcagcccggc gacacctacg ccgacttcac cgcctccatg     180
cccgccgacg agtgccgcta cgccgtcttc gacttcgact tcgtcaccga cgagaactgc     240
cagaagagca agatattctt catctcctgg tccccggact cgtccagggt gaggagcaag     300
atgctgtacg cgagctccaa ggacaggttc aagagggagc tggacggcat ccaggtggag     360
ctgcaggcca ccgagcccag cgagatgagc atggacatcg tcaaggcca gagccctctg     420
aaacagtccc tcgtcgctcc ttccattcca gactccaagg ccagcagctg gatccactac     480
actgcatgtg catgccctac gtac                                             504

<210> SEQ ID NO 53
<211> LENGTH: 420
<212> TYPE: DNA
<213> ORGANISM: Arabidopsis thaliana

<400> SEQUENCE: 53

```
atggcgaacg cggcatctgg aatggctgtg catgatgatt gcaagctgag atttctggaa      60
ctgaaggcta aaaggacaca ccgtttcata gtttacaaga ttgaggagaa gcagaagcaa     120
gttgttgttg agaaagttgg tcaaccgatc caaacttacg aggagtttgc agcatgtctt     180
ccagctgatg aatgccgtta cgccatttac gattttgact ttgtaactgc tgagaattgc     240
cagaagagca agatcttctt catcgcgtgg tgtccggata ttgctaaggt gagaagcaag     300
atgatctacg cgagctccaa ggacaggttc aagagggaac tagatgggat tcaagtagag     360
ctacaggcaa ctgatccaac agagatggat ctcgatgttt tcaggagccg tgccaactaa     420
```

<210> SEQ ID NO 54
<211> LENGTH: 414
<212> TYPE: DNA
<213> ORGANISM: Arabidopsis thaliana

<400> SEQUENCE: 54

```
atggcaaacg cggcatcggg aatggctgtg catgatgatt gcaagctgaa atttatggaa      60
ctgaaggcga aagaacatt ccgtaccata gtctacaaga ttgaggataa gcaagtgatt     120
gtagagaaac tcggtgaacc tgaacaatca tatgatgact ttgcagctag tcttccagct     180
gatgattgcc gatattgcat ttacgatttc gactttgtca ctgcggagaa ctgccagaag     240
agcaagatct tcttcattgc atggtctccg gacactgcca agtgagaga caagatgatt     300
tacgcgagct ctaaagatag gttcaagaga gaactagatg gaattcaagt ggaacttcaa     360
gctactgatc aacagaaat gggtcttgat gttttcaaaa gccgcaccaa ctaa           414
```

<210> SEQ ID NO 55
<211> LENGTH: 420
<212> TYPE: DNA
<213> ORGANISM: Arabidopsis thaliana

<400> SEQUENCE: 55

```
atggctaatg cagcatcagg aatggcagtc catgatgact gcaagctgaa atttatggaa      60
ttgaagacga aaaggacaca ccgtttcatc atttacaaga ttgaggagct gcagaaacaa     120
gtgattgttg agaaaatcgg tgaaccgggt caaacccatg aggaccttgc tgcaagtctt     180
ccagctgatg aatgccgcta tgccattttc gattttgatt tgtcagttc tgagggtgtc     240
ccaaggagca ggattttttt cgtggcatgg tctccggaca cagcaagagt gagaagcaag     300
atgatctatg cgagctccaa ggacaggttc aagagagaac tagacggaat tcaggtcgag     360
cttcaggcaa ccgatccaac cgagatggat cttgatgttt tcaaaagccg agccaattga     420
```

<210> SEQ ID NO 56
<211> LENGTH: 420
<212> TYPE: DNA
<213> ORGANISM: Arabidopsis thaliana

<400> SEQUENCE: 56

```
atggctaatg ctgcgtcagg aatggcagtc catgatgact gcaagctaag atttctggaa      60
ctgaaggcga aaaggacaca ccgtttcatt gtctacaaga ttgaggagaa gcagaagcaa     120
gtgattgttg agaaagttgg tgaacctatt ctaacttacg aggactttgc agcaagtctt     180
ccagctgacg aatgccgata cgccatttat gatttcgact tgtcactgc agagaattgc     240
cagaagagca gatttttctt cattgcatgg tgtcccgacg tagcaaaggt gagaagcaag     300
atgatctatg cgagctctaa ggacaggttc aagcgtgaac ttgatggaat tcaagtggag     360
```

```
cttcaagcaa ctgatccaac tgagatggat cttgatgttt tgaaaagccg cgtcaactaa    420
```

<210> SEQ ID NO 57
<211> LENGTH: 432
<212> TYPE: DNA
<213> ORGANISM: Arabidopsis thaliana

<400> SEQUENCE: 57

```
atggcgatgg ctttcaagat ggcgacgacg gggatgcgtg tgacggatga gtgtacgagt     60
tcattcatgg acatgaaatg gaagaaagtt catagataca tcgttttcaa gatcgaagag    120
aagtcacgta aagtcaccgt cgataaagtc ggcggcgccg tgaaagcta ccacgatctc     180
gaagattctt taccggtgga tgattgtcgc tacgctgtct ttgatttcga ctttgtcacc    240
gtcgataact gccgcaagag caagatcttc ttcattgcat ggtcaccgga ggcatcaaag    300
ataagggcaa agatattgta cgcaacgtcg aaagatgggc tgaggagagt gttggaaggg    360
attcactatg aacttcaagc tactgatccg acggagatgg gtttcgatat tatccaagac    420
cgtgccaaat ag                                                        432
```

<210> SEQ ID NO 58
<211> LENGTH: 441
<212> TYPE: DNA
<213> ORGANISM: Arabidopsis thaliana

<400> SEQUENCE: 58

```
atgtctttca gaggacttag caggccaaat gcaatatctg gaatgggtgt tgcagatgag     60
agcaaaacca catttctaga gcttcaaagg aaaaaaactc atcgctatgt ggtcttcaag    120
attgatgaat ccaaaaaaga agttgttgtt gagaaaactg gaaatcctac agagagctac    180
gatgattttct tagcttcact tcctgataat gactgcagat acgctgttta tgactttgat    240
ttcgttactt ctgagaattg tcaaaagagc aaaatcttct tctttgcttg gtctccttcg    300
acctctggaa ttcgagccaa ggtgctttac tcgacttcta aagaccagtt aagtagggag    360
cttcaaggga ttcactatga gattcaagct actgatccta ctgaggttga tcttgaagtg    420
ttacgcgaac gagcgaactg a                                              441
```

<210> SEQ ID NO 59
<211> LENGTH: 414
<212> TYPE: DNA
<213> ORGANISM: Arabidopsis thaliana

<400> SEQUENCE: 59

```
atggcgaacg cggcgtcggg gatggcggtg gaggacgagt gtaagctgaa gttttggag      60
ctaaaagcga agagaaacta taggttcata atattcagga tagatggaca acaagtggtg    120
gtagaaaagc tgggaagccc ccaagagaac tacgacgatt tcaccaatta cctaccgcca    180
aatgaatgcc gctacgccgt ttatgacttc gacttcacca ctgctgagaa tatccagaag    240
agcaagatct tcttcatagc atggtcaccg gattcatcta gagtaaggat gaagatggtg    300
tatgcgagct caaggacag gttcaagagg gaattggatg gtattcaggt ggagttacaa     360
gccactgacc cgagcgagat gagtctcgac atcatcaaaa gtcgagctct ctag          414
```

<210> SEQ ID NO 60
<211> LENGTH: 423
<212> TYPE: DNA
<213> ORGANISM: Arabidopsis thaliana

<400> SEQUENCE: 60

| | |
|---|---:|
| atggctaatt cagcgtctgg gatgcatgtg aatgatgaat gcaagattaa gttcttagag | 60 |
| ttgaaagcaa agaggactta caggttcatt gtgttcaaaa ttgatgagaa ggcacagcaa | 120 |
| gtgcaaatag aaaagcttgg gaatccagaa gaaacttacg acgattttac cagctctatc | 180 |
| cccgatgacg aatgccgata cgctgtctac gattttgatt tcaccacaga ggacaattgt | 240 |
| cagaagagca agatcttttt catcgcgtgg tcacctgata catcgagagt tcggagtaag | 300 |
| atgttgtatg caagctcaaa agacaggttc aagagagaaa tggaaggaat tcaagttgaa | 360 |
| ttgcaagcaa ctgatcctag tgagatgagc cttgacatca tcaaaggacg actcaatctc | 420 |
| tga | 423 |

<210> SEQ ID NO 61
<211> LENGTH: 393
<212> TYPE: DNA
<213> ORGANISM: Arabidopsis thaliana

<400> SEQUENCE: 61

| | |
|---|---:|
| atgacggatg attgcaagaa atcgttcatg gagatgaaat ggaagaaagt gcatagatac | 60 |
| gtcgtttaca aactcgagga gaagtctcgg aaagtcaccg tcgacaaggt tggtgccgcc | 120 |
| ggcgagagct acgacgatct cgctgcttct ttgccggagg atgactgtcg ttacgccgtg | 180 |
| tttgatttcg attacgtcac cgtcgataac tgtcgtatga gcaagatctt cttcataact | 240 |
| tggtcgccgg aggcttcaag gataagggag aagatgatgt acgcgacgtc gaagagcgga | 300 |
| ctgagaagag tgttggatgg tgttcactac gagcttcaag ccaccgaccc aaccgagatg | 360 |
| ggatttgata aaatccagga ccgggccaaa tga | 393 |

<210> SEQ ID NO 62
<211> LENGTH: 423
<212> TYPE: DNA
<213> ORGANISM: Arabidopsis thaliana

<400> SEQUENCE: 62

| | |
|---|---:|
| atggctaatt cagcgtctgg gatgcacgtt agcgatgagt gcaagctcaa gttcttggag | 60 |
| ttaaaagcaa agaggaacta taggttcatt gtgttcaaaa ttgatgagaa ggctcagcaa | 120 |
| gttatgatag acaagcttgg gaatccagaa gaaacttacg aagatttcac cagatctatt | 180 |
| cccgaggatg agtgccgata tgctgtctat gactatgatt tcaccacccc tgagaactgc | 240 |
| cagaagagca aaatcttttt catcgcatgg tcacctgata catcaagagt gaggagtaag | 300 |
| atgttgtatg caagctcaaa ggacaggttc aagagggaat ggatgggat tcaagttgaa | 360 |
| ttgcaagcaa cagatcctag cgagatgagc ctcgacatca tcaagggacg agtcaatctc | 420 |
| tga | 423 |

<210> SEQ ID NO 63
<211> LENGTH: 393
<212> TYPE: DNA
<213> ORGANISM: Arabidopsis thaliana

<400> SEQUENCE: 63

| | |
|---|---:|
| atggcagtgg aggacgagtg caagctgaag tttttggagc tcaagtcgaa aagaaactat | 60 |
| cgattcataa tattcaggat agacgggcaa caagtggtgg tcgaaaagtt aggaaacccc | 120 |
| gatgagactt acgatgattt caccgcctcc ctccctgcga acgagtgccg ctatgcagtc | 180 |
| ttcgactttg acttcatcac cgatgaaaat tgccagaaga gcaaaatctt cttcattgca | 240 |
| tggtcaccag attcatcaag ggtgaggatg aagatggtgt atgcaagctc taaggataga | 300 |

```
tttaagagag aattggacgg cattcaggtg gagttacaag ccactgatcc tagcgagatg    360
agcttcgaca ttatcaaaag ccgagctctc tag                                 393
```

<210> SEQ ID NO 64
<211> LENGTH: 402
<212> TYPE: DNA
<213> ORGANISM: Arabidopsis thaliana

<400> SEQUENCE: 64

```
atggttttgc atgatgactg caagctaaca ttcttggaac tgaaggagag acgaacattc    60
cgttccatag tctacaagat tgaggacaac atgcaagtga ttgtagagaa acatcactac   120
aaaaaaatgc atggcgaacg tgaacaatca tatgaggagt ttgcaaacag tcttccagct   180
gatgaatgcc gatatgccat tttggatatc gaattcgtcc caggggagag aaagatttgc   240
ttcatcgcgt ggtctccatc cactgccaag atgagaaaga agatgattta ctcgagcact   300
aaggataggt tcaagagaga actagatgga attcaagtgg agtttcacgc aactgatcta   360
accgatataa gtcttgatgc tatcagacgc cgcatcaact aa                      402
```

<210> SEQ ID NO 65
<211> LENGTH: 419
<212> TYPE: DNA
<213> ORGANISM: Oryza sativa

<400> SEQUENCE: 65

```
atggcgaatg cagcatctgg gatggctgtg gacgatgagt gcaagctcaa gttcctggag    60
ctgaaggcaa agaggaccta ccgcttcatc atttacaaga tagacgagaa gaagaagatg   120
gttgtcgtgg agaaggttgg cgagcccgta ctgaactacg acgattttgc cgctagcctc   180
cctgccaacg aatgcagata cgccatattc gactacgatt tcgtgaccga ggagaactgc   240
cagaagagca agatattctt cattgcatgg tctcctgata catcgcgcgt gagaagcaag   300
atgatctacg cgagctccaa ggacaggttc aagagggagc tcgacggcat tcaggtggag   360
ctccaggcga ccgatccaac tgaggttggc ctcgacgtga tcagaggccg tgcaaactg    419
```

<210> SEQ ID NO 66
<211> LENGTH: 461
<212> TYPE: DNA
<213> ORGANISM: Oryza sativa

<400> SEQUENCE: 66

```
atggtggcgg cggcggcggc ggtgttgcca tggggtggcg gcggctcgcc ggcgtggatc    60
gaggtgccgg agaagagcaa gagcgcgttc tgggagctga agaggaggaa ggtgcaccgc   120
tacgtgattt tcaagatcga cgacaggcgg gaggagatcg tcgtcgagaa gaccggcgcg   180
ccgggggaga gctacgacga cttcacggcg tcgctgcccg ccgacgactg ccggtacgcc   240
gtctacgatc tggatttcgt cagcgacgac aactgcagga gagcaagat attcttcatc    300 tcatggtccc cttctgtttc ccgcatccga gccaagacca tatacgccgt gtcgaggaac   360
caatttcggc acgagcttga cggtgtgcac tttgagattc aggccacgga ccctgatgac   420
atggatttgg aagttctcag gggccgtgct aatagaacct g                       461
```

<210> SEQ ID NO 67
<211> LENGTH: 420
<212> TYPE: DNA
<213> ORGANISM: Oryza sativa

<400> SEQUENCE: 67

-continued

| | |
|---|---|
| atggcaaatt catcatctgg agttgcaatt catgatgatt gcaagctgaa gttcaatgag | 60 |
| ctacagtcca aaaggatgca ccgcttcata actttcatga tggataacaa ggggaaagag | 120 |
| atcattgtgg acaagattgg ggatcgcaca acaagctatg aggatttcac tagcagcctg | 180 |
| cctgaagggg actgccggtt tgcaatctat gactttgact tccttactgc agaggatgtg | 240 |
| ccaaagagca ggatattcta tatcttatgg tccccagaca atgcaaaagt gaggagcaag | 300 |
| atgctttatg ctagctccaa cgaaagattc aagaaggagc tgaatggcat tcagttggaa | 360 |
| gtgcaggcta ctgacgccgg cgaaatcagt ctcgatgcgc tcaaagatcg tgtgaaataa | 420 |

<210> SEQ ID NO 68
<211> LENGTH: 437
<212> TYPE: DNA
<213> ORGANISM: Oryza sativa

<400> SEQUENCE: 68

| | |
|---|---|
| atggcattcg tcagatcacg cgcaaatgct tcctctggaa tcggtgtagc tgccgagtgc | 60 |
| aagcagacat ttctggagct tcagaggaag aaatcacacc gctatgtcat cttcaagatc | 120 |
| gacgacaagt gcaaggaggt cgtcgtcgaa aagacaggtt catcgaccga gagcttcgac | 180 |
| gatttcatgg actcactccc tgaatctgac tgccgctacg ccatctacga cttcgacttc | 240 |
| gtcaccgagg agaactgcca agagagcaag atcttcttcg tcgcatggtc gccttcggtt | 300 |
| tctcgcatcc gcgccaagat gttgtatgct acctccaaag aacggttcag gagagagctg | 360 |
| gatggtgtgc actatgagat tcaggcaact gatccgtcgg agctggacat tgagcttctt | 420 |
| agagagcgtg ctcattg | 437 |

<210> SEQ ID NO 69
<211> LENGTH: 431
<212> TYPE: DNA
<213> ORGANISM: Oryza sativa

<400> SEQUENCE: 69

| | |
|---|---|
| atggcaatgg cttacaagat ggcgacggag gggatgaacg tgaaggagga gtgccagagg | 60 |
| tggttcatga agatgaagtg gaagaaggtg caccggttcg tggtgtacaa gatcgacgag | 120 |
| cggtcgcgcg ccgtgctggt ggacaaggtg ggcggccccg gcgaagggta cgaggagctc | 180 |
| gtcgccgcgc tgcccaccga cgactgccgc tacgccgtct tcgacttcga cttcgtcacc | 240 |
| gtcgacaact gccagaagag caagatcttc ttcatcgcct ggtcaccgac cgcatcgagg | 300 |
| ataagagcca agattctgta cgcgacgtcg aagcaagggc tgaggcgggt gcttgacggg | 360 |
| gtccactacg aggtgcaagc cacggactcc tccgagatgg gctacgacgt catccgaggc | 420 |
| cgcgctcagt g | 431 |

<210> SEQ ID NO 70
<211> LENGTH: 438
<212> TYPE: DNA
<213> ORGANISM: Oryza sativa

<400> SEQUENCE: 70

| | |
|---|---|
| atggcgttca tgcgttccca ctccaatgca tcctccggta tgggggttgc tcctgacatc | 60 |
| agggacacat tccttgagct tcagatgaag aaagcatttc gctatgttat cttcaaaatc | 120 |
| gaggaaaagc aaaagcaagt tgttgtggag aagaccgggg caacaactga gagttatgat | 180 |
| gatttcctgg catctctccc agaaaatgac tgcagatatg cctctatga ttttgacttt | 240 |
| gttactgggg agaatgtgca aaagagcaag attttcttca tcgcctggtc tccatcaaca | 300 |

| tcccggatcc gtgctaagat gctgtactcc acctccaagg atcgcatcaa gcaagaactt | 360 |
| gatggattcc actacgagat ccaggcaacc gacccaactg aggtagacct tgaggtcctc | 420 |
| cgggagcggg ctcattaa | 438 |

<210> SEQ ID NO 71
<211> LENGTH: 420
<212> TYPE: DNA
<213> ORGANISM: Oryza sativa

<400> SEQUENCE: 71

| atggcgaact cagcgtcggg gatggccgtg ggcgacgagt gcaagctcaa gttccaggag | 60 |
| ctcaagtcga agaggagctt ccgcttcatc acgttcaaga tcgacgagcg gacgcagcag | 120 |
| gtggtcgtgg acaggctggg ccagccggtc gacacctacg acgacttcac cgcctccatg | 180 |
| cccgccagcg agtgccgcta cgccgtcttc gacttcgact tcgtcaccga cgagaactgc | 240 |
| cagaagagca agatcttctt catctcctgg tcgccggaca cgtcgaaggt gaggagcaag | 300 |
| atgctgtacg cgagctccaa ggaccggttc aagagggagc tggacgggat ccaggtggag | 360 |
| ctgcaggcga ccgatcccag cgagatgagc atggacatcg tcaaagcgag agccctctga | 420 |

<210> SEQ ID NO 72
<211> LENGTH: 420
<212> TYPE: DNA
<213> ORGANISM: Oryza sativa

<400> SEQUENCE: 72

| atggcgaatt ctgcgtcagg gctggcggtg aacgacgagt gcaagttcaa gttccaggag | 60 |
| ctgaagacga ggagggggtt caggttcatc gtgttcaaga tcgacgacaa ggccatggag | 120 |
| atcaaggtgg agaggctcgg gcagactgcc gagggctacg aggacttcgc cgccaccctc | 180 |
| cccgccgacg agtgccgcta cgccgtctac gacctcgact tcgtcaccga cgagaactgc | 240 |
| cagaagagca agatcttctt cttctcctgg tcgcctgaca cggcgaggac aaggagcaag | 300 |
| atgctgtacg cgagctccaa ggacaggttc aggagggagc tggacggaat ccagtgcgag | 360 |
| attcaggcca cagaccccag cgagatgagc ctcgacatca tcagagccag agctcactga | 420 |

<210> SEQ ID NO 73
<211> LENGTH: 437
<212> TYPE: DNA
<213> ORGANISM: Oryza sativa

<400> SEQUENCE: 73

| atggcaatgg cttacaagat ggcgacggag gggatgaacg tgaaggagga gtgccagagg | 60 |
| tggttcatgg agatgaagtg gaagaaggtg caccggttcg tggtgtacaa gatcgacgag | 120 |
| cggtcgcgcg ccgtgctggt ggacaaggtg gcggcccccg gcgaagggta cgaggagctc | 180 |
| gtcgccgcgc tgcccaccga cgactgccgc tacgccgtct ccggactttt cgaatttcgt | 240 |
| caccgtcgac aactgccaga agaggcaaga tctttcttca tcgcctggtc accgaccgca | 300 |
| tcgaggataa gagccaagat tctgtacgcg acgtcgaagc aagggctgag gcgggtgctt | 360 |
| gacggggtcc actacgaggt gcaagccacg gactcctccg agatgggcta cgacgtcatc | 420 |
| cgaggccgcg ctcagtg | 437 |

<210> SEQ ID NO 74
<211> LENGTH: 420
<212> TYPE: DNA
<213> ORGANISM: Oryza sativa -continued

```
<400> SEQUENCE: 74
atgtcgaatt cggcgtcggg aatggccgtg tgtgacgaat gcaaactcaa gttcctggaa      60
cttaaggcga aaaggagctt ccgcttcatc gtgttcaaga tcaatgagaa ggtccagcag     120
gtggtggtgg acaggttggg gcagccgggt gagagctatg acgacttcac tgcctgctta     180
ccagcagatg agtgccgcta cgcggtattt gattttgact ttgtcactga tgaaaactgc     240
cagaagagca agatattctt catctcctgg gctcctgata catcaagggt gaggagcaag     300
atgctgtatg ctagctccaa ggatcggttc aagagggagc tggacggcat ccaggtggag     360
ctgcaggcca ctgacccgag tgagatgagc atggacatcg tcaagtcgcg agccctctga     420

<210> SEQ ID NO 75
<211> LENGTH: 453
<212> TYPE: DNA
<213> ORGANISM: Oryza sativa

<400> SEQUENCE: 75
atggcgaacg cgacgtcggg tgtggcggtg agcgaggagt gcaaggcgag gttccaggag      60
ctgagggcgg ggcgggccca caggttcgtg gtgttcaaga tcgacgacgc gatgcggcag     120
gtggtggtcg acagggtggg cccacgcgac gccggcttcg acgagctcac cgccagcctc     180
cccgccgacg gctgccgcta cgccgtgtac gaccacgact tcaccgtcag cgacgccacg     240
gccacggcgg ccgccggcga gggcggcgag gcgccgcgca gcaagatctt cttcgtgtcg     300
tggtcgccgg cggcggcgga cgtgaggagc aagatggtgt acgcgagctc caacgaaggg     360
ttcaagaagg agctcgacgg cgtccagatc gacctgcagg ccaccgaccc cagcgagctc     420
accctcgacg tgctcaagga ccacacctcc taa                                  453

<210> SEQ ID NO 76
<211> LENGTH: 419
<212> TYPE: DNA
<213> ORGANISM: Triticum aestivum

<400> SEQUENCE: 76
atggcgaacg cggcatcggg catggctgtg acgacgaat gcaagctcaa gttcctggag      60
ctgaaggcga agcgaaccca ccgcttcatc atctacaaga tagacgacaa gaagaagatg     120
gttgttgtgg agaaagtcgg cgagcctgcc ctgaactatg aggactttgc tgccagcctc     180
cccaccaatg aatgcagata cgcgatattc gactatgact tgtcaccga ggagaactgc      240
caaaagagca agatattctt cgtcgcatgg tctcctgaca ccgcacgcgt gaggagcaag     300
atgatctacg cgagctccaa ggagaggttc aagagggagc tcgacggcat ccaggtggag     360
ctgcaggcga cagacccgac cgaggtcggc tttgatgtga tccaaggccg tgccaactg     419

<210> SEQ ID NO 77
<211> LENGTH: 419
<212> TYPE: DNA
<213> ORGANISM: Triticum aestivum

<400> SEQUENCE: 77
atgtcgaatt ccgcgtcagg aatggccgtt tgcgacgaat gcaaactcaa gttccaggaa      60
ctcaaggcga agaggagctt ccgcttcatc gtgttcaaga tcaatgagaa ggtgcagcag     120
gtggtggtgg acagggtcgg ggaaaaaacc gagagctacg atgatttcac agcctgcttg     180
ccagctgacg agtgccgcta tgcagtgttt gattttgact tcgtcactga tgagaactgc     240
cagaagagca agatcttctt catctcttgg gctcctgaca catcaagggt gaggagcaag     300
```

```
atgctgtacg cgagctccaa ggaccgcttc aagagggagc tggacggcat ccaggtggag    360
ctacaggcga ccgacccgag cgagatgagc atggacatcg taaagggcg agccctctg     419
```

<210> SEQ ID NO 78
<211> LENGTH: 417
<212> TYPE: DNA
<213> ORGANISM: Triticum aestivum

<400> SEQUENCE: 78

```
atggcaaacg catcatccgg agctgggatc catgatgact gcaagctgag gtttgtggag    60
ctcaagtcca agaggatgca ccgcttcata acctacaggc tggagaacca gaaggaggtc   120
attgtggacc aaactgggga gcgcgaggcc acctatgagg acttcaccaa gaccctccct   180
gagaatgact gccgattcgc ggtgttcgac ttcgacttca ccaccccgga ggatgtgcca   240
aagagcagga tcttctatat cttctggtcc ccggacaccg caaaggtgag gagcaagatg   300
acgtacgcga gcaccaacga gaagttcaag gggaccctgg acggcatcca gatcgagatg   360
caggccactg accccagcga aatcagcctg gacgtgatca aggagcgcgc gcactaa      417
```

<210> SEQ ID NO 79
<211> LENGTH: 420
<212> TYPE: DNA
<213> ORGANISM: Triticum aestivum

<400> SEQUENCE: 79

```
atggcaaatg caagatcggg tgtcgctgtg aatgacgagt gcatgctgaa gtttggcgag    60
ctgcagtcga agaggctgca ccgcttcata acttacaaga tggatgacaa gttcaaggag   120
atagttgtgg accaggttgg ggatcgtgct accagctacg aggacttcac aaacagcctc   180
cctgagaatg actgccgata cgcaatctat gattttgact ttgtgactgc agaggatgtc   240
cagaagagca ggatattcta tatcctatgg tccccagact ctgccaaggt gaagagcaag   300
atgctttacg caagctctaa ccaaaagttc aagagtgggc tcaatggcat tcaggtggag   360
ctccaggcta cagatgcaag tgaaatcagc attgatcaga tcaaggatcg ggcacgctag   420
```

<210> SEQ ID NO 80
<211> LENGTH: 419
<212> TYPE: DNA
<213> ORGANISM: Triticum aestivum

<400> SEQUENCE: 80

```
atggcgaact cggcgtcggg catggccgtg agcgacgagt gcaagctcaa gttccaggag    60
ctcaaggcga agcggaccct ccggttcatc acgttcaaga tcaacgagca ctcgcagcag   120
gtggtggtgg accgggtggg gcaaccgggc gagacctacg ccgacttcac cgccaccatc   180
cccgccgacg agtgccgcta cgccgtcttc gactttgact tcgtcaccga cgagaactgc   240
cagaagagca agatcttctt catctcctgg tccccggaca cgtccagggt gaggagcaag   300
atgctgtacg cgagctccaa ggacaggttc aagagggagc tggacggcta ccaggtggag   360
ctgcaggcca ccgaacccag cgagatgacg ttggacatcg tcaaggccag agccctctg    419
```

<210> SEQ ID NO 81
<211> LENGTH: 432
<212> TYPE: DNA
<213> ORGANISM: Triticum aestivum

<400> SEQUENCE: 81

```
atggcaatgg cttacaagat ggcgacggag gggatgaaca tcaaggagga gtgcaagcgg    60
```

| | |
|---|---|
| tggttcacgg agatgaagtg gaagaaggtg caccgcttcg tggtctacaa gatcgacgag | 120 |
| cggacgcgcg ccgtgctggt ggacaaggtg ggcggcccccg gggagggggta cgacgagctc | 180 |
| gtcgccgcgc tgcccggcga cgactgccgc tacgccgtct tcgacttcga cttcgtctcc | 240 |
| gtcgacaact gccagaagag caagatcttc ttcatcgcat ggtcgccggc ggcgtcgagg | 300 |
| ataagggcca agatcctgta cgcgacgtcg aagcaaggcc tgcggcgggt gctggagggg | 360 |
| gtccactacg aggtgcaggc caccgagcgc tccgagatgg gcttcgacgt catcagagag | 420 |
| cgcgcgcaat ga | 432 |

<210> SEQ ID NO 82
<211> LENGTH: 437
<212> TYPE: DNA
<213> ORGANISM: Triticum aestivum

<400> SEQUENCE: 82

| | |
|---|---|
| atggccttca tgcgcacctc ctccaatgca tcctctggca tgggagttgc tcctgatatc | 60 |
| agggagacat tcctggagct tcagatgaag aaggcatttc gctatgttat cttcaaaatc | 120 |
| gaagaaaagc aaaaacaggt tgttgtggag aagacagggg ctacaactga gagttatgat | 180 |
| gatttcctgg cttgtctccc agaaaaggac tgcagatatg ccctttatga ttttgacttt | 240 |
| gttactgggg agaatgtgca gaaaagcaag attttcttca ttgcctggtc ccctgacaca | 300 |
| tcccgcatcc gcgccaagat gctgtactcc acctccaagg accgcatcaa gcaggagctc | 360 |
| gacgggttcc actacgagat ccaggcaact gacccgaccg aggtggagct cgatgtcctc | 420 |
| cgcgaccggg cgcacta | 437 |

<210> SEQ ID NO 83
<211> LENGTH: 419
<212> TYPE: DNA
<213> ORGANISM: Zea mays

<400> SEQUENCE: 83

| | |
|---|---|
| atggcaaacg cggcgtcagg gatggccgtg gacgacgact gcaagcgccg gttcctggag | 60 |
| ctcaaggcca agaggacgca ccgcttcatc atctacagga tcgacgagaa gaagaagatg | 120 |
| gtggtggtgg agcaggtggg caagcccgtg ctcggctacg acgacttcgc cgccagcctc | 180 |
| cccgccaacg agtgcaggta cgccatcttc gactacgact tcgtcaccga ggagaactgc | 240 |
| cagaagagca agatcttctt catcgcctgg tctcctgaca cggcgcgcgt gaggagcaag | 300 |
| atgatctacg ccagctccaa ggagaggttc aagcgggagc tggacggcat tcaggtggat | 360 |
| ctccaggcca ccgactccgc cgaggttggc cttgacgtca tccagggccg tgcaagctg | 419 |

<210> SEQ ID NO 84
<211> LENGTH: 419
<212> TYPE: DNA
<213> ORGANISM: Zea mays

<400> SEQUENCE: 84

| | |
|---|---|
| atggcgaact cgtcgtccgg ccttgcggtg aacgacgagt gcaaggtgaa gttccgggag | 60 |
| ctgaagtcgc ggcggagctt ccggttcatc gtgttcagga tcgacgacac ggacatggag | 120 |
| atcaaggtgg accgcctcgg cggaccgaac cagggctacg cgacttcac cgacagcctc | 180 |
| cccgccaacg agtgccgcta cgcgatctac gacctcgact tcaccaccat cgagaactgc | 240 |
| cagaagagca agatcttctt cttcctctgg tcccctgaca ctgcacgcac caggagcaag | 300 |
| atgctgtacg ccagctccaa ggacaggttc aggagggagc tggacggcat ccagtgcgag | 360 |

```
atccaggcca ccgacccag cgagatgagc ctcgacatcg tcaggagccg gaccaactg      419
```

<210> SEQ ID NO 85
<211> LENGTH: 419
<212> TYPE: DNA
<213> ORGANISM: Zea mays

<400> SEQUENCE: 85

```
atggcaaacg cgagatcggg tgtcgctgtg aatgacgagt gcatgctcaa gttcggcgag       60
ctgcagtcga agaggctgca ccgcttccta actttcaaga tggacgacaa gttcaaggag      120
atcgttgtgg accaggtcgg ggatcgcgct accagctacg aggacttcac aaacagcctc      180
cccgagaatg actgccgata cgcgatctat gatttcgact ttgtcactgc agaagatgtc      240
cagaagagca ggatcttcta tatcctatgg tccccatcct ccgccaaggt gaagagcaag      300
atgctttatg caagctcaaa ccaaaaattc aagagtgggc tcaatggcat tcaggtggaa      360
ctgcaggcta ctgatgcaag tgaaatcagc cttgatgaga tcaaggatcg ggctcgcta       419
```

<210> SEQ ID NO 86
<211> LENGTH: 431
<212> TYPE: DNA
<213> ORGANISM: Zea mays

<400> SEQUENCE: 86

```
atggcgatgg cgtacaagat ggcgacggag gggatgaacg tgaaggagga gtgccagcgc       60
tggttcatgg agatgaagtg gaagaaggtc accgcttcg tggtgtacaa gatcgacgag      120
cggtcgcgcg ccgtgctggt ggacaaggtg ggcggccccg ggaagggta cgaggagctc      180
gtggccgcgc tgcccggcga cgactgccgc tacgccgtct tcgacttcga cttcgtcacc      240
gtcgacaact gccagaagag caagatcttc ttcatcgcct ggtcaccggc ggcgtcgagg      300
atcagggcca agatcctgta cgcgacatcg aagcaaggcc tcggcggct gctggacggg      360
gtccactacg aggtgcaggc caccgacccc tctgagatgg gcttcgacgt catcagaggc      420
cgcgcgcaat g                                                          431
```

<210> SEQ ID NO 87
<211> LENGTH: 437
<212> TYPE: DNA
<213> ORGANISM: Zea mays

<400> SEQUENCE: 87

```
atggctttca tgcgctcccg ctcaaatgca tcttctggca tgggagttgc tcctaacatt       60
agggagacat tcgtcgagct tcaaatgaag aaggcattcc gatatgttat cttcaaaatc      120
gaagagaagc aaaagcaggt ggttgtggag aagacagggg ctactactga aagctatgat      180
gacttttggg cctctctccc agagaatgac tgccgatatg cgctgtatga ttttgatttt      240
gttactgggg agaatgtgca gaaaagcaag atttttcttca ttgcctggtc cccatcgaca      300
tcccgcatac gtgctaagat gctgtactcc acgtcgaagg accgcatcaa gtacgagctt      360
gacgggttcc actacgaaat ccaggcgacc gacccatcgg aggtggacat cgaggttctc      420
cgggagcggg ctcactg                                                    437
```

<210> SEQ ID NO 88
<211> LENGTH: 419
<212> TYPE: DNA
<213> ORGANISM: Zea mays

<400> SEQUENCE: 88

```
atgtcgaact cggcgtcggg aatggccgtc tgtgatgaat gcaagctcaa gttccaggag      60
ctcaaggcaa agaggagctt ccgcttcatc gtgttcaaga tcaacgagaa cgtgcagcag     120
gtggtggtgg acaggctagg ggagccaggc gagagctacg acgccttcac ggcctgcttc     180
cccgccaacg agtgccgcta cgccgtgttc gattttgact tcgtcactga cgagaactgc     240
cagaagagca agatcttctt tatctcttgg gccccggata catcgagggt gagaagcaag     300
atgctgtacg cgagctccaa ggaccggttc aagagggagc tggatggcat tcaggtggag     360
ctacaagcaa ccgacccgag cgaaatgagc atggacatcg tcaagtcgcg agccctctg      419
```

<210> SEQ ID NO 89
<211> LENGTH: 15
<212> TYPE: PRT
<213> ORGANISM: Artificial sequence
<220> FEATURE:
<223> OTHER INFORMATION: consensus sequence I
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid

<400> SEQUENCE: 89

Xaa Pro Xaa Xaa Xaa Cys Arg Xaa Xaa Xaa Xaa Asp Xaa Xaa Xaa
1               5                   10                  15

<210> SEQ ID NO 90
<211> LENGTH: 19
<212> TYPE: PRT
<213> ORGANISM: Artificial sequence
<220> FEATURE:
<223> OTHER INFORMATION: consensus sequence II
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(14)
<223> OTHER INFORMATION: Xaa can be any naturally occurring amino acid
<220> FEATURE:
<221> NAME/KEY: misc_feature
<222> LOCATION: (16)..(19)
<223> OTHER INFORMATION: Xaa can be any naturally occurring amino acid

<400> SEQUENCE: 90

Xaa Ile Xaa Xaa Xaa Xaa Trp Xaa Pro Xaa Xaa Xaa Xaa Xaa Arg Xaa
1               5                   10                  15

Xaa Xaa Xaa

<210> SEQ ID NO 91

```
<211> LENGTH: 18
<212> TYPE: PRT
<213> ORGANISM: Artificial sequence
<220> FEATURE:
<223> OTHER INFORMATION: consensus sequence III
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid

<400> SEQUENCE: 91

Arg Xaa Xaa Xaa Gly Xaa Xaa Xaa Glu Xaa Xaa Ala Thr Asp Xaa Xaa
1               5                   10                  15

Xaa Xaa

<210> SEQ ID NO 92
<211> LENGTH: 50
<212> TYPE: DNA
<213> ORGANISM: Artificial sequence
<220> FEATURE:
<223> OTHER INFORMATION: oligonucleotide

<400> SEQUENCE: 92
ggggacaagt ttgtacaaaa aagcaggctg tggatccccc gggctgcagg           50

<210> SEQ ID NO 93
<211> LENGTH: 50
<212> TYPE: DNA
<213> ORGANISM: Artificial sequence
<220> FEATURE:
<223> OTHER INFORMATION: oligonucleotide

<400> SEQUENCE: 93
ggggaccact ttgtacaaga aagctgggtt agggcgaatt gggtaccggg           50

<210> SEQ ID NO 94
<211> LENGTH: 42
<212> TYPE: DNA
<213> ORGANISM: Artificial sequence
<220> FEATURE:
<223> OTHER INFORMATION: oligonucleotide

<400> SEQUENCE: 94
tttaagcttg ccaccatggc aaacgcttca gcaggtgctg gg                   42

<210> SEQ ID NO 95
<211> LENGTH: 29
<212> TYPE: DNA
<213> ORGANISM: Artificial sequence
<220> FEATURE:
<223> OTHER INFORMATION: oligonucleotide

<400> SEQUENCE: 95
gttacgcgtc tagtgtgcgc gctccttga                                  29

<210> SEQ ID NO 96
<211> LENGTH: 55
```

-continued

```
<212> TYPE: DNA
<213> ORGANISM: Artificial sequence
<220> FEATURE:
<223> OTHER INFORMATION: primer

<400> SEQUENCE: 96
ggggacaagt tgtacaaaa aagcaggctg ccaccatggc aaacgcttca tcagg     55

<210> SEQ ID NO 97
<211> LENGTH: 48
<212> TYPE: DNA
<213> ORGANISM: Artificial sequence
<220> FEATURE:
<223> OTHER INFORMATION: primer

<400> SEQUENCE: 97
ggggaccact tgtacaaga aagctgggtt agtgtgcgcg ctccttga              48

<210> SEQ ID NO 98
<211> LENGTH: 33
<212> TYPE: DNA
<213> ORGANISM: Artificial sequence
<220> FEATURE:
<223> OTHER INFORMATION: primer

<400> SEQUENCE: 98
gcgaagcttg ccaccatggt gagcaagggc gag                             33

<210> SEQ ID NO 99
<211> LENGTH: 34
<212> TYPE: DNA
<213> ORGANISM: Artificial sequence
<220> FEATURE:
<223> OTHER INFORMATION: primer

<400> SEQUENCE: 99
aagacgcgtt tagaggcggg acttgtacag ctcg                            34

<210> SEQ ID NO 100
<211> LENGTH: 20
<212> TYPE: DNA
<213> ORGANISM: Artificial sequence
<220> FEATURE:
<223> OTHER INFORMATION: Primer

<400> SEQUENCE: 100
atggctaatg cagcatcagg                                            20

<210> SEQ ID NO 101
<211> LENGTH: 20
<212> TYPE: DNA
<213> ORGANISM: Artificial sequence
<220> FEATURE:
<223> OTHER INFORMATION: Primer

<400> SEQUENCE: 101
tcaattggct cggcttttga                                            20
```

METHOD FOR PRODUCTION OF TRANSGENIC PLANTS WITH INCREASED PATHOGENIC RESISTANCE BY ALTERING THE CONTENT AND/OR ACTIVITY OF ACTIN-DEPOLYMERISING FACTORS

RELATED APPLICATIONS

This application is a national stage application (under 35 U.S.C. 371) of PCT/EP2005/007688 filed Jul. 14, 2005, which claims benefit of German application 10 2004 036 456.7 filed Jul. 28, 2004.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence listing—13477-00007-US; date recorded: Jan. 26, 2007; size: 88 KB.

FIELD OF THE INVENTION

The present invention relates to a method for the production of transgenic plants and/or plant cells with increased pathogen resistance, wherein the transgenic plants or plant cells have a content and/or an activity which are/is altered as compared to the wild-type of at least one actin-depolymerizing factor (ADF). The present invention also relates to the use of nucleic acids coding for at least one ADF for producing transgenic plants or plant cells having increased pathogen resistance. Furthermore, the present invention relates to nucleic acid sequences coding for an ADF.

BACKGROUND OF THE INVENTION

Plant diseases caused by various pathogens, like for example viruses, bacteria, and fungi, may lead to substantial yield losses in growing cultivated plants. In order to control fungal diseases, nowadays fungicides are intensively used in agricultural production. Despite such means of control, a substantial portion of the possible yield is lost as a result of diseases. For a while now, there have been efforts to use cultivated plants having a natural resistance against significant fungal pathogens within the scope of integrated plant protection in order to reduce said yield deficits on the one hand and the use of fungicides in general on the other hand. Besides the classical cultivation methods for producing plants having a natural resistance, genetic engineering approaches, wherein resistances are supposed to be introduced selectively into significant cultivated plants, for example by means of introducing external resistance genes or manipulating endogenous gene expression in the plants, have been playing an increasingly important role in recent years.

Various mechanisms of resistance can be distinguished among the naturally occurring resistances. The so-called preformed "non-host" resistance describes the observation that an entire plant species is resistant to a specific pathogen. This phenomenon, which has not be understood yet, is probably based on structural or chemical properties of the plant species. Said properties can be, for example, the thickness of the cuticle, the presence of inhibitory substances, or the limited availability of nutrients.

In contrast, active mechanisms of resistance comprise such reactions and mechanisms which are triggered in the host plant by the attacking pathogen. Normally, the latter mechanism of resistance is of greater significance. However, it has to be noted that a clear distinction between the active resistance mechanisms and preformed resistance is not possible in all cases (Heitefuss, R. (2001), Naturwissenschaften, 88, 273-283).

Furthermore, differences with respect to the host/pathogen interaction have to be considered. For instance, obligate biotrophic pathogens require living host tissue. Thus, rapid cell death in the host, as is triggered by the so-called hypersensitive reaction (HR), can be a significant component in resistance against biotrophic pathogens. In contrast, perthotrophic pathogens cause cell death in the host, which is required for further development of the pathogen on the destroyed tissue.

It has to be emphasized that plants are resistant to a vast majority of potential pathogens, i.e. a specific plant species can only be attacked successfully by a limited number of pathogens. The failure of a successful attack by a non-pathogen is the result of the "non-host" resistance mentioned in the above.

The prerequisite for a successful attack of a plant species by a pathogen is to be seen in the so-called basic compatibility, which probably has developed as a result of co-evolution of the plant host and the potential pathogens. An attack will only be successful if the pathogen has factors allowing to overcome the basic resistance of the plant species.

Correspondingly, specific plant species and cultivars of a species, respectively, will be resistant or susceptible to a specific pathogen depending on their genotype. The different resistance mechanisms responsible for resistance or susceptibility of a plant species and its cultivars, respectively, to specific pathogens will be illustrated exemplarily for the mildew pathogen (*Blumeria graminis*), which infects various different grass species.

The mildew fungus as a species comprises various formae speciales, depending on whether the respective mildew fungus infects, for example, wheat or barley. In case barley is infected, it will be by *Blumeria graminis* f. sp. *hordei*, while in case wheat is infected, it will be by *Blumeria graminis* f. sp. *tritici*. Moreover, different races or pathotypes, to which different cultivars of the host species exhibit different resistances, can be identified within the different formae speciales.

In the following, the different resistance mechanisms of barley against mildew pathogens will be illustrated as this host/pathogen system has been best studied. The findings obtained therefrom can, however, also be transferred to other mildew/host systems, like for example the infection of wheat by mildew pathogens mentioned in the above. Other plant species infected by mildew pathogens comprise, for example, *Arabidopsis thaliana, Hordeum vulgare* (barley), *Triticum aestivum* and *T. durum* (wheat), *Secale cereale* (rye), *Avena sativa* (oat), *Lycopersicon* spp. (tomato), *Vitis* spp. (wine), *Cucumis* spp. (cucumber), *Cucurbita* spp. (pumpkin), *Pisum* spp. (pea), *Prunus* spp. (peach), *Solanum tuberosum* (potato), *Rosa* spp. (rose), *Fragaria ananassa* (strawberry), *Rhododendron* spp. (azalea), *Malus domestica* (apple), and *Nicotiana tabacum* (tobacco).

*Blumeria graminis* f. sp. *hordei* exclusively attacks the epidermal cell layer of barley leaves. The fungus mechanically and enzymatically penetrates the cell wall via a penetration peg (i.e. penetration hypha), which consists of conidia, i.e. asexually formed spores. A successful infection of barley leaves is achieved if the haustorium, which is the fungal organ of nutrition, has developed.

There are two distinct genetic mechanisms to be distinguished, which render barley resistant to mildew. The first mechanism is based on the so-called "gene-by-gene" concept. In this mechanism, resistance is achieved in that a dominantly acting resistance gene renders the plants resistant to only such fungal isolates which carry the corresponding avirulence gene. In most cases, this so-called race-specific resistance, wherein a barley cultivar is resistant only to selected mildew isolates, is characterized by the hypersensitive reaction (HR), i.e. the host cells of the infection site die off (Heitefuss, R., vide supra).

In contrast to this, the second mechanism imparts a broad spectrum resistance to all known isolates of a forma specialis of the mildew fungus and is characterized by the absence of the so-called Mlo wild-type gene. Mlo is a presumably negative regulator of the pathogen defense (Devoto, A. et al. (1999), *J. Biol. Chem.*, 274, 34993-35004). The function of this mechanism is also depending on at least two further genes, Ror1 and Ror2 (Freialdenhoven, A. et al. (1996), *Plant Cell*, 8, 5-14). Resistance or incompatibility, as is mediated by recessive mlo resistance alleles, is generally not characterized by the occurrence of an HR. Rather, the only observable cellular effect, which becomes visible during defense of the plant against the attacking fungus, is the formation of a subcellular cell wall apposition, which is referred to as papilla and forms directly below the fungal penetration hypha, the so-called appressorium. In this type of non-race-specific resistance, which is mediated by recessive mlo alleles, the penetration attempts of the fungus are inhibited at the stage of papilla formation, i.e. a haustorium, which is essential for establishing an efficient infection, is not even developed.

Pathogen-induced papilla formation is also observed in other Gramineae species, which indicates that non-race-specific resistance, as is known for the barley/mildew system, also occurs in other plant species. Another sign for this is the fact that Mlo proteins occur in other species, like for example in *Arabidopsis thaliana* or *Oryza sativa*.

As in case of non-race-specific resistance a barley cultivar is resistant to various different mildew isolates or several barley cultivars are resistant to various different mildew isolates of *Blumeria graminis* f. sp. *hordei* (and as, due to the functional equivalence of the Mlo proteins in the various plant species in which they occur, this probably also applies to said plants), these plants have considerable advantages and are of particular interest as compared to those plants having only race-specific resistance. There is thus a need for further plants or plant cells having such non-race-specific resistance to fungal pathogens like, for example, mildew.

BRIEF SUMMARY OF THE INVENTION

It is a problem underlying the present invention to provide transgenic plants or plant cells having an increased resistance against different plant pathogens. It is furthermore a problem underlying the present invention to provide plants or plant cells having a race-unspecific resistance to different fungal pathogens, like for example mildew. It is also a problem underlying the present invention to provide transgenic barley plants or barley plant cells having a non-race-specific sequence to fungal pathogens, such as the mildew pathogen. Furthermore, it is a problem of the present invention to provide methods allowing the production of transgenic plants or plant cells mentioned in the above with an increased (non-race-specific) resistance to plant pathogens, like for example mildew.

The features of the independent claims serve for solving these and further problems as become obvious from the description.

Preferred embodiments of the present invention are defined by the features of the subclaims.

In essence, the mentioned problems of the present invention are solved by providing a method for the production of transgenic plants with increased pathogen resistance, characterized in that the content and/or the activity of at least one actin-depolymerizing factor (ADF) is altered as compared to the corresponding wild-type.

BRIEF DESCRIPTION OF THE DRAWINGS

FIG. 1 shows a sequence alignment of HvADF3 (SEQ ID NO: 1) as well as different ADFs from *Arabidopsis thaliana* (see also Table 5; At1g01750 (SEQ ID NO: 18), At4g00680 (SEQ ID NO: 16), At5g52360 (SEQ ID NO: 15), At4g25590 (SEQ ID NO: 19), At5g59890 (SEQ ID NO: 12), At3g46010 (SEQ ID NO: 9), At3g46000 (SEQ ID NO: 10), At5g59880 (SEQ ID NO: 11), At3g45990 (SEQ ID NO: 20), At4g34970 (SEQ ID NO: 17), At2g16700 (SEQ ID NO: 13), and At2g31200 (SEQ ID NO: 14)).

FIG. 7 shows the movement of GFP-labeled peroxisomes in individual epidermal leaf cells from barley. A plasmid, which coded a GFP variant having a C-terminal peroxisomal targeting sequence, was expressed either alone (A, control) or together with a plasmid, which expresses a "constitutively active" variant of HvADF3 bearing an $S^6A$ amino acid substitution (B). While GFP-labeled peroxisomes moved constantly within the bombarded cells in the control transfections (A), the peroxisomes were slowed down in case of co-expression of the constitutively active variant of HvADF3 (B) and finally aggregated.

FIG. 8 shows that the overexpression of HvADF3 inhibits the development of the fungus. Epidermal leaf cells from barley were transfected with GUS (β-glucuronidase) reporter plasmids and a plasmid effecting the ectopic expression of a constitutively active variant of HvADF3 (bearing an $S^6A$ amino acid substitution). 4 hours after bombardment, the cells were inoculated with Bgh conidiospores and 72 hours after inoculation the leaves were stained for GUS activity and fungal structures. A, B, the fungal development of a transfected epidermal leaf cell. C, the fungal development of a successfully infected stomata cell.

DETAILED DESCRIPTION OF THE INVENTION

Figure 2:
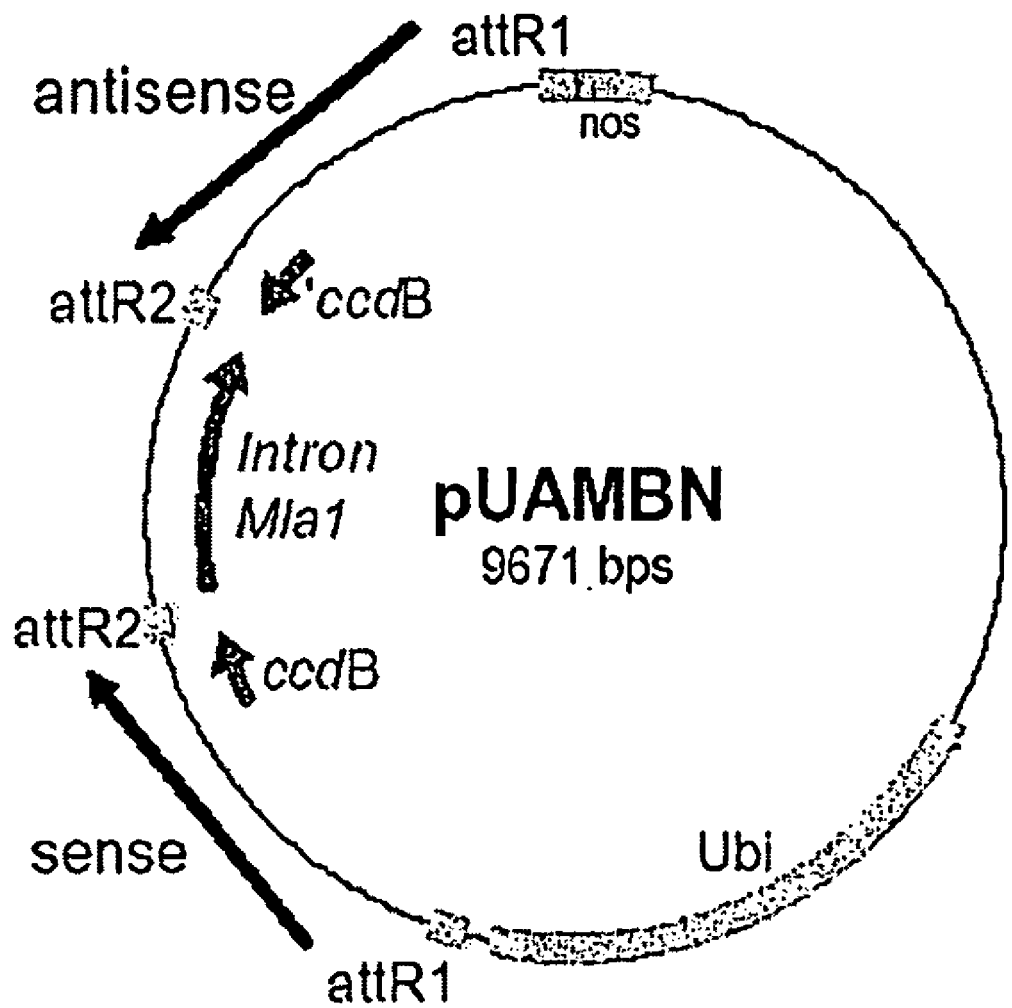
FIG. 2 shows the vector pUAMBN, which was used for the dsRNAi-based silencing in epidermal cells from barley. Ubi, maize polyubiquitin promoter; attR1 and attR2, Gateway recombination sites; ecdB, negative selection marker; nos, *Agrobacterium tumefaciens* nopaline synthase transcriptional terminator.

As has been illustrated in the above, non-race-specific resistance in barley and other *Gramineae* is mediated by recessive mlo alleles. Thus, for a long time, there have been efforts to identify other genes interacting with the Mlo gene. Herein, further genes, as being Ror1 and Ror2, genetically interacting with the Mlo gene could be identified (Freialdenhoven et al., vide supra) by mutagenesis screening. A general problem with the identification of further genes, which interact with the Mlo gene and therefore could also be used to produce non-race-specific resistance by means of corresponding manipulation, is that, depending on the screening method by means of which modified infection types can be evidenced, and with respect to the genomic redundancy of barley, the mutagenesis screening methods used are not always sensitive enough to identify further genes of the mlo mediated resistance mechanism.

With the aid of a new screening approach according to the present invention, wherein epidermally expressed genes are silenced by RNA interference (RNAi), it has for the first time been achieved to identify another gene genetically interacting with Mlo in addition to the already mentioned genes Ror1 and Ror2. Said gene is the actin-depolymerizing factor 3 (ADF3) from barley, whose amino acid sequence is given in SEQ ID No. 1.

Within the scope of the present invention, it could also surprisingly be shown that over-expression or repression of said actin-depolymerizing factor mediates a non-race-specific broad spectrum resistance of barley against mildew.

The transgenic plants or plant cells from barley, in which the content and/or the activity of ADF3 is altered as compared to the wild-type, thus have an increased non-race-specific resistance to the mildew pathogen.

It can thus be assumed that by altering the content and/or the activity of ADFs as compared to the wild-type transgenic plants or plant cells of different plant species can be produced, which are characterized by an increased resistance to plant pathogens and, in particular, to fungal pathogens like mildew. In particular, this should apply in cases where the plant pathogens have to perform a functionally relevant interaction with the actin cytoskeleton in order to establish an efficient infection (see below).

Thus, an object of the present invention is an isolated nucleic acid molecule coding for the ADF3 from barley identified in SEQ ID No. 1. Nucleic acid molecules coding for functionally equivalent parts of the ADF3 from barley identified with SEQ ID No. 1, coding for mutants of the ADF3 from barley identified in SEQ ID No. 1, or nucleic acid molecules hybridizing under stringent conditions with the previously mentioned nucleic acid molecules are also objects of the present invention.

Further objects of the present invention are proteins or protein fragments which are coded by the previously mentioned nucleic acid molecules.

A method for producing transgenic plants or plant cells having, as compared to the wild-type, an increased pathogen resistance and/or an altered activity of at least one ADF is also an object of the present invention.

A further object of the present invention is a method for the production of transgenic plants or plant cells with increased pathogen resistance, in which the expression of at least one ADF is effected by transferring the previously mentioned nucleic acid sequences or such nucleic acid sequences being homologous to ADF3 from barley identified in SEQ ID NO. 1 to plants or plant cells.

The present invention has also as its objects methods for the production of transgenic plants or plant cells with increased pathogen resistance, in which the content and/or the activity of at least one endogenous ADF is regulated up or down.

A further object of the present invention is a method for producing transgenic plants or plant cells with increased pathogen resistance, in which the activity of at least one endogenous ADF is reduced by transferring nucleic acid molecules coding for non-functional homologs, or for parts thereof, of the ADF3 from barley with SEQ ID No. 1.

A further object of the present invention is a method for producing transgenic plants or plant cells with increased pathogen resistance, in which antibodies specific for ADFs and possibly inhibiting their function are expressed in the cell.

A further object of the present invention are methods for producing transgenic plants or plant cells having increased pathogen resistance, in which the post-translational modification state of at least one overexpressed and/or endogenous ADF is altered.

Also an object of the present invention are methods for producing transgenic plants or plant cells with increased pathogen resistance, in which the expression of at least one ADF is silenced by methods like, for example, antisense methods, post-transcriptional gene silencing (PTGS), virus-induced gene silencing (VIGS), RNA interference (RNAi), ribonuclease P constructs, hammerhead ribozyme constructs, or homologous recombination.

Object of the present invention are also transgenic plants or plant cells having an increased pathogen resistance and having an altered content and/or an altered activity of at least one ADF, as compared to the wild-type.

Object of the present invention are also transgenic plants or plant cells produced according to one of the methods according to the present invention and having increased pathogen resistances in comparison to the wild-type.

A further object of the present invention is the use of nucleic acids coding for functional or non-functional ADFs, or for parts thereof, from different organisms for producing transgenic plants or plant cells having increased pathogen resistance.

The use of the nucleic acid sequences described in the present invention for the methods described or for producing the previously mentioned transgenic plants or plant cells is also an object of the present invention.

According to the present invention, "pathogen resistance" denotes reducing or attenuating disease symptoms of a plant as a result of attack by a pathogen. While said symptoms can be manifold, they preferably comprise such symptoms directly or indirectly leading to impairment of plant quality, yield quantity, or suitability for use as feed or food, or, however, impeding sowing, cultivation, harvest, or processing of the crop.

According to the present invention, the term "increased pathogen resistance" is understood to denote that the transgenic plants or plant cells of the present invention are infected less severely and/or less frequently by plant pathogens. Here, the term "increased pathogen resistance" also includes a so-called transient pathogen resistance, i.e. the transgenic plants or plant cells of the present invention exhibit an increased pathogen resistance compared to the corresponding wild-type only for a specific period of time.

Herein, the reduced frequency and the reduced extent of pathogen infection, respectively, on the transgenic plants or plant cells according to the present invention is determined as compared to the corresponding wild-type. According to the present invention, an increase in resistance is preferred in the sense that an infection of the plant by the pathogen occurs less frequently or less severely by at least 5%, preferably by at least 20%, also preferably by at least 50%, 60% or 70%, especially preferably by at least 80%, 90% or 100%, also especially preferably by the factor 5, particularly preferably by at least the factor 10, also particularly preferably by at least the factor 50, and more preferably by at least the factor 100, and most preferably by at least the factor 1000, as compared to the wild-type.

According to the present invention, the term "plant pathogens" is understood to denote such plant pathogens, which have to interact with the actin cytoskeleton of the plant in order to establish efficient infection. Preferably, the term "plant pathogens" comprises fungal pathogens.

Preferably, fungal pathogens or fungal-like pathogens (like for example *Chromista*) are from the group comprising Plasmodiophoramycetes, Oomycetes, Ascomycetes, Chytridiomycetes, Zygomycetes, Basidiomycetes, and Deuteromycetes (Fungi imperfecti). The pathogens listed in Tables 1 and 2 as well as the diseases associated therewith are to be mentioned in an exemplary, yet not limiting manner.

TABLE 1

Fungal plant diseases

| Disease | Pathogen |
| --- | --- |
| Leaf rust | *Puccinia recondita* |
| Yellow rust | *P. striiformis* |
| Powdery mildew | *Erysiphe graminis/Blumeria graminis* |
| Glume blotch | *Septoria nodorum* |
| Septoria tritici leaf spot | *Septoria tritici* |
| Head fusarioses | *Fusarium* spp. |
| Stem break | *Pseudocercosporella herpotrichoides* |
| Loose smut (*Ustilago nuda*) | *Ustilago* spp. |
| Common bunt | *Tilletia caries* |
| Take-all patch | *Gaeumannomyces graminis* |
| Anthracnose leaf blight | *Colletotrichum graminicola* (telomorph: *Glomerella graminicola* |
| Anthracnose stalk rot | Politis); *Glomerella tucumanensis* (anamorph: *Glomerella falcatum* Went) |
| *Aspergillus* ear and kernel rot | *Aspergillus flavus* |
| Banded leaf and sheath spot ("Wurzeltöter") | *Rhizoctonia solani* Kuhn = *Rhizoctonia microsclerotia* J. Matz (telomorph: *Thanatephorus cucumeris*) |
| Black bundle disease | *Acremonium strictum* W. Gams = *Cephalosporium acremonium* Auct. non Corda |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata, C. eragrostidis,* = *C. maculans* (telomorph: *Cochliobolus eragrostidis*), *Curvularia inaequalis, C. intermedia* (telomorph: *Cochliobolus intermedius*), *Curvularia lunata* (telomorph: *Cochliobolus lunatus*), *Curvularia pallescens* (telomorph: *Cochliobolus pallescens*), *Curvularia senegalensis, C. tuberculata* (telomorph: *Cochliobolus tuberculatus*) |
| *Didymella* leaf spot | *Didymella exitalis* |
| *Diplodia* ear rot and stalk rot | *Diplodia frumenti* (telomorph: *Botryosphaeria festucae*) |
| *Diplodia* ear rot, stalk rot, seed rot and seedling blight | *Diplodia maydis* = *Stenocarpella maydis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Java downy mildew | *Peronosclerospora maydis* = *Sclerospora maydis* |
| Philippine downy mildew | *Peronosclerospora philippinensis* = *Sclerospora philippinensis* |
| Sorghum downy mildew | *Peronosclerospora sorghi* = *Sclerospora sorghi* |
| Spontaneum downy mildew | *Peronosclerospora spontanea* = *Sclerospora spontanea* |
| Sugarcane downy mildew | *Peronosclerospora sacchari* = *Sclerospora sacchari* |
| Dry ear rot (cob, kernel and stalk rot) | *Nigrospora oryzae* (telomorph: *Khuskia oryzae*) |
| Ear rots, minor | *Alternaria alternata* = *A. tenuis, Aspergillus glaucus, A. niger, Aspergillus* spp., *Botrytis cinerea* (telomorph: *Botryotinia fuckeliana*), *Cunninghamella* sp., *Curvularia pallescens, Doratomyces stemonitis* = *Cephalotrichum stemonitis, Fusarium culmorum, Gonatobotrys simplex, Pithomyces maydicus, Rhizopus microsporus* Tiegh., *R. stolonifer* = *R. nigricans, Scopulariopsis brumptii* |

TABLE 1-continued

Fungal plant diseases

| Disease | Pathogen |
|---|---|
| Ergot (horse's tooth) | *Claviceps gigantea* (anamorph: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* (telomorph: *Gibberella fujikuroi*) |
| *Fusarium* stalk rot, seedling root rot | *Fusarium avenaceum* (telomorph: *Gibberella avenacea*) |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (*Cercospora* leaf spot) | *Cercospora sorghi* = *C. sorghi* var. *maydis*, *C. zeae-maydis* |
| *Helminthosporium* root rot | *Exserohilum pedicellatum* = *Helminthosporium pedicellatum* (telomorph: *Setosphaeria pedicellata*) |
| *Hormodendrum* ear rot (*Cladosporium* rot) | *Cladosporium cladosporioides* = *Hormodendrum cladosporioides*, *C. herbarum* (telomorph: *Mycosphaerella tassiana*) |
| *Hyalothyridium* leaf spot | *Hyalothyridium maydis* |
| Late wilt | *Cephalosporium maydis* |
| Leaf spots, minor | *Alternaria alternata*, *Ascochyta maydis*, *A. tritici*, *A. zeicola*, *Bipolaris victoriae* = *Helminthosporium victoriae* (telomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (telomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |
| *Penicillium* ear rot (blue eye, blue mold) | *Penicillium* spp., *P. chrysogenum*, *P. expansum*, *P. oxalicum* |
| *Phaeocytostroma* stalk rot and root rot | *Phaeocytostroma ambiguum*, = *Phaeocytosporella zeae* |
| *Phaeosphaeria* leaf spot | *Phaeosphaeria maydis* = *Sphaerulina maydis* |
| *Physalospora* ear rot (*Botryosphaeria* ear rot) | *Botryosphaeria festucae* = *Physalospora zeicola* (anamorph: *Diplodia frumenti*) |
| Purple leaf sheath | Hemiparasitic bacteria and fungi |
| *Pyrenochaeta* stalk rot and root rot | *Phoma terrestris* = *Pyrenochaeta terrestris* |
| *Pythium* root rot | *Pythium* spp., *P. arrhenomanes*, *P. graminicola* |
| *Pythium* stalk rot | *Pythium aphanidermatum* = *P. butleri* L. |
| Red kernel disease (ear mold, leaf and seed rot) | *Epicoccum nigrum* |
| *Rhizoctonia* ear rot (sclerotial rot) | *Rhizoctonia zeae* (telomorph: *Waitea circinata*) |
| *Rhizoctonia* root rot and stalk rot | *Rhizoctonia solani*, *Rhizoctonia zeae* |
| Root rots, minor | *Alternaria alternata*, *Cercospora sorghi*, *Dictochaeta fertilis*, *Fusarium acuminatum* (telomorph: *Gibberella acuminata*), *F. equiseti* (telomorph: *G. intricans*), *F. oxysporum*, *F. pallidoroseum*, *F. poae*, *F. roseum*, *G. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| *Rostratum* leaf spot (*Helminthosporium* leaf disease, ear and stalk rot) | *Setosphaeria rostrata*, (anamorph: *Exserohilum rostratum* = He/minthosporium *rostratum*) |
| Rust, common corn | *Puccinia sorghi* |
| Rust, southern corn | *Puccinia polysora* |
| Rust, tropical corn | *Physopella pallescens*, *P. zeae* = *Angiopsora zeae* |
| *Sclerotium* ear rot (southern blight) | *Sclerotium rolfsii* Sacc. (telomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, |

TABLE 1-continued

Fungal plant diseases

| Disease | Pathogen |
|---|---|
| | *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Black leg disease | *Gaeumannomyces graminis* |
| Shuck rot | *Myrothecium gramineum* |
| Silage mold | *Monascus purpureus*, *M ruber* |
| Smut, common | *Ustilago zeae* = *U. maydis* |
| Smut, false | *Ustilaginoidea virens* |
| Smut, head | *Sphacelotheca reiliana* = *Sporisorium holcisorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots, minor | *Cercospora sorghi*, *Fusarium episphaeria*, *F. merismoides*, *F. oxysporum* Schlechtend, *F. poae*, *F. roseum*, *F. solani* (telomorph: *Nectria haematococca*), *F. tricinctum*, *Mariannaea elegans*, *Mucor* sp., *Rhopographus zeae*, *Spicaria* sp. |
| Storage rots | *Aspergillus* spp., *Penicillium* spp. and other fungi |
| Tar spot | *Phyllachora maydis* |
| *Trichoderma* ear rot and root rot | *Trichoderma viride* = *T. lignorum* telomorph: *Hypocrea* sp. |
| White ear rot, root and stalk rot | *Stenocarpella maydis* = *Diplodia zeae* |
| Yellow leaf blight | *Ascochyta ischaemi*, *Phyllosticta maydis* (telomorph: *Mycosphaerella zeae-maydis*) |
| Zonate leaf spot | *Gloeocercospora sorghi* |

Particularly preferred are:

Plasmodiophoromycetes like *Plasmodiophora brassicae* (clubroot of crucifers), *Spongospora subterranea* (powdery scab of potato tubers), *Polymyxa graminis* (root disease of cereals and grasses), Oomycetes like *Bremia lactucae* (downy mildew of lettuce), *Peronospora* (downy mildew) of snapdragon (*P. antirrhini*), onion (*P. destructor*), spinach (*P. effusa*), soy bean (*P. manchurica*), tobacco ("blue mold", *P. tabacina*) alfalfa and clover (*P. trifolium*), *Pseudoperonospora humuli* (downy mildew of hop), *Plasmopara* (downy mildew) of grapes (*P. viticola*) and sun flower (*P. halstedii*), *Sclerophtohra macrospora* (downy mildew of cereals and grasses), *Pythium* (seed rot, seedling damping-off, and root rot and all types of plants, for example black root disease of beet caused by *P. debaryanum*), *Phytophthora infestans* (potato light blight, tomato late blight, etc.), *Albugo* spec. (white rust on cruciferous plants)

Ascomycetes like *Microdochium nivale* (snow mold of rye and wheat), *Fusarium graminearum, Fusarium culmorum* (head blight, in particular of wheat), *Fusarium oxysporum* (fusarium wilt of tomato), *Blumeria graminis* (powdery mildew of barley (f. sp. *hordei*) and wheat (f. sp. *tritici*)), *Erysiphe pisi* (pea mildew), *Nectria galligena* (*Nectria* canker of fruit trees), *Unicnula necator* (grapevine powdery mildew), *Pseudopeziza tracheiphila* (grapevine red fire disease), *Claviceps purpurea* (ergot on, for example, rye and grasses), *Gaeumannomyces graminis* (black leg disease of wheat, rye and, inter alia, grasses), *Magnaporthe grisea* (rice blast disease), *Pyrenophora graminea* (leaf stripe disease of barley), *Pyrenophora teres* (net blotch disease of barley), *Pyrenophora tritici-repentis* (tan spot disease (Septoria leaf spot) of wheat), *Venturia inaequalis* (apple scab disease), *Sclerotinia sclerotium* (white mold, stem canker of rape), *Pseudopeziza medicaginis* (leaf spot diseases of lucerne, white and red clover).

Basidiomycetes like *Typhula incarnata* (typhula snow mold of barley, rye, and wheat), *Ustilago maydis* (corn smut), *Ustilago nuda* (loose smut of barley), *Ustilago tritici* (loose smut of wheat and spelt), *Ustilago avenae* (loose smut of oat), *Rhizoctonia solani* (taproot lesions of potatoes), *Sphacelotheca* spp. (head smut of sorghum), *Melampsora lini* (rust of flax), *Puccinia graminis* (stem rust of wheat, barley, rye, oat), *Puccinia recondita* (brown rust of wheat), *Puccinia dispersa* (brown rust of rye), *Puccinia hordei* (brown rust of barley), *Puccinia coronata* (crown rust of oat), *Puccinia striiformis* (yellow rust of wheat, barley, rye, and various grasses), *Uromyces appendiculatus* (bean rust), *Sclerotium rolfsii* (root and stem rots of many plants).

Deuteromycetes (Fungi imperfecti) like *Septoria nodorum* (glume blotch) of wheat (Septoria tritici), *Pseudocercosporella herpotrichoides* (stem break disease in wheat, barley, rye), *Rynchosporium secalis* (scald disease in rye and barley), *Alternaria solani* (early blight of potato and tomato), *Phoma betae* (black rot of beet), *Cercospora beticola* (Cercospora leaf spot of beet), *Alternaria brassicae* (dark leaf spot of rape, cabbage and other cruciferous plants), *Verticillium dahliae* (Verticillium wilt and stalk rot of rape), *Colletotrichum lindemuthianum* (bean anthracnose), *Phoma lingam*—phoma stem canker (black leg disease of cabbage; crown and stem canker of rape), *Botrytis cinerea* (gray mold diseases of grapevine, strawberry, tomato, hop, etc.).

Likewise preferred are: *Phytophthora infestans* (late blight of tomato, root and foot rot of tomato, etc.), *Microdochium nivale* (formerly *Fusarium nivale*; snow mold of rye and wheat), *Fusarium graminearum, Fusarium culmorum* (head blight of wheat), *Fusarium oxysporum* (Fusarium wilt of tomato), *Blumeria graminis* (powdery mildew of barley (f. sp. *hordei*) and wheat (f. sp. *tritici*)), *Magnaporthe grisea* (rice blast disease), *Sclerotinia sclerotium* (white mold, stem canker of rape), *Septoria nodorum* and *Septoria tritici* (glume blotch of wheat), *Alternaria brassicae* (dark leaf spot of rape, cabbage and other cruciferous plants), *Phoma lingam* (phoma stem canker, black leg disease of cabbage; crown and stem canker of rape).

The pathogens listed in Table 2 as well as the diseases associated therewith are to be mentioned as bacterial pathogens in an exemplary, yet not limiting manner.

TABLE 2

Bacterial diseases

| Disease | Pathogen |
| --- | --- |
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora*, *Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis* = *Corynebacterium michiganense* pv.andnebraskense |
| Holcus spot | *Pseudomonas syringae* pv. *syringae* |

TABLE 2-continued

Bacterial diseases

| Disease | Pathogen |
| --- | --- |
| Purple leaf sheath | *Hemiparasitic bacteria* |
| Seed rot-seedling blight | *Bacillus subtilis* |
| Stewart's disease (bacterial wilt) | *Pantoea stewartii* = *Erwinia stewartii* |
| Corn stunt (achapparramiento, maize stunt, Mesa Central or Rio Grande maize stunt) | *Spiroplasma kunkelii* |

Particularly preferably, the transgenic plants produced according to the present invention are resistant to the following pathogenic bacteria:

*Corynebacterium sepedonicum* (bacterial ring rot of potato), *Erwinia carotovora* (black leg rot of potato), *Erwinia amylovora* (fire blight of pear, apple, quince), *Streptomyces scabies* (common scab of potato), *Pseudomonas syringae* pv. *tabaci* (wild fire disease of tobacco), *Pseudomonas syringae* pv. *phaseolicola* (halo blight disease of dwarf bean), *Pseudomonas syringae* pv. tomato ("bacterial speck" of tomato), *Xanthomonas campestris* pv. *malvacearum* (angular leaf spot of cotton), and *Xanthomonas campestris* pv. *oryzae* (bacterial blight of rice and other grasses).

The term "viral pathogens" includes all plant viruses, like for example tobacco or cucumber mosaic virus, ringspot virus, necrosis virus, maize dwarf mosaic virus, etc.

The pathogens listed in Table 3 as well as the diseases associated therewith are to be mentioned as viral pathogens in an exemplary, yet not limiting manner.

TABLE 3

Viral diseases

| Disease | Pathogen |
| --- | --- |
| American wheat striate (wheat striate mosaic) | American wheat striate mosaic virus (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle | Cereal chlorotic mottle virus (CCMV) |
| Corn chlorotic vein banding (Braizilian maize mosaic) | Corn chlorotic vein banding virus (CCVBV) |
| Corn lethal necrosis | Virus complex from Maize chlorotic mottle virus (MCMV) and Maize dwarf mosaic virus (MDMV) A or B or Wheat streak mosaic virus(WSMV) |
| Cucumber mosaic | Cucumber mosaic virus (CMV) |
| Cynodon chlorotic streak | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line | Maize line virus (MLV) |
| Maize mosaic (corn leaf stripe, enanismo rayado) | Maize mosaic virus (MMV) |
| Maize mottle and chlorotic stunt | Maize mottle and chlorotic stunt virus |
| Maize pellucid ringspot | Maize pellucid ringspot virus (MPRV) |
| Maize raya gruesa | Maize raya gruesa virus (MRGV) |
| maize rayado fino (fine striping disease) | Maize rayado fino virus (MRFV) |
| Maize red leaf and red stripe | Mollicute |
| Maize red stripe | Maize red stripe virus (MRSV) |
| Maize ring mottle | Maize ring mottle virus (MRMV) |
| Maize rio IV | Maize rio cuarto virus (MRCV) |
| Maize rough dwarf (nanismo ruvido) | Maize rough dwarf virus (MRDV) (Cereal tillering disease virus) |
| Maize sterile stunt | Maize sterile stunt virus (strains of barley yellow striate virus) |

TABLE 3-continued

Viral diseases

| Disease | Pathogen |
| --- | --- |
| Maize streak | Maize streak virus (MSV) |
| Maize stripe (maize chlorotic stripe, maize hoja blanca) | Maize stripe virus |
| Maize stunting | Maize stunting virus |
| Maize tassel abortion | Maize tassel abortion virus (MTAV) |
| Maize vein enation | Maize vein enation virus (MVEV) |
| Maize wallaby ear | Maize wallaby ear virus (MWEV) |
| Maize white leaf | Maize white leaf virus |
| Maize white line mosaic | Maize white line mosaic virus (MWLMV) |
| Millet red leaf | Millet red leaf virus (MRLV) |
| Northern cereal mosaic | Northern cereal mosaic virus (NCMV) |
| Oat pseudorosette (zakuklivanie) | Oat pseudorosette virus |
| Oat sterile dwarf | Oat sterile dwarf virus (OSDV) |
| Rice black-streaked dwarf | Rice black-streaked dwarf virus (RBSDV) |
| Rice stripe | Rice stripe virus (RSV) |
| Sorghum mosaic | Sorghum mosaic virus (SrMV) (also: sugarcane mosaic virus (SCMV) strains H, I and M) |
| Sugarcane Fiji disease | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Wheat spot mosaic | Wheat spot mosaic virus (WSMV) |

The plants and plant cells according to the present invention can also be resistant to animal pests like insects and nematodes. Insects, like for example beetles, caterpillars, lice, or mites are to be mentioned in an exemplary, yet not limiting manner.

Preferably, the plants according to the present invention are resistant to insects of the species of *Coleoptera, Diptera, Hymenoptera, Lepidoptera*, Mallophaga, *Homoptera*, Hemiptera, Orthoptera, Thysanoptera. *Dermaptera, Isoptera*, Anoplura, *Siphonaptera, Trichoptera*, etc. Insects of the following species are particularly preferred: *Coleoptera* and *Lepidoptera*, like, for example, the European corn borer (ECB), *Diabrotica barberi* (Northern corn rootworm), *Diabrotica undecimpunctata* (Southern corn rootworm), *Diabrotica virgifera* (Western corn rootworm), *Agrotis ipsilon* (black cutworm), *Crymodes devastator* (glassy cutworm), *Feltia ducens* (dingy cutworm), *Agrotis gladiaria* (claybacked cutworm), *Melanotus* spp., *Aeolus mellillus* (wireworm), *Aeolus mancus* (wheat wireworm), *Horistonotus uhlerii* (sand wireworm), *Sphenophorus maidis* (maize billbug), *Sphenophorus zeae* (timothy billbug), *Sphenophorus parvulus* (bluegrass billbug), *Sphenophorus callosus* (southern corn billbug), *Phyllogphaga* spp. (white grubs), *Anuraphis maidiradicis* (corn root aphid), *Delia platura* (seedcorn maggot), *Colaspis brunnea* (grape *colaspis*), *Stenolophus lecontei* (seedcorn beetle), and *Clivinia impressifrons* (lender seedcorn beetle).

Furthermore, there are to be mentioned: the cereal leaf beetle (*Oulema melanopus*), the frit fly (*Oscinella frit*), wireworms (*Agrotis lineatus*), and aphids (like for example the bird cherry-oat aphid *Rhopalosiphum padi*, the grain aphid *Sitobion avenae*).

The pathogens listed in Table 4 as well as the diseases associated therewith are to be mentioned as nematode pests in an exemplary, yet not limiting manner.

TABLE 4

Parasitic nematodes

| Damage | Pathogenic nematode |
| --- | --- |
| Awl | *Dolichodorus* spp., *D. heterocephalus* |
| Bulb and stem nematode, beet eelworm | *Ditylenchus dipsaci* |

TABLE 4-continued

Parasitic nematodes

| Damage | Pathogenic nematode |
| --- | --- |
| ("Bulb and stem"; Europe) | |
| Burrowing | *Radopholus similis* |
| Cereal cyst nematode ("Cyst") | *Heterodera avenae, H. zeae, Punctodera chalcoensis* |
| Dagger | *Xiphinema* spp., *X. americanum, X. mediterraneum* |
| False root-knot | *Nacobbus dorsalis* |
| Lance, Columbia | *Hoplolaimus columbus* |
| Lance | *Hoplolaimus* spp., *H. galeatus* |
| Lesion | *Pratylenchus* spp., *P. brachyurus, P. crenatus, P. hexincisus, P. neglectus, P. penetrans, P. scribneri, P. thornei, P. zeae* |
| Needle | *Longidorus* spp., *L. breviannulatus* |
| Ring | *Criconemella* spp., *C. ornata* |
| Root-knot nematode | *Meloidogyne* spp., *M. chitwoodi, M. incognita, M. javanica* |
| Spiral | *Helicotylenchus* spp. |
| Sting | *Belonolaimus* spp., *B. longicaudatus* |
| Stubby-root | *Paratrichodorus* spp., *P. christiei, P. minor, Quinisulcius acutus, Trichodorus* spp. |
| Stunt | *Tylenchorhynchus dubius* |

Particularly preferably, the transgenic plants produced according to the present invention are resistant to *Globodera rostochiensis* and *G. pallida* (cyst nematodes of potato, tomato, and other *solanaceae*), *Heterodera schachtii* (beet cyst nematodes of sugar and fodder beets, rape, cabbage, etc.), *Heterodera avenae* (cereal cyst nematode of oat and other types of cereal), *Ditylenchus dipsaci* (bulb and stem nematode, beet eelworm of rye, oat, maize, clover, tobacco, beet), *Anguina tritici* (wheat seed gall nematode), seed galls of wheat (spelt, rye), *Meloidogyne hapla* (root-knot nematode of carrot, cucumber, lettuce, tomato, potato, sugar beet, lucerne).

In individual sorts of particular agricultural importance, the plants according to the present invention are preferably resistant to the following pathogens:

In barley, the plants are resistant to the fungal, bacterial, and viral pathogens *Puccinia graminis* f. sp. *hordei* (barley stem rust), *Blumeria* (Erysiphe) *graminis* f. sp. *hordei* (barley powdery mildew), barley yellow dwarf virus (BYDV), and the pathogenic insects/nematodes *Ostrinia nubilalis* (European corn borer); *Agrotis ipsilon* (black cutworm); *Schizaphis graminum* (greenbug); *Blissus leucopterus leucopterus* (chinch bug); *Acrosternum hilare* (green stink bug); *Euschistus servus* (brown stink bug); *Deliaplatura* (seedcorn maggot); *Mayetiola destructor* (Hessian fly); *Petrobia latens* (brown wheat mite).

In soy bean, the plants are resistant to the fungal, bacterial, or viral pathogens *Phytophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotrichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffussa*, *Fusarium semitectum*, *Phialophora gregata*, soy bean mosaic virus, *Glomerella* glycines, tobacco ring spot virus, tobacco streak virus, *Phakopsorapachyrhizi*, *Pythium aphamidermatum*, *Pythium ultimum*, *Pythium debaryanum*, tomato spotted wilt virus, *Heterodera glycines*, *Fusarium solani* and the pathogenic insects/nematodes *Pseudoplusia includens* (soybean looper); *Anticarsia gemmatalis* (velvetbean caterpillar); *Plathypena scabra* (green cloverworm); *Ostrinia nubilalis* (European corn borer); *Agrotis ipsilon* (black cutworm); *Spodoptera exigua* (beet armyworm); *Heliothis virescens* (cotton budworm); *Helicoverpa zea* (cotton bollworm); *Epilachna varivestis* (Mexican bean beetle); *Myzus persicae* (green peach aphid); *Empoasca fabae* (potato leaf hopper); *Acrosternum hilare* (green stink bug); *Melanoplus femurrubrum* (redlegged grasshopper); *Melanoplus differentialis* (differential grasshopper); *Hylemya platura* (seedcorn maggot); *Sericothrips variabilis* (soybean thrips); *Thrips tabaci* (onion thrips); *Tetranychus turkestani* (strawberry spider mite); *Tetranychus urticae* (twospotted spider mite).

In canola, the plants are resistant to the fungal, bacterial, or viral pathogens *Albugo candida*, *Alternaria brassicae*, *Leptosphaeria maculans*, *Rhizoctonia solani*, *Sclerotinia sclerotiorum*, *Mycosphaerella brassiccola*, *Pythium ultimum*, *Peronospora parasitica*, *Fusarium roseum*, *Alternaria alternata*.

In alfalfa, the plants are resistant to the fungal, bacterial, or viral pathogens *Clavibater michiganese* subsp. *insidiosum*, *Pythium ultimum*, *Pythium irregulare*, *Pythium splendens*, *Pythium debaryanum*, *Pythium aphamidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium*, *Xanthomonas campestris* p.v. *alfalfae*, *Aphanomyces euteiches*, *Stemphylium herbarum*, *Stemphylium alfalfae*.

In wheat, the plants are resistant to the fungal, bacterial, or viral pathogens *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f. sp. *tritici*, *Puccinia graminis* f. sp. *tritici*, *Puccinia recondita* f. sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphamidermatum*, *Pythium arrhenomanes*, *Pythium ultimum*, *Bipolaris sorokiniana*, *Barley Yellow Dwarf Virus*, *Brome Mosaic Virus*, *Soil Borne Wheat Mosaic Virus*, *Wheat Streak Mosaic Virus*, *Wheat Spindle Streak Virus*, *American Wheat Striate Virus*, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphamidermatum*, High Plains Virus, European wheat striate virus, *Puccinia graminis* f. sp. *tritici* (Wheat stem rust), *Blumeria* (Erysiphe) *graminis* f. sp. *tritici* (Wheat Powdery Mildew) and to the pathogenic insects/nematodes *Pseudaletia unipunctata* (army worm); *Spodoptera frugiperda* (fall armyworm); *Elasmopalpus lignosellus* (lesser cornstalk borer); *Agrotis orthogonia* (western cutworm); *Elasmopalpus Zignosellus* (lesser cornstalk borer); *Oulema melanopus* (cereal leaf beetle); *Hypera punctata* (clover leaf weevil); *Diabrotica undecimpunctata howardi* (southern corn rootworm); Russian wheat aphid; *Schizaphis graminum* (greenbug); *Macrosiphum avenae* (English grain aphid); *Melanoplus femurrubrum* (redlegged grasshopper); *Melanoplus differentialis* (differential grasshopper); *Melanoplus sanguinipes* (migratory grasshopper); *Mayetiola destructor* (Hessian fly); *Sitodiplosis mosellana* (wheat midge); *Meromyza americana* (wheat stem maggot); *Hylemya coarctata* (wheat bulb fly); *Frankliniella fusca* (tobacco thrips); *Cephus cinctus* (wheat stem sawfly); *Aceria tulipae* (wheat curl mite).

In sun flower, the plants are resistant to the fungal, bacterial, or viral pathogens Plasmophora halstedii, Sclerotinia sclerotiorum, Aster Yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* p.v. *Carotovora*, *Cephalosporium acremonium*, *Phytophthora cryptogea*, *Albugo tragopogonis* and to the pathogenic insects/nematodes *Suleima helianthana* (sunflower bud moth); *Homoeosoma electellum* (sunflower moth); *Zygogramma exclamationis* (sunflower beetle); *Bothyrus gibbosus* (carrot beetle); *Neolasioptera murtfeldtiana* (sunflower seed midge).

In maize, the plants are resistant to the fungal, bacterial, or viral pathogens *Fusarium moniliforme* var. *subglutinans*, *Erwinia stewartii*, *Fusarium moniliforme*, *Gibberella zeae* (*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphamidermatum*, *Aspergillus flavus*, *Bipolaris maydis* 0, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella maydis*, *Cercospora sorghi*, *Ustilago* maydis, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganese* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Erwinia chrysanthemi* p.v. *Zea*, *Erwinia corotovora*, Cornstunt spiroplasma, *Diplodia macrospora*, *Sclerophthora macrospora*, *Peronosclerospora sorghi*, *Peronosclerospora philippinesis*, *Peronosclerospora maydis*, *Peronosclerospora sacchari*, *Spacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maize Streak Virus (MSV, Maisstrichel-Virus), Maize Stripe Virus, Maize Rough Dwarf Virus, and the pathogenic insects/nematodes *Ostrinia nubilalis* (European corn borer); *Agrotis ipsi-*

*lon* (black cutworm); *Helicoverpa zea* (corn earworm); *Spodoptera frugiperda*. (fall armyworm); *Diatraea grandiosella* (southwestern corn borer); *Elasmopalpus lignosellus* (lesser cornstalk borer); *Diatraea saccharalis* (sugarcane borer); *Diabrotica virgifera* (western corn rootworm); *Diabrotica longicornis barberi* (northern corn rootworm); *Diabrotica undecimpunctata howardi* (southern corn rootworm); *Melanotus* spp. (wireworms); *Cyclocephala borealis* (northern masked chafer; white grub); *Cyclocephala immaculata* (southern masked chafer; white grub); *Popillia japonica* (Japanese beetle); *Chaetocnema pulicaria* (corn flea beetle); *Sphenophorus maidis* (maize billbug); *Rhopalosiphum maidis* (corn leaf aphid); *Anuraphis maidiradicis* (corn root aphid); *Blissus leucopterus leucopterus* (chinch bug); *Melanoplus femurrubrum* (redlegged grasshopper); *Melanoplus sanguinipes* (migratory grasshopper); *Hylemva platura* (seedcorn maggot); *Agromyza parvicornis* (corn blot leafminer); *Anaphothrips obscurus* (grass thrips); *Solenopsis milesta* (thief ant); *Tetranychus urticae* (twospotted spider mite).

In sorghum, the plants are resistant to the fungal, bacterial, or viral pathogens *Exserohilum turcicum, Colletotrichum graminicola* (Glomerella graminicola), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola* and to the pathogenic insects/nematodes *Chilo partellus* (sorghum borer); *Spodoptera frugiperda* (fall armyworm); *Helicoverpa zea* (corn earworm); *Elasmopalpus lignosellus* (lesser cornstalk borer); *Feltia subterranea* (granulate cutworm); *Phyllophaga crinita* (white grub); *Eleodes, Conoderus* und *Aeolus* spp. (wireworm); *Oulema melanopus* (cereal leaf beetle); *Chaetocnema pulicaria* (corn flea beetle); *Sphenophorus maidis* (maize billbug); *Rhopalosiphum maidis* (corn leaf aphid); *Siphaflava* (yellow sugarcane aphid); *Blissus leucopterus leucopterus* (chinch bug); *Contarinia sorghicola* (sorghum midge); *Tetranychus cinnabarinus* (carmine spider mite); *Tetranychus urticae* (two-spotted spider mite).

In cotton, the plants are resistant to the pathogenic insects/nematodes: *Heliothis virescens* (cotton budworm); *Helicoverpa zea* (cotton bollworm); *Spodoptera exigua* (beet armyworm); *Pectinophora gossypiella* (pink bollworm); *Anthonomus grandis grandis* (boll weevil); *Aphis gossypii* (cotton aphid); *Pseudatomoscelis seriatus* (cotton fleahopper); *Trialeurodes abutilonea* (bandedwinged whitefly); *Lygus lineolaris* (tarnished plant bug); *Melanoplus femurrubrum* (redlegged grasshopper); *Melanoplus differentialis* (differential grasshopper); *Thrips tabaci* (onion thrips); *Franklinkiella fusca* (tobacco thrips); *Tetranychus cinnabarinus* (carmine spider mite); *Tetranychus urticae* (two-spotted spider mite);

In rice, the plants are resistant to the pathogenic insects/nematodes *Diatraea saccharalis* (sugarcane borer); *Spodoptera frugiperda* (fall armyworm); *Helicoverpa zea* (corn earworm); *Colaspis brunnea* (grape *colaspis*); *Lissorhoptrus oryzophilus* (rice water weevil); *Sitophilus oryzae* (rice weevil); *Nephotettix nigropictus* (rice leafhopper); *Blissus leucopterus* leucopterus (chinch bug); *Acrosternum hilare* (green stink bug);

In rape, the plants are resistant to the pathogenic insects/nematodes *Brevicoryne brassicae* (cabbage aphid); *Phyilotreta cruciferae* (Flea beetle); *Mamestra configurata* (Bertha armyworm); *Plutella xylostella* (Diamond-back moth); *Delia* ssp. (Root maggots).

In particular preferably, the term "plant pathogen" comprises pathogens from the group *Blumeria graminis* f. sp. *hordei, tritici, avenae, secalis, lycopersici, vitis, cucumis, cucurbitae, pisi, pruni, solani, rosae, fragariae, rhododendri, mali*, and *nicotianae*.

According to the present invention, the term "actin-depolymerizing factor 3 (ADF3) from barley" is understood to denote a protein having SEQ ID No. 1.

According to the present invention, the term "actin-depolymerizing factors (ADFs)" is understood to denote such proteins, whose sequence has a significant homology to the ADF3 from barley mentioned in the above.

If ADF3 is mentioned in the following, this denotes the ADF3 from barley having the SEQ ID No. 1, whereas the use of the term "ADFs" denotes the ADF3 from barley and/or such proteins having a significant or essential homology to the ADF3 from barley.

According to the present invention, the "content" of ADF3 from barley or of ADFs in general is understood to denote the amount of ADF3 or of a particular ADF, which can be determined for the wild-type of a plant or plant cell.

The "activity" of ADF3 or of ADFs in general is understood to denote their capability of interacting with globular actin (G-actin) or filamentous actin (F-actin) or with other physiological binding partners.

Thus, according to the present invention, an "altered content" of ADFs "as compared to the wild-type" is understood to denote an increased or reduced amount of ADFs as compared to the wild-type. Herein, the increase of the content of ADFs can be achieved by increasing the amount of endogenous ADFs or by delivering an additional amount of exogenous ADFs. In general, the reduction of the amount of ADFs in the transgenic plants or plant cells according to the present invention is achieved by reducing the content of endogenous ADFs.

According to the present invention, a "wild-type" is understood to denote the corresponding original organism, which has not been genetically modified.

An increase of the activity of ADFs can be achieved by increasing the activity of the endogenous ADFs and/or by delivering an additional amount of functional ADFs. Reducing the activity of ADFs can be achieved by reducing the activity of endogenous ADFs. Likewise, according to the present invention, a reduction of the activity of ADFs is understood to denote that the activity of endogenous ADF3 or endogenous ADFs remains unmodified while, however, the interaction of the ADFs with their physiological binding partners, for example by expressing non-functional forms of ADFs or antibodies, is significantly inhibited.

Preferably, the increase in content and/or activity of ADFs in a transgenic plant or plant cell, which is effected by a method according to the present invention, amounts to at least 5%, preferably to at least 20%, also preferably to at least 50%, especially preferably to at least 100%, also especially preferably to at least the factor 5, in particular preferably to at least the factor 10, also in particular preferably to at least the factor 50, more preferably to at least the factor 100, and most preferably to at least the factor 1000. The transgenic plants according to the present invention exhibit comparable increases in the content and/or activity of ADFs in a transgenic plant or plant cell.

Preferably, the reduction of content and/or activity of ADFs in a transgenic plant cell or plant, which is effected by a method according to the present invention, amounts to at least 5%, preferably to at least 10%, especially preferably to at least 20%, also especially preferably to at least 40%, additionally especially preferably to at least 60%, in particular preferably to at least 80%, also in particular preferably to at least 90%, and most preferably to at least 98%.

As has already been mentioned in the above, an object of the present invention relates to an isolated nucleic acid molecule coding for the ADF3 from barley identified in SEQ ID No. 1. A further object of the present invention relates to nucleic acid molecules coding for functionally equivalent parts of the ADF3 from barley identified in SEQ ID No. 1.

If, within the scope of the present invention, "functionally equivalent parts of ADF3" are mentioned, this is understood to denote fragments of the nucleic acid sequences as coding for the ADF3 having the SEQ ID No. 1, whose expression still yields proteins having the binding properties and structural properties of the ADF3. The term "functionally equivalent parts" is to be understood in the same way, if it relates to protein fragments in general. Particularly preferably, these are nucleic acid sequences leading to ADF3 fragments having deletions of several amino acids at the N- and/or C-terminus without exhibiting an alteration of the structural properties or the binding quality of the ADF3. In particular, "binding properties of ADF3" is understood to denote the binding behaviour of the ADF3 to G-actin and/or F-actin.

A further object of the present invention are nucleic acid molecules coding for mutants of the ADF3. "Mutants of ADF3" are understood to denote both functional and non-functional mutants of ADF3. Functional mutants are forms of the ADF3 having point mutation/s, insertion/s, and/or deletion/s, without suffering an essential loss of the structural or binding properties of the ADF3.

The binding properties of ADF3 from *Zea mays*, as well as their structural properties, have been described (Jiang et al. (1997), Proc. Natl. Acad. Sci. USA, 94, 9973-9978). As the ADF3 from maize is an ADF being essentially homologous to the ADF3 from barley in the sense of the present invention, the teachings concerning the binding behavior of ADFs to G-actin and F-actin, which have been described in the previously mentioned publication, may also be used in the production of functional and non-functional mutants of the ADF3 from barley according to the present invention (see below).

In general, functional point mutants are obtained by performing a so-called conservative amino acid substitution, i.e. amino acids having comparable physico-chemical properties are substituted for one another. Herein, hydrophobic amino acids are substituted for hydrophobic amino acids, hydrophilic amino acids for hydrophilic amino acids, positively charged amino acids for positively charged amino acids, etc. A substitution of a valine for an alanine is an example for a conservative amino acid substitution. Here, the person skilled in the art will pay attention as to whether the conservative amino acid substitution is located in a region of ADF3 which is essential for its binding behavior to F-actin or G-actin. Clues as to whether a particular region is essential for the binding behavior of ADF3 may result from a so-called sequence alignment with already known ADFs, for which the binding properties and structural properties have already been determined (see Jiang et al., vide supra). In contrast to a conservative mutation, the person skilled in the art will rather not assume that a substitution of, for example, a lysine for a glutamate, i.e. a positively charged moiety for a negatively charged moiety, will not lead to a functional or structural alteration of the ADF. The same considerations made in producing functional point mutants of ADF3 also apply for producing functional insertion and/or deletion mutants of ADF3 on the condition that the person skilled in the art will, in this case, pay particular attention as to whether the added or deleted amino acid sequence regions are located within a region that is essential for binding to actin or not.

An $S^6A$ amino acid substitution avoiding that the protein at the N-terminus is phosphorylated is an example for a functional mutant. Due to the substitution of serine by alanine in amino acid position 6, such a mutant of ADF3 (SEQ ID No. 2) is permanently active and cannot be regulated post-translationally anymore.

The mutated amino acid is located at position 6 of the amino acid sequence, wherein the wild-type serine (S) was substituted by an alanine (A) (Smertenko, A. P. et al. (1998) Plant J 14, 187-193).

As already mentioned in the above, nucleic acid molecules coding for non-functional mutants of the ADF3 from barley are also an object of the present invention. Such non-functional mutants of the ADF3 are forms of ADF3, which are no longer, or at least only in a very limited manner, capable of interacting with G-actin and/or F-actin or other physiological binding partners of ADF3. Such non-functional mutants of ADF3 can in turn comprise point mutation/s, insertion/s and/or deletion/s. Such non-functional mutants of ADF3 are useful, for example, in producing transgenic plants or plant cells, in which the content of endogenous ADF3 is not altered in barley, while the activity of endogenous ADF3 is blocked, however, by overexpressing the mentioned non-functional mutants.

According to the present invention, non-functional mutants of ADF3 have substantially the same nucleic acid or amino acid sequences like functional mutants of ADF3. They have, however, in some positions point mutation/s, insertion/s, or deletion/s of nucleotides or amino acids, which, in contrast to functional mutants of ADF3, have the effect that the non-functional mutants of ADF3 are not, or only in a very limited manner, capable of interacting with F-actin, G-actin, and/or other physiological binding partners. Such functional or non-functional mutants of ADF3 according to the present invention can easily be identified by the person skilled in the art. The person skilled in the art has at his disposal a variety of techniques allowing the insertion of point mutation/s, insertion/s or deletion/s into the nucleic acid sequences coding for functional or non-functional mutants of ADF3 (Sambrook (2001), Molecular Cloning: A Laboratory Manual, 3rd edition, Coldspring Harbour Laboratory Press). Subsequently to introducing the point mutation/insertion and/or deletion, which may also generally be referred to as mutation, the person skilled in the art is, by means of corresponding binding tests as illustrated in the Examples or known from the prior art, capable of determining whether the mutagenized ADF3 still possess their normal binding properties with respect to G-actin, F-actin, and/or other physiological binding partners.

As compared to the non-mutagenized ADF3 or to the functional mutant of ADF3, non-functional mutants of ADF3 have a reduced binding specifity, preferably for G-actin and/or F-actin. According to the present invention, a non-functional mutant of ADF3 has 1 to 90%, preferably 1 to 70%, especially preferably 1 to 50%, also especially preferably 1 to 30%, in particular preferably 1 to 15%, and most preferably 1 to 10% of the binding efficiency of ADF3 or of the respective functional mutants of ADF3, as compared to the respective pathogenic and/or physiological binding partner, herein preferably as compared to G-actin and/or F-actin.

Examples for amino acid positions, which are essential for interaction with G-actin and/or F-actin, are amino acid positions in ADF3 from barley corresponding to the positions tyrosine-67 and tyrosine-70 in the ADF3 from maize. These are the positions phenylalanine-66 and phenylalanine-69 in HvADF3.

According to the present invention, the term "non-functional ADF3" does not comprise such proteins having no substantial sequence homology to functional ADF3 on the amino acid or nucleic acid level. According to the present invention, proteins that are not capable of binding to G-actin and/or F-actin and have no substantial sequence homology to ADF3 are thus, per definition, not denoted by the inventive term "non-functional mutant of ADF3". Within the scope of the present invention, non-functional mutants of ADF3 are also referred to as inactivated or inactive ADF3.

Thus, the functional and/or non-functional mutants of ADF3 of the present invention containing the previously mentioned point mutation/s, insertion/s, and/or deletion/s or the functionally equivalent parts are characterized by a substantial sequence homology to ADF3.

According to the present invention, the term "substantial sequence homology" is generally understood to denote that the nucleic acid or amino acid sequence of a DNA molecule or of a protein is identical to the nucleic acid or amino acid sequences of ADF3 or functionally equivalent parts thereof by at least 40%, preferably by at least 50%, further preferably by at least 60%, also preferably by at least 70%, 80% or 85%, especially preferably by at least 90%, particularly preferably by at least 95%, and most preferably by at least 98%. Preferably, homology is determined over the entire sequence length of ADF3.

"Identity of two proteins" is understood to denote the identity of the amino acids over a particular protein region, preferably over the entire protein length, in particular the identity calculated by comparison with the aid of the Lasergene software by DNA Star Inc., Madison, Wis. (USA) using the CLUSTAL method (Higgins et al., 1989, Comput. Appl. Biosci., (2), 151).

Thus, homology is preferably calculated over the entire amino acid or nucleic acid sequence region. Beside the programs mentioned in the above, the person skilled in the art has at his disposal further programs based on different algorithms for comparing different sequences. Herein, the algorithms by Needleman and Wunsch, or Smith and Waterman yield particularly reliable results. For said sequence comparisons, for example, the program Pile Aupa (J. Mol. Evolution. (1987), 25, 351-360; Higgins et al., (1989), Cabgos, 5, 151-153) or the programs Gap and Best Fit (Needleman and Wunsch, (1970), J. Mol. Biol., 48, 443-453 and Smith and Waterman (1981), Adv., Appl. Math., 2, 482-489), which are contained in the GCG Software Package by the Genetics Computer Group (575 Science Drive, Madison, Wis., USA 53711), can also be used.

The Clustal W program, as can be called up at the European Bioinformatics Institute (EBI) web site, was used for the sequence alignments conducted within the scope of the present invention. The parameters of said default homepage remained unaltered for the alignments.

A further object of the present invention are nucleic acid molecules, which hybridize under stringent conditions with, or are substantially complementary to, those nucleic acid molecules coding for ADF3, functionally equivalent parts thereof, or for functional or non-functional mutants of ADF3. The term "complementarity" describes the capability of a nucleic acid molecule of hybridizing with another nucleic acid molecule due to hydrogen bonds formed between complementary bases. The person skilled in the art is aware of the fact that two nucleic acid molecules do not have to have a 100% complementarity in order to be able to hybridize with each other. Preferably, a nucleic acid sequence, which is supposed to hybridize with another nucleic acid sequence, is complementary to the latter by at least 40%, by at least 50%, by at least 60%, preferably by at least 70%, especially preferably by at least 80%, also especially preferably by at least 90%, particularly preferably by at least 95%, and most preferably by at least 98% or 100%.

Preferably, the degrees of homology, complementarity and identity are to be determined over the entire length of the protein or nucleic acid.

Nucleic acid molecules are identical if they have identical nucleotides in the same 5' to 3' order.

Stringent in vitro hybridization conditions are known to the person skilled in the art and can be taken from the literature (see, for example, Sambrook et al., vide supra). The term "specific hybridization" relates to the fact that a molecule preferably binds to a specific nucleic acid sequence under stringent conditions, provided that said nucleic acid sequence is part of a complex mixture of, for example, DNA or RNA molecules.

Thus, the term "stringent conditions" relates to conditions, under which a nucleic acid sequence preferably binds to a target sequence, but not, or at least in a significantly reduced manner, to other sequences.

Stringent conditions are dependent on the circumstances. Longer sequences hybridize specifically at higher temperatures. In general, stringent conditions are selected in such a way that the hybridization temperature is about 5° C. below the melting point ($T_m$) for the specific sequence at a defined ionic strength and a defined pH value. $T_m$ is the temperature (at a defined pH value, a defined ionic strength, and a defined nucleic acid concentration), at which 50% of the molecules, which are complementary to a target sequence, hybridize with said target sequence. Typically, stringent conditions comprise salt concentrations between 0.01 and 1.0 M sodium ions (or ions of another salt) and a pH value between 7.0 and 8.3. The temperature is at least 30° C. for short molecules (for example, for those comprising between 10 and 50 nucleotides). In addition, stringent conditions may comprise the addition of destabilizing agents, like for example formamide. Typical hybridization and washing buffers are of the following composition.

| | |
|---|---|
| Pre-hybridization solution: | 0.5% SDS |
| | 5 x SSC |
| | 50 mM NaPO$_4$, pH 6.8 |
| | 0.1% Na pyrophosphate |
| | 5 x Denhardt's Reagent |
| | 100 µg/ml salmon sperm |
| Hybridization solution: | Pre-hybridization solution |
| | 1 x 10$^6$ cpm/ml probe (5-10 min, 95° C.) |
| 20 x SSC: | 3 M NaCl |
| | 0.3 M sodium citrate |
| | ad pH 7 with HCl |
| 50 x Denhardt's Reagent: | 5 g Ficoll |
| | 5 g polyvinyl pyrrolidone |
| | 5 g Bovine Serum Albumin |
| | ad 500 ml A. dest. |

A typical hybridization procedure is conducted as follows:

| | |
|---|---|
| Optional: | washing the blot 30 min in 1 x SSC/0.1% SDS at 65° C. |
| Pre-hybridization: | at least 2 h at 50-55° C. |

-continued

| Hybridization: | overnight at 55-60° C. | | |
|---|---|---|---|
| Washing: | 5 min | 2 x SSC/0.1% SDS | Hybridization temp. |
| | 30 min | 2 x SSC/0.1% SDS | Hybridization temp. |
| | 30 min | 1 x SSC/0.1% SDS | Hybridization temp. |
| | 45 min | 0.2 x SSC/0.1% SDS | 65° C. |
| | 5 min | 0.1 x SSC | Room temp. |

As has already been mentioned in the above, the previously mentioned nucleic acid sequences coding for ADF3 from barley, for functionally equivalent parts thereof, or for functional or non-functional mutants thereof can be used for producing transgenic plants having an altered content and/or an altered activity of ADF3, which leads to the result that the plants have an increased pathogen resistance against the mildew pathogen *Blumeria graminis* f. sp. *hordei*.

However, the present invention is not limited to methods for producing transgenic barley plants or barley plant cells, which exhibit an increased resistance against *Blumeria graminis* f. sp. *hordei* due to an altered content and/or an altered activity of ADF3 from barley.

It is assumed that (i) transgenic plants or plant cells having an increased pathogen resistance in the sense of the present invention can also be produced by altering the content and/or the activity of homologs of ADF3 in other plants and (ii) that homologs of ADF3 from barley can also be used for producing transgenic plants or plant cells having an increased pathogen resistance.

Thus, the present invention in general relates to methods for producing transgenic plants or plant cells with an increased pathogen resistance, wherein the content and/or activity of at least one ADF is altered as compared to the wild-type. In the methods described in the following for producing transgenic plants with increased pathogen resistance and for altering the content and/or activity of at least one ADF, such nucleic acid sequences coding for ADFs that are substantially homologous to the ADF3 having the SEQ ID No. 1 from barley can thus also be used beside the nucleic acid sequences mentioned in the above.

According to the present invention, a substantial sequence homology of ADFs to the ADF3 having the SEQ ID No. 1 from barley is herein understood to denote that the nucleic acid or amino acid sequences of such an ADF are identical to the nucleic acid or amino acid sequences of the ADF3 from barley by at least 40%, preferably by at least 50%, further preferably by at least 60%, also preferably by at least 70%, 80% or 85%, particularly preferably by at least 90%, in particular preferably by at least 95%, and most preferably by at least 98%. Herein, sequence homology can be determined according to the methods mentioned in the above.

Beside the previously mentioned nucleic acid sequences coding for ADFs being substantially homologous to ADF3 from barley, it is also possible in the methods according to the present invention to use such nucleic acids coding for functionally equivalent parts of the ADFs or for functional or non-functional mutants of the ADFs, on the condition that the latter be ADFs that are substantially homologous to the ADF3 from barley. Herein, the previously described definitions for functionally equivalent parts or functional or non-functional mutants also apply to the ADFs in general.

Examples for such ADFs, which can be used for the methods according to the present invention, are the ADFs from *Arabidopsis thaliana*, *Zea mays*, *Hordeum vulgare*, *Oryza sativa*, and *Triticum aestivum*, which are given in Table 5. The person skilled in the art can take nucleotide and amino acid sequences suitable for the ADFs both from the database entries given in the Table and from the sequence listing.

TABLE 5

| Organism | ADF | Database/Accession Code | Amino acid sequence SEQ ID NO. | DNA Sequence SEQ ID NO. |
|---|---|---|---|---|
| *Hordeum vulgare* | HvADF3 | Tigr/45377 | 1 | 45 |
| | HvADF3-S6A | — | 2 | 46 |
| | HvADF1 | Tigr/46250 | 3 | 47 |
| | HvADF2 | Tigr/60360 | 4 | 48 |
| | HvADF5 | Tigr/TC46717 | 5 | 49 |
| | HvADF6 | GenBank/CD056371 | 6 | 50 |
| | HvADF8 | Tigr/TC49352 | 7 | 51 |
| | HvADF10 | Tigr/TC62764 | 8 | 52 |
| *Arabidopsis thaliana* | AtADF1 | GenBank/At3g46010 | 9 | 53 |
| | AtADF2 | GenBank/At3g46000 | 10 | 54 |
| | AtADF3 | GenBank/At5g59880 | 11 | 55 |
| | AtADF4 | GenBank/At5g59890 | 12 | 56 |
| | AtADF5 | GenBank/At2g16700 | 13 | 57 |
| | AtADF6 | GenBank/At2g31200 | 14 | 58 |
| | AtADF7 | GenBank/At5g52360 | 15 | 59 |
| | AtADF8 | GenBank/At4g00680 | 16 | 60 |
| | AtADF9 | GenBank/At4g34970 | 17 | 61 |
| | AtADF10 | GenBank/At1g01750 | 18 | 62 |
| | AtADF11 | GenBank/At4g25590 | 19 | 63 |
| | AtADF12 | GenBank/At3g45990 | 20 | 64 |
| *Oryza sativa* | OsADF1 | Tigr/TC201477 | 21 | 65 |
| | OsADF2 | Tigr/TC208620 | 22 | 66 |
| | OsADF3 | GenBank/AC104433 | 23 | 67 |
| | OsADF4 | Tigr/TC192283 | 24 | 68 |
| | OsADF5 | Tigr/TC202703 | 25 | 69 |
| | OsADF6 | Tigr/TC185994 | 26 | 70 |
| | OsADF7 | GenBank/AL606647 | 27 | 71 |
| | OsADF8 | GenBank/AK072662 | 28 | 72 |
| | OsADF9 | Tigr/TC106152 | 29 | 73 |
| | OsADF10 | GenBank/AK069605.1 | 30 | 74 |
| | OsADF11 | GenBank/AC104433 | 31 | 75 |

TABLE 5-continued

| Organism | ADF | Database/Accession Code | Amino acid sequence SEQ ID NO. | DNA Sequence SEQ ID NO. |
|---|---|---|---|---|
| Triticum aestivum | TaADF1 | Tigr/88586 | 32 | 76 |
| | TaADF2 | Tigr/70034 | 33 | 77 |
| | TaADF3a | GenBank/BJ284976 | 34 | 78 |
| | TaADF3b | GenBank/CA486380 | 35 | 79 |
| | TaADF4 | Tigr/70035 | 36 | 80 |
| | TaADF5 | Tigr/66848 | 37 | 81 |
| | TaADF6 | Tigr/86040 | 38 | 82 |
| Zea mays | ZmADF1 | Tigr/TC150616 | 39 | 83 |
| | ZmADF2 | Tigr/TC150192 | 40 | 84 |
| | ZmADF3 | Tigr/TC148556 | 41 | 85 |
| | ZmADF5 | Tigr/TC150207 | 42 | 86 |
| | ZmADF6 | Tigr/TC159321 | 43 | 87 |
| | ZmADF7 | Tigr/TC150192 | 44 | 88 |

The GenBank database is accessible via the National Center for Biotechnology Information (NCBI) web site. The TIGR database is accessible via the Institute for Genomic Research (TIGR) web site.

Thus, a multiplicity of DNA sequences coding for substantial homologs of ADF3 from barley are already known. Moreover, those sequences of ADFs that are not yet available in the public databases can also be used within the scope of the present invention.

The person skilled in the art knows how to isolate the respective corresponding DNA sequences from other organisms. Typically, the person skilled in the art will first try to identify corresponding homologous sequences by comparing homologies in the established databases, like for example the GenBank database of the NCBI. Such databases can be found on the NCBI homepage at the NIH under.

DNA sequences having a high homology, i.e. a high similarity or identity, are bona fide candidates for DNA sequences corresponding to the DNA sequences according to the present invention, i.e. ADF3. Said gene sequences can be isolated by means of standard methods, like for example PCR and hybridization, and their function can be determined by the person skilled in the art by means of corresponding enzyme activity tests and other experiments. According to the present invention, homology comparisons with DNA sequences can also be used in order to design PCR primers by identifying at first the regions that are most conserved between the DNA sequences of different organisms. Such PCR primers can then be used to isolate, in a first step, DNA fragments that are parts of DNA sequences homologous to the DNA sequences of the present invention.

There are a variety of search engines, which can be used for such homology comparisons or searches. Said search engines comprise, for example, the CLUSTAL program group of the BLAST program, which is provided by the NCBI.

Furthermore, a variety of experimental methods, by which DNA sequences can be isolated from most diverse organisms that are homologous to the ADFs according to the present invention, are known to the person skilled in the art. Among said methods are, for example, the preparation and screening of cDNA libraries with correspondingly degenerated probes (see also Sambrook et al., vide supra).

According to the present invention, the ADF3 from barley and the ADFs in general have a so-called consensus region. A so-called sequence alignment of different ADF sequences from *A. thaliana* with ADF3 from barley can be seen in FIG. 1.

From said sequence alignment, different consensus sequences can be derived, which are characteristic for the ADFs according to the present invention. The consensus sequence I comprises the following sequence:

$X_1PX_2X_3X_4CRX_5X_6X_7X_8DX_9X_{10}X_{11}$   (SEQ ID No. 89)

Herein, $X_1$ can comprise any optional amino acid, preferably L or I. $X_2$ can comprise any amino acid. $X_3$ can comprise any amino acid, preferably N or D. $X_4$ can comprise any amino acid, preferably D or E. $X_5$ can comprise any amino acid, preferably Y or F, $X_6$ can comprise any amino acid, preferably A or C. $X_7$ can comprise any amino acid, preferably V or I. $X_8$ can comprise any amino acid. $X_9$ can comprise any amino acid. $X_{10}$ can comprise any amino acid, preferably D or E. $X_{11}$ can comprise any amino acid, preferably F or Y. Herein, the amino acids are given according to the conventional one letter code.

In addition, the ADFs, which can be used for use in the methods according to the present invention, are characterized by the presence of a second consensus sequence.

Said consensus sequence II comprises the following sequence:

(SEQ ID No. 90)
$Y_1IY_2Y_3Y_4Y_5WY_6PY_7Y_8Y_9Y_{10}Y_{11}RY_{12}Y_{13}Y_{14}Y_{15}$

Herein, $Y_1$ can be any amino acid, preferably K or R. $Y_2$ can be any amino acid. $Y_3$ can be any amino acid, preferably F or Y. $Y_4$ can be any amino acid, preferably F, I, or V. $Y_5$ can be any amino acid. $Y_6$ can be any amino acid, preferably S or C. $Y_7$ can be any amino acid, preferably S, E, or D. $Y_8$ can be any amino acid. $Y_9$ can be any amino acid, preferably S or A. $Y_{10}$ can be any amino acid. $Y_{11}$ can be any amino acid, preferably I, V, or M. $Y_{12}$ can be any amino acid. $Y_{13}$ can be any amino acid, preferably I, V, or M. $Y_{14}$ can be any amino acid. $Y_{15}$ can be any amino acid, preferably S or A. Herein, the amino acids are also given in form of their one letter code.

Furthermore, the ADFs suitable for use in one of the methods of the present invention are characterized by the following consensus sequence.

The consensus sequence III comprises the following sequence:

$RZ_1Z_2Z_3GZ_4Z_5Z_6EZ_7Z_8ATDZ_9Z_{10}Z_{11}Z_{12}$   (SEQ ID No. 91)

$Z_1$ can be any amino acid, preferably E, V, or T. $Z_2$ can be any amino acid, preferably L or M. $Z_3$ can be any amino acid, preferably Q, E, or D. $Z_4$ can be any amino acid, preferably I or V. $Z_5$ can be any amino acid, preferably H or Q. $Z_6$ can be any amino acid. $Z_7$ can be any amino acid, preferably I, L, M, or F. $Z_8$ can be any amino acid, preferably Q or H. $Z_9$ can be any amino acid. $Z_{10}$ can be any amino acid, preferably T or S. $Z_{11}$ can be any amino acid, preferably E or D. $Z_{12}$ can be any amino acid, preferably V, M, or I. Again, the amino acids are given in the one letter code.

The ADF sequences according to the present invention or the ADFs, which can be used for the methods according to the present invention, can also contain the three previously mentioned consensus sequences I, II, and III in combination.

Thus, the present invention also relates to nucleic acid sequences coding for, inter alia, the consensus sequence illustrated in the above having the SEQ ID No. 89, 90, and/or 91, as well as to its use in the methods according to the present invention for producing transgenic plants having an increased pathogen resistance by altering the content and/or the activity of at least one ADF.

As has already been mentioned, altering the content and/or the activity of ADFs or of ADF3 can be conducted in different ways. If, in the following, ADFs are referred to in general, this will always include the ADF3 from barley. Increasing the ADF activity and the ADF content can be conducted, for example, by deactivating inhibitory regulation mechanisms on transcription, translation and protein level or by increasing the gene expression of a nucleic acid coding for at least one ADF or for functional homologs, parts, or mutants thereof, as compared to the wild-type. This can, for example, be conducted by inducing the respective endogenous ADF gene(s) or by introducing nucleic acids coding for ADFs or for functional homologs, parts, or mutants thereof.

In a preferred embodiment, the increase of the ADF activity or the ADF content in comparison to the wild-type is achieved by the increase of the gene expression of a nucleic acid coding for an ADF. In a further preferred embodiment, increasing the gene expression of a nucleic acid coding for an ADF is conducted by introducing nucleic acids coding for at least one ADF into the respective plant or plant cell. In principle, the ADF genes of the most diverse organisms, i.e. of any nucleic acid coding for an ADF with substantial homology to ADF3 from barley or to functional homologs, parts, or mutants thereof, can be used to this end. With genomic ADF nucleic acid sequences from eukaryotic sources, which contain introns, preferably already processed nucleic acid sequences like corresponding cDNAs are to be used in case the host organism is not capable or cannot be made capable of splicing the corresponding ADF sequences. All nucleic acids mentioned in this description can, for example, be an RNA, a DNA, or a cDNA sequence.

In a preferred method of the present invention for producing transgenic plants or plant cells with increased pathogen resistance, a nucleic acid sequence coding for at least one ADF is transferred to a plant or plant cell. This transfer leads to an increase in the expression or in the activity of ADF, respectively, as compared to the wild-type and, correspondingly, to an increase in pathogen resistance in the transgenic plants or plant cells. Such a method can be used in order to increase the expression of DNA sequences coding for ADFs or for their functionally equivalent homologs, parts, or functional mutants, thereby also increasing pathogen resistance in the transgenic plants or plant cells. The use of vectors comprising said sequences as well as regulatory sequences like promoter and termination sequences is known to the person skilled in the art.

According to the present invention, such a method typically comprises the following steps:
a) Production of a vector, comprising the following nucleic acid sequences in 5' to 3' orientation:
   a promoter sequence functional in plants,
   operatively linked thereto a DNA sequence coding for at least one ADF or for functionally equivalent homologs, parts, or mutants thereof,
   operatively linked thereto a termination sequence functional in plants
b) Transfer of the vector from step a) into a plant cell and, optionally, integration into the plant genome.

The person skilled in the art knows how to transfer a vector from step a) into plant cells and which characteristics a vector must have in order to be able to be integrated into the plant genome.

An example for the overexpression of a functional mutant of an ADF is the overexpression of HvADF3-$S^6$A (SEQ ID No. 2, see Examples). Due to the amino acid substitution of serine by alanine, the ADF3 cannot be phosphorylated in position 6 anymore. This yields a constitutively active form of ADF3. Thus, the overexpression of said mutant leads to both an increase in the content of ADF3 in the transgenic plants and to an increased activity of ADF3.

In case the ADF content in transgenic plants or plant cells is increased by transferring a nucleic acid coding for an ADF from another organism, like for example from *Dictyostelium discoideum*, it is recommendable to convert the amino acid sequence coded by the nucleic acid sequence from, for example, *Dictyostelium discoideum*, by re-translating the polypeptide sequence according to the genetic code to form a nucleic acid sequence, which in particular comprises such codons that are used more frequently due to organism-specific codon usage. Codon usage can easily be determined by computer evaluations of other known genes of the respective organisms.

According to the present invention, increasing the gene expression or the activity of a nucleic acid encoding an ADF is also understood to denote the manipulation of the expression of the endogenous ADFs inherent to the organism/s or plant/s. This can, for example, be achieved by altering the promoter DNA sequence for ADF coding genes. Such a modification, which leads to an altered, preferably increased, expression rate of at least one endogenous ADF gene, can be effected by deleting or inserting DNA sequences.

Modification of the promoter sequence of endogenous ADF genes usually leads to a modification of the expressed quantity of the ADF gene and thus also to a modification of the ADF activity detectable in the cell or plants.

Furthermore, an altered or increased expression of at least one endogenous ADF gene can be achieved by means of a regulator protein, which is not present in the transformed organism, interacting with the promoter of said genes. Such a regulator can be a chimeric protein, which consists of a DNA binding domain and a transcription activator domain, as is described, for example, in WO 96/06166.

It is a further possibility of increasing the activity and the content of endogenous ADFs to upregulate transcription factors, which are involved in the transcription of the endogenous ADF genes, for example, by overexpression. The measures for overexpressing transcription factors are known to the person skilled in the art and are also disclosed for ADFs within the scope of the present invention.

Moreover, an alteration of the activity of endogenous ADFs can be achieved by directed mutagenesis of the endogenous gene copies.

An alteration of the endogenous ADFs can also be achieved by influencing the post-translational modifications of ADFs. This can, for example, be done by regulating the activity of enzymes like kinases or phosphatases, which are involved in the post-translational modification of ADFs, by means of corresponding measures like overexpression or gene silencing.

The expression of endogenous ADFs can also be regulated via the expression of aptamers specifically binding to the promoter sequences of ADFs. Depending on whether the aptamers bind to stimulating or repressing promoter regions, the amount and thus, in this case, the activity of endogenous ADF is increased.

In the methods of the present invention for producing transgenic plants or plant cells with increased pathogen resistance, the reduction of the content and/or the activity of at least one ADF can be achieved by different strategies. The expression of at least one ADF in transgenic plants can, for example, be reduced by silencing.

In silencing, for example, a nucleic acid coding for at least one ADF or for parts thereof and/or being complementary to said ADF is transferred to the plant. In order to ensure that the plants are transgenic for the transferred nucleic acids, the nucleic acid to be transferred is usually transferred to the plant by means of a vector, like for example a plasmid, which is capable of stably replicating within the plant cell or of integrating the transferred nucleic acid into the plant genome.

Preferably, the RNAi method can be employed for the silencing of ADFs. Herein, for example, a vector comprising the following elements in 5' to 3' direction is transferred to the plant cell: a promoter being functional in plants; operatively linked thereto a DNA sequence comprising the antisense sequence of the sequence coding for the ADF or for parts thereof and having at its 3' end 3' exon sequences recognizable by the splicosome; an intron; a DNA sequence comprising the sense sequence of the DNA sequence coding for the ADF or for parts thereof and having at its 5' end 5' exon sequences, which can be recognized by the spliceosome; and a termination sequence. Such a vector is illustrated in FIG. 2. Of course, the position of the antisense and sense sequences can be interchanged. Herein, the person skilled in the art is aware of the fact that the respective 5' and 3' splicing sites have to be adapted correspondingly.

If such vectors are stably transferred to plant cells, the transcription of said vectors first yields a pre-mRNA consisting of a first exon, which comprises the antisense sequence of the sequence coding for the ADF or for parts thereof, an intron, and a second exon, which comprises the sense sequence of the DNA sequence coding for the ADF or for parts thereof. As the intron is removed by the splicing procedure, a continuous RNA molecule having regions, which are complementary to one another, is formed. Such an RNA molecule will develop a double-stranded structure (Smith et al., 2000, Nature, 407:319-320).

Such double-stranded RNA molecules are capable of specifically silencing the mRNA of ADFs by inducing the PTGS system, so that as a result the ADFs will not be expressed anymore. Herein, by the corresponding selection of antisense and sense sequences it can thus be determined which ADFs will not be expressed anymore. In this context, finding protein-characteristic sequences lies within the scope of the conventional knowledge of a person skilled in the art. It is known to the person skilled in the art that a multiplicity of ADFs can also be silenced by multiple use of the correspondingly characteristic sequences.

Such a method can, for example, comprise the following steps:
a) Production of a vector, comprising the following nucleic acid sequences in 5' to 3' orientation:
   a promoter sequence functional in plants,
   operatively linked thereto the identical or homologous antisense sequence of the sequence coding for at least one ADF or for parts thereof, wherein the sequence has at its 3' end 3' exon sequences, which can be recognized by the splicosome,
   operatively linked thereto an intron,
   operatively linked thereto the identical or homologous sense sequence of the sequence coding for at least one ADF or for parts thereof, wherein the sequence has at its 5' end 5' exon sequences, which can be recognized by the splicosome,
   operatively linked thereto a terminator sequence functional in plants,
b) Transfer of the vector from a) to plant cells and, optionally, integration into the plant genome.

It is also known to the person skilled in the art that, beside the mentioned vectors, other vectors can also be employed for the RNAi method or for PTGS. Such vectors can, for example, be constructed in such a way that the sense and antisense sequences are each transcribed starting from a U6 promoter, hybridize in the cell and induce the PTGS system (Tuschl, 2002, Nat. Biotechnol. 20, 446-448; Miyagishi et al., 2002, Nat. Biotechnol., 20, 497-500; Lee et al., 2002, Nat. Biotechnol., 20, 500-505). In other vectors, the sense and antisense sequences are connected via a loop sequence and are transcribed by a human RNAse P RNA H1 promoter. By means of folding back the loop, the sense and antisense sequences are capable of hybridizing, forming double-stranded RNA and inducing the PTGS system (Tuschl, 2002, vide supra; Paul et al., 2002, Nat. Biotechnol., 20, 505-508; Paddison et al., 2002, Genes Dev., 16, in press, Brummelkamp et al., 2002, Science, 296, 550-553). In a further embodiment of the RNAi method, not vectors, but rather pre-synthesized double-stranded RNA molecules having the previously described sense and antisense sequences, respectively, are introduced directly into the cell to be transfected, for example, by means of biolistic methods.

In a further embodiment, the vectors used for transferring the nucleic acids comprise, in 5' to 3' orientation, a promoter, operatively linked thereto a DNA sequence comprising the sequence coding for ADFs or for parts thereof and having self-complementary regions, and a termination sequence. When transcribing said vectors in the plant cell, RNA molecules having sequence regions, which are capable of self-hybridizing, are formed. Thus, double-stranded RNA molecules inducing the PTGS system can be present in the cell, which then leads to mRNA being specifically degraded by ADFs. Said method for silencing plant proteins, which is also referred to as co-suppression, requires that the mRNA of the ADF(s) to be suppressed has regions that are complementary to one another. Such regions can be identified by the person skilled in the art by means of simple visual inspection of the DNA sequence coding for the respective protein or by means of corresponding sequence programs, like for example DNAStar by DNASTAR Inc., Madison, USA.

Such a method can, for example, comprise the following steps:
a) Production of a vector, comprising the following nucleic acid sequences in 5' to 3' orientation:
   a promoter sequence functional in plants,
   operatively linked thereto the identical or homologous sense sequence of the sequence coding for the endogenous ADF(s) or for parts thereof, wherein the sequence has self-complementary regions,
operatively linked thereto a termination sequence functional in plants,
b) Transfer of the vector from a) to plant cells and, optionally, integration into the plant genome.

In a further embodiment of the present invention, the vectors used for transferring the nucleic acids comprise, in 5' to 3' orientation, a promoter, operatively linked thereto a DNA sequence comprising the antisense sequence of the sequence coding for ADFs or for parts thereof, and a termination sequence. When transcribing such vectors in plant cells, an RNA molecule is formed, whose sequence is complementary to the mRNA sequence coding for ADFs or for parts thereof. By hybridizing the antisense sequence with endogenous mRNA sequences of ADFs in vivo, the expression of ADFs in plant cells can thus be suppressed.

Such a method can, for example, comprise the following steps:
a) Production of a vector, comprising the following nucleic acid sequences in 5' to 3' orientation:
   a promoter sequence functional in plants,
   operatively linked thereto the identical or homologous antisense sequence of the sequence coding for the endogenous ADF(s) or for parts thereof,
   operatively linked thereto a termination sequence functional in plants,
b) Transfer of the vector from a) to plant cells and, optionally, integration into the plant genome.

In a further embodiment of the method of the present invention, vectors are used for transfer of the nucleic acids to the plant cells and which have, in 5' to 3' orientation, a promoter functional in plants, and operatively linked thereto a DNA sequence coding for a ribozyme, which specifically recognizes the mRNA of at least one ADF, and a termination sequence. The person skilled in the art knows how to produce ribozymes having endonuclease activity directed against a specific mRNA. This is, for example, described in detail in Steinecke et al. (1992, EMBO J., 11: 1525). Within the scope of the present invention, the term "ribozymes" is also understood to denote such RNA sequences, which, beside the actual ribozyme, further comprise leader sequences being complementary to the mRNA of the ADFs or to parts thereof and thus leading the mRNA-specific ribozyme to the mRNA substrate of the ribozyme in an even more directed manner.

Such a method comprises, for example, the following steps:
a) Production of a vector, comprising the following nucleic acid sequences:
   a promoter sequence functional in plants,
   operatively linked thereto a DNA sequence coding for a ribozyme, which specifically recognizes the mRNA of the endogenous ADF(s),
   operatively linked thereto a termination sequence functional in plants,
b) Transfer of the vector from a) to plant cells and, optionally, integration into the plant genome.

Another alternative for producing transgenic plants with increased pathogen resistance is provided by the transfer of nucleic acids by means of vectors comprising, in 5' to 3' orientation, a promoter functional in plants, operatively linked thereto a DNA sequence, which comprises antisense sequences of the sequences coding for ADFs or for parts thereof as well as the sequence coding for RNAse P, and a terminator sequence. When such vectors are transcribed, RNA molecules having a leader sequence (the antisense sequence), which directs the RNAse P to the mRNA of the ADFs, are formed in the cell, whereby cleavage of the mRNA is effected by RNAse P (U.S. Pat. No. 5,168,053). Preferably, the leader sequence comprises 10 to 15 nucleotides, which are complementary to the DNA sequence of the ADFs, and a 3'-NCCA nucleotide sequence, wherein N preferably is a purine. The transcripts of the external leader sequence bind to the target mRNA via the formation of base pairs, which allows cleavage of the mRNA by the RNAse P at the nucleotide, which is 5' from the paired region. Such a cleaved mRNA cannot be translated into a functional protein.

Such a method can, for example, comprise the following steps:
a) Production of a vector, comprising the following nucleic acid sequences in 5' to 3' orientation:
   a promoter sequence functional in plants,
   operatively linked thereto a DNA sequence complementary to the sequence coding for the mRNA of the endogenous ADF(s) or for parts thereof,
   operatively linked thereto a DNA sequence coding for ribonuclease P,
   operatively linked thereto a termination sequence functional in plants
b) Transfer of the vector from a) to plant cells and, optionally, integration into the plant genome.

Moreover, vectors containing a DNA sequence having, in 5' to 3' orientation, the following components: a DNA sequence corresponding to the 5' region of the DNA sequence coding for an ADF, a DNA sequence for a resistance gene, and a DNA sequence corresponding to the 3' region of the sequence coding for an ADF, can also be used for producing transgenic plants having increased pathogen resistance in accordance with the present invention. Such vectors can be used in order to effect a specific gene knockout of the ADF of interest via homologous recombination. In plant cells, in which the homologous recombination has taken place, the sequence for the resistance gene is inserted into the DNA coding for the ADF, so that functional mRNA of the ADF cannot be produced in the cell anymore. By means of selection against the resistance gene, the plant cells, in which the recombination has taken place, can be identified. It is known to the person skilled in the art how to individually construct such vectors for gene knockout by homologous recombination, which elements they need to comprise (promoters, enhancers, flanking sequences), and how the plant cells of the knockout are identified. Typically, antibiotics resistance genes are used as resistance genes. Of course, other resistance genes allowing selection of those cells, in which the recombination has taken place, can also be used.

Such a method can, for example, comprise the following steps:
a) Production of a vector, comprising the following nucleic acid sequences in 5' to 3' orientation:
   a promoter sequence functional in plants,
   operatively linked thereto a DNA sequence identical or homologous to the sequence(s) coding for the 5' end of the endogenous ADF(s),
   operatively linked thereto a DNA sequence coding for a resistance gene,
   operatively linked thereto a DNA sequence identical or homologous to the sequence(s) coding for the 3' end of the endogenous ADF(s),
   operatively linked thereto a termination sequence functional in plants,
b) Transfer of the vector from a) to plant cells and integration into the plant genome.

If nucleic acid sequences coding for ADFs or for parts thereof are mentioned within the scope of the present invention, this is understood to denote both the complete coding DNA sequence of the ADFs and the complete mRNA sequence or the respective partial regions. As some of the previously mentioned methods for producing transgenic plants, in which the expression of ADFs is significantly reduced, are based on the fact that a specific hybridization between the endogenous mRNA of ADFs and the sequences, which form upon transcription of the previously mentioned vectors, takes place (like for example the antisense strategy), it is known to the person skilled in the art that the nucleic acids transferred do not always have to contain the entire sequence coding for the ADFs, irrespective of whether it is the sense or the antisense sequence. For a specific hybridization, relatively short regions of the sequences coding for ADFs can rather be already sufficient for efficient silencing.

With vectors, whose transcription leads to double-stranded RNA molecules, it is sufficient if the sequences corresponding to the sequence regions of the mRNA of ADFs finally lead to double-stranded RNA molecules of about 25 nucleotides, preferably 21, 22, or 23 nucleotides, in length. Normally, the sequences transferred with the antisense strategy comprise between 20 and 1,000 nucleotides, preferably between 20 and 750 nucleotides, particularly preferably about 400 to 800 and 500 to 750 nucleotides. However, sequences comprising between 20 and 500 nucleotides, between 20 and 300 nucleotides, between 20 and 150 nucleotides, and between 20 and 100 or 20 and 50 nucleotides, can also be used.

It is known to the person skilled in the art that in RNAi or PTGS the sense and antisense RNAs used for developing double-stranded RNA molecules can also comprise about 21, 22, or 23 nucleotides with a characteristic 3' overhang (Tuschl, 2002, Nat. Biotechnol. 20, 446-448).

If nucleic acids, whose transcription in the cell leads to sequences complementary to the mRNA of ADFs (like for example in the antisense strategy), are transferred to the plant cells, said sequences then do not have to be 100% complementary to the mRNA. It is rather sufficient if said sequences have a complementarity of at least 50%, preferably of at least 60%, especially preferably of at least 70%, also especially preferably of at least 80%, in particular preferably of at least 90%, and most preferably of at least 95%. Herein, deviations may have been caused by deletion, substitution, and/or insertion. Of course, it is obvious for the person skilled in the art that the probability of more ADFs being silenced increases as complementarity decreases.

In general, it applies that only those complementary sequences can be used in accordance with the present invention, which are capable of specifically hybridizing with mRNA regions of ADFs. Sequences hybridizing in vivo to RNA regions of proteins other than ADFs and causing the silencing of the latter are not suitable for the methods according to the present invention. Depending on the sequence selected and the degree of complementarity, many or only a few ADFs will be silenced. It is possible that the expression of only one particularly specific ADF is inhibited. Preferably, complementary sequences have a length of between 20 and 1,000 nucleotides, also preferably of between 20 and 750 nucleotides, especially preferably of between 20 and 500 nucleotides, also especially preferably of between 20 and 300 nucleotides, particularly preferably of between 20 and 150 nucleotides, also particularly preferably of between 20 and 75 nucleotides, and most preferably of about 20 to 50 nucleotides. It is also possible that the sequences comprise only about 20 or 25 nucleotides.

Some of the previously mentioned methods can also be conducted with sequences that are not components of the coding part of the mRNA of ADFs or are not complementary thereto. It can, for example, be sufficient if said sequences are sequences from the 5' or 3' untranslated region, provided that these regulatory sequences are characteristic for the mRNA of the respective ADF.

Such sequences can, in particular, be used in case silencing is induced by double-stranded RNA constructs or the translation of a mRNA is inhibited by antisense constructs. Thus, according to the present invention, the term mRNA does not only comprise the coding components of the mRNA of ADFs, but also all regulatory sequences occurring in pre-mRNA or mature mRNA and that are characteristic for the mRNA of the ADFs. Correspondingly, this also applies to the DNA sequence. This relates to, for example, 5' and 3' untranslated regions, promoter sequences, upstream activating sequences, introns, etc.

If vectors are employed, whose transcription leads to RNA molecules consisting of a leader sequence and RNAse P, the leader sequence has to be sufficiently complementary in order to specifically recognize the ADF. The region of the mRNA of the ADF, which will be recognized by the leader sequence, can be selected according to the respective requirements. Preferably, such leader sequences comprise about 20 nucleotides; they should, however, not be significantly shorter than 15 nucleotides. With a 100% complementarity of the leader sequence, 12 nucleotides should also be sufficient. Of course, the leader sequences can comprise up to 100 nucleotides or more, as this will merely increase their specificity for the respective mRNA.

If, within the scope of the present invention, sense sequences are mentioned, this is understood to denote those sequences corresponding to the coding strand of the genes for ADFs or comprising parts thereof. However, such sequences do not have to be 100% identical to the sequences coding for the ADFs of interest. It is sufficient if the sequences are sufficiently similar to the sequences coding for ADFs in such a way that their expression in plant cells leads to efficient and specific silencing of the ADFs in the cell, for example, by RNA interference or co-suppression.

It should suffice if said sequences are identical by at least 50%, preferably by at least 60%, especially preferably by at least 70%, further especially preferably by at least 80%, in particular preferably by at least 90%, and most preferably by at least 95%. With such degrees of identity, the sequences are, in accordance with the present invention, referred to as being homologous to one another or as having a homology (vide supra). Herein, the deviations as compared to the sequences coding for the ADFs or for parts thereof can be caused by deletion, addition, substitution, and/or insertion. Of course, it is obvious to the person skilled in the art that the probability of more ADFs being silenced increases as identity decreases. Sequences, whose degree of identity or homology is low to such an extent that proteins other than ADFs are being silenced, are not sufficiently specific and are therefore not suitable for the methods according to the present invention.

If, correspondingly, antisense sequences are mentioned, this is, in accordance with the present invention, understood to denote those sequences corresponding to the non-coding strand of the genes of the ADFs of interest. Of course, said sequences neither have to be 100% identical to the sequence of the non-coding DNA strand of the genes of the respective ADFs of interest, but they can have the previously mentioned degrees of homology. These facts are also reflected in the circumstance that antisense sequences complementary to the mRNA of a gene according to definition do not have to be 100% complementary to said mRNA. They can, for example, also be complementary by at least 50%, preferably by at least 60%, especially preferably by at least 70%, further especially preferably by at least 80%, in particular preferably by at least 90%, and most preferably by at least 95%, 98%, and/or 100%. As has been explained in the above, it is sufficient if the antisense sequences are capable of specifically hybridizing to the mRNA of ADFs that is of interest in each case. Hybridization can occur either in vivo under cellular conditions or in vitro.

Hybridization of an antisense sequence with an endogenous mRNA sequence typically occurs in vivo under cellular conditions or in vitro.

Moreover, the terms "sense" and "antisense" are known to the person skilled in the art. Correspondingly, the person skilled in the art of silencing genes in plants is aware of how large the nucleic acid molecules used for silencing have to be and which homology or complementarity to the sequences of respective interest they need to have. According to the present invention, antisense sequences, which are not capable of, for example, specifically hybridizing with coding sense sequences of ADFs in vivo and/or in vitro, i.e. which also hybridize with the coding sense sequences of other protein classes, cannot be used.

In principle, the antisense strategy can be coupled with a ribozyme method. Ribozymes are catalytically active RNA sequences, which, if coupled to the antisense sequences, catalytically cleave the target sequences (Tanner et al., (1999) FEMS Microbiol Rev. 23 (3), 257-75). This can increase the efficiency of an antisense strategy.

Further methods for reducing the expression of ADFs, in particular in plants as organisms, comprise overexpression of homologous ADF nucleic acid sequences, which leads to co-suppression (Jorgensen et al., (1996) Plant Mol. Biol. 31 (5), 957-973), or the induction of specific RNA degradation by the plant with the aid of a viral expression system (Amplikon) (Angell et al., (1999) Plant J. 20 (3), 357-362). Said methods are also referred to as "post-transcriptional gene silencing" (PTGS) (vide supra).

Further methods are: introducing nonsense mutations into the endogenous gene via introducing RNA/DNA oligonucleotides into the plant (Zhu et al., (2000) Nat. Biotechnol. 18 (5), 555-558) or generating knockout mutants with the aid of, for example, T-DNA mutagenesis (Koncz et al., (1992) Plant Mol. Biol. 20 (5) 963-976) or homologous recombination (Hohn et al., (1999) Proc. Natl. Acad. Sci. USA. 96, 8321-8323.).

Furthermore, gene repression (but also gene overexpression) is also possible with specific DNA-binding factors, for example factors of the type of zinc finger transcription factors. Furthermore, factors inhibiting the target protein itself can be introduced into a cell. The protein-binding factors can, for example, be aptamers (Famulok et al., (1999) Curr Top Microbiol Immunol. 243, 123-36).

Reduction can also be performed by aptamers. Aptamers can also be designed in such a way that they specifically bind to the ADF proteins and, for example, reduce the activity of the ADFs by binding to the catalytic center of the ADFs. Usually, the expression of aptamers is conducted by vector-based overexpression and is, as well as the design and selection of aptamers, well known to the person skilled in the art (Famulok et al., (1999) Curr Top Microbiol Immunol., 243, 123-36).

A good survey relating to some of the methods described in the above can be found, for example, in Waterhouse et al., (2001), Nature 411, 834-842; Tuschl (2002), Nat. Biotechnol. 20, 446-448 and further publications of this edition, Paddison et al., (2002), Genes Dev., 16, 948-958; Brummelkamp et al., (2002), Science 296, 550-553).

ADF-specific antibodies can be considered as further protein-binding factors, whose expression in plants causes a reduction in the content and/or in the activity of ADFs. The production of monoclonal, polyclonal, or recombinant ADF-specific antibodies follows standard protocols (Guide to Protein Purification, Meth. Enzymol. 182, pp. 663-679 (1990), M. P. Deutscher, ed.). The expression of antibodies is also known from the literature (Fiedler et al., (1997) Immunotechnology 3, 205-216; Maynard und Georgiou (2000) Annu. Rev. Biomed. Eng. 2, 339-76). This approach will be illustrated in detail further below.

In a further method of the present invention for producing transgenic plants having increased pathogen resistance it is intended to reduce the activity of endogenous ADFs by expressing non-functional mutants of ADFs in the plant or in the plant cells. By introducing such non-functional mutants, which preferably are dominant-negative mutants, the interaction of the endogenous ADFs with their cellular binding partners is inhibited. By introducing non-functional mutations into the endogenous ADFs, plants and plant cells having an increased pathogen resistance can also be produced in accordance with the present invention. According to the present invention, non-functional mutants are understood to denote ADFs forms that contain mutations, which prevent the ADFs from interacting with G-actin, F-actin, components of the pathogen, and/or with other physiological binding partners.

If such dominant-negative mutants are expressed or over-expressed in the transgenic cell or plant, they are capable of competing with the interaction of the pathogen components with wild-type ADFs or the interaction of wild-type ADFs with the other physiological factors, like for example actin, so that the pathogen will have no possibility of propagating. It is surprising that with said method it is possible to produce transgenic plants having an increased pathogen resistance while simultaneously exhibiting a substantially normal phenotype, although such dominant-negative mutants should influence the endogenous cytoskeleton of the plant cell.

The person skilled in the art is aware of the fact that transgenic plants or plant cells according to the present invention can not only be produced by expressing or overexpressing dominant-negative mutants of ADFs from plants, like ADF3, but, of course, also by expressing or overexpressing dominant-negative mutants of ADFs from other organisms. Herein, ADFs from eukaryotes like yeasts (for example *S. cerevisiae*), *C. elegans*, or higher mammals like mice, rats, or humans can be considered. It is prerequisite that the expression of said dominant-negative mutants causes a competition of the endogenous plant ADFs with pathogen components and/or their cellular interaction partners. The ADFs from other organisms can be identified by the previously described database analyses and homology comparisons. It is prerequisite that they have a region or regions homologous to the consensus sequences mentioned in the above.

Transgenic plants expressing dominant-negative mutants of ADFs can be produced by transferring a corresponding expression vector to plant cells.

Such a method can, for example, comprise the following steps:

a) Production of a vector, comprising the following nucleic acid sequences in 5' to 3' orientation:
   a promoter sequence functional in plants,
   operatively linked thereto a DNA sequence coding for a dominant-negative mutant of a plant ADF,
   operatively linked thereto a termination sequence functional in plants,
b) Transfer of the vector from a) to the plant cells and, optionally, integration into the plant genome.

Non-functional mutants, which are dominant-negative mutants of ADFs, can be identified by the person skilled in the art by simple routine experimentation. On the one hand, as has already been mentioned in the above, a variety of mutations, for example from the ADF3 of maize, are known, which inhibit the interaction with F-actin or G-actin. These are mutations, in which the tyrosine moieties in the positions 67 and 70 of ADF3 from maize are substituted by phenylalanine. By means of so-called sequence alignments, the positions equivalent to the tyrosine 67 and 70 positions, for example in ADF3 from barley or other ADFs, can be determined and, similarly, mutations can be generated in this manner. The ADF3 from barley can be, for example, the positions phenylalanine 66 and phenylalanine 69. These can, for example, be substituted by alanine.

Mutations inhibiting the interaction of ADFs with G-actin, F-actin, other physiological binding partners, and/or pathogen components can be easily determined by generating recombinant ADF proteins containing a different mutation and/or deletion, and testing said recombinant proteins in binding assays with the previously mentioned components.

In the same manner, for example in in vitro binding tests, it can be tested whether dominant-negative mutants of ADF proteins, and preferably of ADF3 from barley, are capable of competing with the interaction of the ADF with G-actin, F-actin, other cellular binding partners, and/or pathogen components.

The term "dominant-negative mutations" is understood to denote all types of mutations, i.e. insertion, deletion, and point mutation, which are capable of preventing the interaction of ADFs with G-actin, F-actin, other cellular binding partners, and/or pathogenic components.

In the method according to the present invention for producing transgenic plants with increased pathogen resistance by expressing dominant-negative mutants of ADFs, a modulation of the interaction degree between the endogenous ADFs with their binding partners and no silencing of the host factors takes place, which results in the additional advantage that said mechanism does not provide a point of direct attack for pathogen-coded suppressors.

It is known to the person skilled in the art how (a) point mutation(s), (an) insertion mutation(s), or (a) deletion mutation(s) can be introduced into the nucleic acid sequences coding for ADFs. PCR techniques can be preferred, for example, for introducing point mutations ("PCR technology: Principle and Applications for DNA Amplification", H. Ehrlich, id, Stockton Press). In addition, examples for introducing point mutations into DNA sequences coding for ADF3 can be found in the appended Examples.

Transgenic plants or plant cells with an increased pathogen resistance can, according to the present invention, also be produced in such a way that, for example, a recombinant antibody, which specifically blocks or competes the interaction of ADFs (and preferably of ADF3 from barley) with G-actin, F-actin, other cellular binding partners, and/or pathogen components, is expressed in the plants.

The ways, by which such recombinant antibodies can be isolated and identified against, for example, a specific domain of ADFs are known to the person skilled in the art and can be taken from the literature (Harlow et al., 1999, Using antibodies: a laboratory manual, Cold Spring Harbor Laboratory Press).

According to the present invention, recombinant antibodies are understood to denote the different known forms of recombinant antibodies as described, for example, in Skerra et al. (Curr. Opin. Immunol. (1993) 2, 250-262). Herein, the recombinant antibodies according to the present invention comprise the so-called Fab fragments, Fv fragments, scFv antibodies, scFv homodimers, which are connected via disulfide bridges to one another, as well as so-called VH chains. The Fab fragments consist of assembled complete light chains and truncated heavy chains, whereas Fv fragments consist of non-covalently linked VH and VL chains. A survey of the fragments and recombinant antibodies mentioned can be found in Conrad et al. (Plant Mol. Biol. (1998) 38, 101-109). The Fab and Fv fragments mentioned are capable of associating with one another in vivo.

As it is possible that this process does not run very efficiently, the use of scFv antibodies is preferred according to the present invention. Said antibodies consist of the variable portion of the light chain and the variable portion of the heavy chain, which are fused via a flexible linker peptide. The production of such scFv antibodies has been intensively described in the prior art (see, inter alia, Conrad et al., vide supra; Breitling et al. (1999) Recombinant Antibodies, John Wiley & Sons, New York). The scFv antibodies have the same antigen specifity and activity as normal antibodies; however, they do not have to be assembled in vivo from individual chains like other natural or recombinant antibodies. They are thus in particular suitable for the methods of the present invention.

In the previously mentioned references, it is illustrated in detail how nucleic acid sequences coding for the scFv antibodies preferred according to the present invention can be isolated and produced by the person skilled in the art.

Conventionally, it is assumed herein from existing hybridoma cell lines, which produce monoclonal antibodies. Subsequently, the cDNAs coding for the light and the heavy chains of the antibody are isolated and, in a second step, the coding regions for the variable region of the light and the heavy chain are fused to one another to form one molecule.

A further way of generating recombinant antibodies, which is known to the person skilled in the art, is the screening of libraries of recombinant antibodies (so-called "phage display libraries", see also Hoogenboom et al. (2000) Immunology Today 21, 371-378; Winter et al. (1994) Annu. Rev. Immunol. 12, 433-455; De Wildt et al. (2000) Nat. Biotechnol. 18, 989-994). In said method it is possible, by means of procedures known to the person skilled in the art, to enrich, select, and isolate recombinant antibodies against a given antigen.

A method for expressing antibodies against ADFs can, for example, comprise the following steps:
a) Production of a vector, comprising the following nucleic acid sequences in 5' to 3' orientation:
   a promoter sequence functional in plants,
   operatively linked thereto a DNA sequence coding for a recombinant antibody, which is specific for the endogenous ADF(s) and/or blocks the interactions with physiological binding partners, preferably with G-actin and/or F-actin,
   operatively linked thereto a termination sequence functional in plants,
b) Transfer of the vector from a) to plant cells and, optionally, integration into the plant genome.

A further object of the present invention relates to plant cells and plants, in which the endogenous genes of ADFs have mutations, i.e. substitutions, insertions, and/or deletions, which lead to the result that the expressed endogenous ADFs are not, or only in a limited manner, capable of interacting with pathogen factors and/or their endogenous cellular binding partners anymore. Plants or plant cells containing endogenous gene copies having such mutations will have, like the previously described transgenic plants or plant cells, increased transient or permanent pathogen resistance to the previously mentioned viral groups and strains. Such plants and plant cells, which are not transgenic as opposed to the plants and plant cells mentioned in the above, can be generated by classical mutagenesis.

According to the present invention, such non-transgenic plants or plant cells must have, however, the previously mentioned types of mutations, which lead to a modulation of the expression of the endogenous ADFs and/or of the binding behavior of the endogenous ADFs, in the genes coding for endogenous ADFs. Modulation of the expression of the endogenous ADFs, can, for example, mean that the expression of the endogenous ADFs is down-regulated by mutations in regulatory DNA elements of the genes of the endogenous ADFs, like for example promoters, enhancers, or sequences generally referred to as "upstream activating sequences".

Within the scope of the present invention, modulation of the binding behavior of ADFs is understood to denote that the previously mentioned types of mutations lead to an alteration in the binding behavior of the endogenous ADFs with respect to the pathogenic factors and/or the normal cellular binding partners. A modulation of the binding behavior of the endogenous ADFs is preferred, which leads to the fact that no or merely limited interaction of said ADFs with pathogen factors and/or their cellular partners takes place. A combination of the modulation of expression and binding behavior of the endogenous ADFs is also conceivable.

Plants or plant cells can, for example, have mutations in the gene sequences for endogenous ADFs, which lead to a reduction of the expression of said proteins. Other plants or plant cells contain mutations leading to the previously described dominant-negative mutants. In both cases, plants with an increased pathogen resistance are obtained.

The person skilled in the art is aware of the fact that, by means of mutagenesis, it is also possible to produce, for example, plants or plant cells which, due to mutations in enhancer and/or promoter sequences of the genes for endogenous ADFs, exhibit a reduction in expression of said proteins and at the same time have mutations in the coding regions of the genes coding for endogenous ADFs, which have the effect that the remaining expressed ADFs are not, or only in a limited manner, capable of interacting with the pathogenic and/or other cellular binding partners anymore. Vice versa, corresponding mutations in enhancer and/or promoter sequences and in the coding sequences can have the effect that a previously illustrated dominant-negative mutant of endogenous ADFs, which is not, or only in a very limited manner, capable of interacting with pathogenic and/or normal cellular interaction partners anymore, is overexpressed and that the competition reaction described in the above will thus take place.

Said plants are characterized by an increased transient or permanent pathogen resistance to the previously mentioned pathogens.

Preferably, the non-transgenic plants and plant cells according to the present invention, which are characterized by a modulation of the expression and/or of the binding behavior of the endogenous ADFs and which have a permanent or transient pathogen resistance, can be produced by the so-called "TILLING" (Targeting Induced Local Lesion in Genomes) approach. Said method has been described in detail in Colbert et al. (2001, Plant Physiology, 126, 480-484), McCallum et al. (2000, Nat. Biotechnol., 18, 455-457) and in McCallum et al. (2000, Plant Physiology, 123, 439-442). The previously mentioned references are explicitly incorporated herein as disclosure with respect to the "TILLING" method.

The TILLING method is a strategy of so-called reverse genetics, which combines the production of high densities of point mutations in mutagenized plant collections, for example by chemical mutagenesis with ethylmethane-sulfonate (EMS), with fast systematic identification of mutations in target sequences. First, the target sequence is amplified via PCR in DNA pools of mutagenized M2 populations. Denaturing and annealing reactions of the heteroallelic PCR products allow the formation of heteroduplexes, wherein one DNA strand originates from the mutated and the other strand from the wild-type PCR product. At the site of the point mutation, a so-called mismatch occurs, which can be identified either via denaturing HPLC (DHPLC, McCallum et al., 2000, Plant Physiol., 123, 439-442) or via the CelI mismatch detection system (Oleykowsky et al., 1998, Nucl. Acids Res. 26, 4597-4602). CelI is an endonuclease recognizing mismatches in heteroduplex DNA and cleaving the DNA specifically at these sites. The cleavage products can then be separated and detected via automated sequencing gel electrophoresis (Colbert et al., 2001, vide supra). After identifying target gene-specific mutations in a pool, individual DNA samples are correspondingly analyzed in order to isolate the plant bearing the mutation. In this manner, identification of the mutagenized plant cells or plants is conducted in the plants and plant cells of the present invention subsequently to the production of the mutagenized plant populations using primer sequences directed against ADF3 or ADFs. In general, the TILLING method is applicable to all plants and therefore the cultured and useful plants mentioned in the above are suitable for the method according to the present invention.

Beside the nucleic acid sequence to be transferred, the vectors used for expressing or silencing ADFs comprise further regulatory elements. Which actual regulatory elements said vectors have to contain depends each on the method to be conducted with these vectors. The person skilled in the art, who is familiar with the different methods mentioned in the above for producing transgenic plants, in which the expression of a protein is inhibited, knows which regulatory elements and also other elements have to be contained in said vectors.

The term "operatively linked" is understood to denote that the sequences linking the different used nucleic acids are selected in such a way that the function of the respectively linked nucleic acid segment is maintained. In case, for example, the coding sequences of ADF3 are to be expressed in a cell, it has to be observed that no sequences, which would lead to a termination of the transcription, are located between the promoter sequence and the coding sequence for ADF3.

Typically, the regulatory elements contained in the vectors are such elements ensuring transcription and, if desired, translation in the plant cell. Such elements can also effect a targeted localization of the proteins in specific cell types or cell organelles, however. This can, for example, be achieved by using promoters specific for epidermal cells.

The nucleic acid sequences to be transferred can thus be, for example, under the control of promoters functional in plants. Said promoters can be constitutive promoters, but they can also be inducible or specific for tissue or specific for developmental stages. Furthermore, they can also be fungus-specific promoters.

Typically, the constitutive 35S promoter will be used as promoter for vectors. Moreover, further promoters can, of course, also be used, which are obtained from different sources, like for example from plants or plant viruses, and which are suitable for the expression of genes in plants. Herein, the selection of the promoter as well as of other regulatory sequences determines the spatial and temporal expression pattern and therefore also the expression or the silencing of the ADFs in transgenic plants.

Beside further constitutive promoters, like for example the actin promoter (McElroy et al., 1990, Plant Cell, 2:163) and the ubiquitin promoter (Binet et al., 1991, Plant Science, 79:87), the promoters of phosphoenolpyruvate carboxylase from maize (Hudspeth et al., 1989, Plant Mol. Biol., 12:579) or of fructose-1,6-bisphosphatase from potato (WO 98/18940), which mediate leaf-specific expression, are also candidates as tissue-specific promoters. Wound-, light- or pathogen-induced promoters as well as other development-dependent promoters or control sequences can also be used (Xu et al., 1993, Plant Mol. Biol. 22:573; Logemann et al., 1989, Plant Cell, 1:151; Stockhaus et al., 1989, Plant Cell, 1:805; Puente et al., 1996, EMBO J., 15:3732; Gough et al., 1995, Mol. Gen. Genet., 247:323). A summary of usable control sequences can be found, for example, in Zuo et al., 2000, Curr. Opin. Biotech., 11:146.

Suitable promoters also comprise promoters ensuring an expression only in photosynthetically active tissues, like for example the ST-LS1 promoter (Stockhaus et al. (1987) Proc. Natl. Acad. Sci. USA 84:7943-7947; Stockhaus et al. (1989) EMBO J. 8:2445-2451). Promoters, which are active during plant transformation, plant regeneration, or specific stages of said processes, can also be used, like for example promoters specific during cell division, like the histone H3 promoter (Kapros et al. (1993) In Vitro Cell Cev. Biol. Plant 29:27-32) or the chemically inducible Tet repressor system (Gatz et al. (1991) Mol. Gen. Genet. 227:229-237). Further suitable promoters can be taken from the literature, for example Ward (1993, Plant Mol. Biol. 22:361-366). The same applies to inducible and cell- or tissue-specific promoters, like meristem-specific promoters, which have also been described in the literature and are also suitable within the scope of the present invention.

Further inducible promoters comprise virus-inducible promoters, like the ACMV virion sense promoter (Hong et al., 1996, Virology, 220:119-227), which is induced by the gene product AC2. Furthermore, all promoters of such proteins, which are induced in virus-infected tissue, like for example phenylalanine ammonium lyase, chalcone synthase, hydroxyproline-rich glycoprotein, extensin, pathogenesis-related proteins (for example PR-1a), and wound-inducible protease inhibitors (U.S. Pat. No. 6,013,864), are suitable.

Moreover, the person of average skill in the art is capable of isolating further suitable promoters using routine methods. Thus, the person skilled in the art is capable of identifying storage organ-specific regulatory nucleic acid elements by conventional molecular-biological methods, like for example hybridization experiments or DNA protein binding studies. Herein, for example, in a first step, the entire poly(A)$^+$ RNA is isolated from storage organ tissue of the desired organism, from which the regulatory sequences are to be isolated, and a cDNA bank is established. In a second step, those clones, whose corresponding poly(A)$^+$ RNA molecules accumulate only in the tissue of the storage organ, are identified from the first bank by means of hybridization with the aid of cDNA clones based on poly(A)$^+$ RNA molecules from non-storage organ tissue. Subsequently, with the aid of said cDNAs thus identified, promoters are isolated, which have storage organ-specific regulatory elements. Moreover, the person skilled in the art has at his disposal further methods based on PCR for isolating suitable storage organ-specific promoters.

In a further embodiment, the promoter is the promoter of the class I patatin gene B33 from potato. Further preferred promoters are those that are, in particular, active in fruits. Among those are, for example, the promoter of a polygalacturonase gene, for example from tomato, which mediates expression during ripening of tomato fruits (Nicholass et al. (1995) Plant Mol. Biol. 28:423-435; this prior art document describes the analysis of promoter/GUS fusion constructs), the promoter of an ACC oxidase, for example from apple, which mediates ripening- and fruit-specifity in transgenic tomatoes (Atkinson et al. (1998) Plant Mol. Biol. 38:449-460; this prior art document also discloses promoter/GUS expression analyses), or the 2A11 promoter from tomato (van Haaren et al. (1991) Plant Mol. Biol. 17:615-630, also describes promoter/GUS fusions).

As well in the case of fruit-specific promoters, the person skilled in the art can select further suitable promoters described in the literature or isolate them, as has been described in the above for storage organ-specific promoters, using routine methods.

It is known to the person skilled in the art that the use of inducible promoters allows the production of plants and plant cells expressing or silencing the sequences of the present invention only transiently. Such a transient expression allows the production of plants exhibiting only a transient pathogen resistance. Such a transient resistance can, for example, be desirable in case there is the danger of a pathogen contamination and the plants therefore have to be resistant to the pathogen only for a specific time period. Further situations, in which a transient resistance is desirable, are known to the person skilled in the art. Moreover, it is known to the person skilled in the art that he can achieve a transient expression or a transient silencing and a transient resistance by means of using vectors not stably replicating in plant cells and containing the corresponding sequences for expression or silencing of ADFs.

In other cases, it can also be ensured by selecting a corresponding vector that the transfection of the transgenic plants takes place only transiently. It is known to the person skilled in the art what kind of vectors are suitable for a transient transfection and those to be used for a stable transfection.

The vectors according to the present invention can, in addition, also comprise, for example, enhancer elements as regulatory elements. They can further contain resistance genes, replication signals, and further DNA regions, which allow propagation of the vectors in bacteria like, for example, *E. coli*. The regulatory elements also comprise sequences effecting a stabilization of the vectors in the host cells. In particular, such regulatory elements comprise sequences allowing a stable integration of the vector into the host genome of the plant or an autonomous replication of the vector in the plant cells. Such regulatory elements are known to the person skilled in the art.

The so-called termination sequences or terminators are sequences ensuring that transcription or translation is terminated properly. In case the transferred nucleic acids are to be translated, the terminators will typically be stop codons and corresponding regulatory sequences. In case the transferred nucleic acids are only to be transcribed, they will normally be poly A sequences.

According to the present invention, vectors are understood to denote plasmids, cosmids, viruses, and other vectors well-established in gene technology, by means of which it is possible to transfer nucleic acid molecules to plants or plant cells.

A large number of cloning vectors containing a replication signal for *E. coli* and a marker gene for selecting transformed bacterial cells are available for preparing the introduction of foreign genes into higher plants or their cells. Examples for such vectors are pBR322, pUC series, M13 mp series, pACYC184, and so on. The desired sequence can be introduced into the vector at a suitable restriction site. The plasmid obtained is used for the transformation of *E. coli* cells. Transformed *E. coli* cells are cultivated in a suitable medium and then harvested and lysed. The plasmid is recovered. In general, restriction analyses, gel electrophoreses, and further biochemical/molecular-biological methods are used as analytic methods for characterizing the obtained plasmid DNA. After each manipulation, the plasmid DNA can be cleaved and the DNA fragments obtained can be linked to other DNA sequences. Each plasmid DNA sequence can be cloned in the same or in different plasmids. Standard cloning methods can be taken from Sambrook et al., 2001 (Molecular cloning: A laboratory manual, 3rd edition, Cold Spring Harbor Laboratory Press).

A variety of known techniques for introducing DNA into a plant host cell are available, wherein the person skilled in the art may easily choose the method suitable in each case. Said techniques comprise the transformation of plant cells with T-DNA using *Agrobacterium tumefaciens* or *Agrobacterium rhizogenes* as transforming agent, the fusion of protoplasts, the direct gene transfer of isolated DNA into protoplasts, the electroporation of DNA, the introduction of DNA by means of the biolistic method, as well as further possibilities. Herein, both stable and transient transformants can be generated.

With respect to injection and electroporation of DNA into plant cells, no special requirements per se are made on the plasmids used. In a similar manner, this applies to direct gene transfer. Simple plasmids, like for example pUC derivatives, can be employed. If, however, whole plants are to be regenerated from cells transformed in such a manner, the presence of a selectable marker gene is required. The current selection markers are known to the person skilled in the art and selecting a suitable marker will not pose any problem to him. Common selection markers are such markers mediating resistance against a biocide or an antibiotic, like kanamycin, G418, ampicillin, bleomycin, hygromycin, methotrexate, glyphosate, streptomycin, sulfonyl urea, gentamycin, or phosphinotricin and the like, to the transformed plant cells.

Depending on the method for introducing desired genes into the plant cell, further DNA sequences may be required. If, for example, the Ti or Ri plasmid is used to transform the plant cell, at least the right border, though often both the right and the left border of the T-DNA contained in the Ti and Ri plasmid, has to be linked with the genes to be introduced as a flanking region.

In case agrobacteria are used for the transformations, the DNA to be introduced has to be cloned into special plasmids, in fact either into an intermediary or into a binary vector. Due to sequences, which are homologous to sequences in the T-DNA, the intermediary vectors can be integrated into the Ti or Ri plasmid of the agrobacteria by means of homologous recombination. Said plasmid further contains the vir region required for transferring the T-DNA. Intermediary vectors are not able to replicate in agrobacteria. By means of a helper plasmid, the intermediary vector can be transferred to *Agrobacterium tumefaciens* (conjugation). Binary vectors are able to replicate both in *E. coli* and in agrobacteria. They contain a selection marker gene and a linker or polylinker, which are framed by the right and left T-DNA border region. They can be transformed directly into agrobacteria (Holsters et al. (1978), Molecular and General Genetics 163, 181-187). The *Agrobacterium* serving as host cell is supposed to contain a plasmid bearing a vir region. The vir region is required for the transfer of the T-DNA into the plant cell. T-DNA can also be present. The *agrobacterium* transformed in such a way is used for the transformation of plant cells.

The use of T-DNA for transforming plant cells has been intensively studied and sufficiently described in EP 120 515.

For the transfer of the DNA into the plant cell, plant explants can be appropriately cultivated with *Agrobacterium tumefaciens* or *Agrobacterium rhizogenes*. From the infected plant material (for example leaf pieces, stem segments, roots, but also protoplasts or suspension-cultivated plant cells), whole plants can then again be regenerated in a suitable medium, which can contain antibiotics or biocides for selecting transformed cells. Regenerating the plants is conducted according to conventional regeneration methods using known nutrient media. The plants or plant cells thus obtained can then be examined for the presence of the introduced DNA.

Other possibilities of introducing foreign DNA using the biolistic method or by means of protoplast transformation are known to the person skilled in the art (cf. L. Willmitzer (1993) Transgenic Plants in: Biotechnology, A Multi-Volume Comprehensive Treatise (editor: H. J. Rehm et al.), Volume 2, 627-659, VCH Weinheim, Germany).

While the transformation of dicotyledonous plants or cells thereof via Ti plasmid vector systems with the aid of *Agrobacterium tumefaciens* is well established, more recent works indicate that also monocotyledonous plants or cells thereof are positively accessible to transformation by means of vectors based on agrobacteria (see, inter alia, Chan et al. (1993), Plant Mol. Biol. 22, 491-506).

Alternative systems for transforming monocotyledonous plants or cells thereof are: the transformation by means of the biolostic approach (Wan and Lemaux (1994) Plant Physiol. 104, 37-48; Vasil et al. (1993) Bio/Technology 11, 1553-1558; Ritala et al. (1994) Plant Mol. Biol. 24, 317-325; Spencer et al. (1990), Theor. Appl. Genet. 79, 625-631), the protoplast transformation, the electroporation of partially permeabilized cells, as well as the introduction of DNA via glass fibers.

The transformed cells grow in the usual manner within the plant (see also McCormick et al. (1986), Plant Cell Reports 5, 81-84). The resulting plants can be grown normally and crossed with plants having the same transformed or different hereditary factors. The hybrid individuals resulting therefrom have the corresponding phenotypic properties.

Two or more generations should be grown in order to ensure that the phenotypic characteristic is stably maintained and transmitted. Seeds should also be harvested in order to ensure that the respective phenotype or other characteristics have been maintained.

Likewise, according to conventional methods, transgenic lines can be determined, which are homozygous for the new nucleic acid molecules, and their phenotypic behavior can be examined with respect to a existing or non-existing pathogen responsivity and compared to the behavior of hemizygous lines.

Of course, plant cells containing the nucleic acid molecules according to the present invention can be further cultivated as plant cells (including protoplasts, calli, suspension cultures, and the like).

The vectors illustrated in the above can be transferred to plant cells in different ways. It depends on the respective application, whether the vectors have to be present in linear or circular form. It is known to the person skilled in the art, whether and when he can employ corresponding linearized vectors or not. For instance, it is known to the person skilled in the art that it can be sufficient for producing specific knock-outs of genes for ADFs by means of homologous recombination to linearize the corresponding vectors and to inject them into transgenic plants.

According to the present invention, the term transgenic plant comprises both the plant in its entirety and all plant parts, in which the expression and/or activity of ADFs is altered in accordance with the present invention. Such plant parts can be plant cells, plant seeds, leaves, blossoms, or pollen. According to the present invention, "transgenic plant" is also understood to denote the propagation material of transgenic plants of the present invention, like for example seeds, fruits, cuttings, tubers, rootstocks, etc., wherein said propagation material optionally contains previously described transgenic plant cells, as well as parts of said plants, like protoplasts, plant cells, and calli.

Different methods and possibilities may be considered for producing transgenic plants, as has already been explained in the above. In general, plants or plant cells can be modified with the aid of conventional genetic engineering transformation methods in such a way that the new nucleic acid molecules are integrated into the plant genome, i.e. that stable tranformants are generated and the transferred nucleic acid molecules are replicated with the plant genome. Depending on the used vector system, transgenic plants, in which the nucleic acids to be transferred are contained in the plant cell or in the plant as a self-replicating system, can also be produced according to the present invention. The vectors used for transferring the plants must then correspondingly contain DNA sequences allowing the replication of plasmids used for transfer within the cell.

In principle, any plant can be used for the method according to the present invention. Preferably, it is a monocotyledonous or dicotyledonous useful, food, or fodder plant. Examples for monocotyledonous plants are plants belonging to the genera *Avena* (oat), *Triticum* (wheat), *Secale* (rye), *Hordeum* (barley), *Oryza* (rice), *Panicum, Pennisetum, Setaria, Sorghum* (millet), *Zea* (maize), and the like.

Dicotyledonous useful plants comprise, inter alia, cotton, legumes, like leguminous plants and in particular alfalfa, soy bean, rape, tomato, sugar beet, potato, ornamental plants, and trees. Further useful plants can comprise fruit (in particular apples, pears, cherries, grapes, citrus, pineapple, and bananas), pumpkin, cucumber, wine, oil palms, tea shrubs, cacao trees, and coffee shrubs, tobacco, sisal, as well as, with medicinal plants, rauwolfia and digitalis. Particularly preferred are the cereals wheat, rye, oat, barley, rice, maize and millet, sugar beet, rape, soy, tomato, potato, and tobacco. Further useful plants can be taken from the U.S. Pat. No. 6,137,030.

Preferred plants are cereals, alfalfa, oat, barley, rye, wheat, Triticale, millet, rice, lucerne, flax, cotton, hemp, and Brassicacaea, like for example rape or canola.

Such transgenic plants, their propagation material, as well as their plant cells, plant tissues, or plant parts are a further object of the present invention.

Thus, the present invention also relates to harvest products and propagation material of transgenic plants, which have been produced according to a method of the present invention and have an increased pathogen resistance. The harvest products and the propagation material can be, in particular, fruits, seeds, blossoms, tubers, rootstocks, seedlings, cuttings, etc. They can also be parts of said plants, like plant cells, protoplasts, and calli.

The present invention also relates to the use of the previously mentioned nucleic acid sequences for the production of transgenic plants or plant cells having an increased pathogen resistance in the sense of the present invention.

With the present invention, the identification of ADF3, a further gene involved in the resistance mediated by mlo besides Ror1 and Ror2, in barley was successful for the first time. Moreover, it could be shown within the scope of the present invention, as will be apparent from the Examples illustrated in the following, that resistant barley plants are obtained, which exhibit a non-race-specific resistance to different isolates of the plant pathogen *Blumeria graminis* f. sp. *hordei*, by increasing or reducing the expression or the activity of ADF3 in barley.

As compared to other resistant plants, such transgenic plants have the advantage that they are not only resistant to some specific mildew isolates, but to a multiplicity of the mildew isolates mentioned, and that said resistance is not limited to individual barley cultivars, however.

Thus, a particularly preferred embodiment of the present invention relates to transgenic barley plants or cells having increased resistance to *Blumeria graminis* f. sp. *hordei*, wherein the content and/or the activity of ADF3 from barley having the SEQ ID No. 1 is altered as compared to the wild-type. Particularly preferred embodiments of the present invention also relate to methods for producing transgenic barley plants or the corresponding cells having an increased resistance to *Blumeria graminis* f. sp. *hordei*, wherein the content and/or the activity of ADF3 having the SEQ ID No. 1 is altered as compared to the wild-type. A particularly preferred embodiment of the present invention also relates to the isolated nucleic acid sequence coding for ADF3 from barley having the SEQ ID No. 1 as well as to functionally equivalent parts and functional or non-functional mutants thereof. The same applies to nucleic acid sequences being substantially complementary to the particularly preferred last-mentioned nucleic acid sequences and hybridizing thereto under stringent conditions.

As the Mlo gene so far has been identified in all examined terrestrial plants and thus is also present in organisms other than barley, like for example *Arabidopsis thaliana*, and in other *Gramineae* species, like for example wheat, oat, maize, rye, rice, *Panicum, Pennisetum, Setaria, Sorghum*, Zea, and the like, it can be assumed that the ADF3 from barley functions as prototype for the corresponding homologous ADFs from other plants in the production of transgenic plants or plant cells having an increased pathogen resistance. The respective pathogen resistance can preferably be a resistance to formae speciales of *Blumeria graminis*, as this parasitism also occurs in, for example, wheat, oat, and rye. Moreover, the use of ADFs for producing transgenic plants or plant cells having increased pathogen resistance can also be extended to those pathogens, which have to functionally interact with the actin cytoskeleton in order to establish an efficient infection.

The transgenic plants and plant cells of the present invention can possess a permanent or transient pathogen resistance. The type of resistance depends on the used vectors and the employed selection mechanisms.

Particularly preferred are transgenic plants having an increased pathogen resistance, which are selected from the group containing wheat, barley, oat, rice, *Panicum, Pennisetum, Setaria, Sorghum*, maize (*Zea*), and the like.

Particularly preferably, the previously mentioned plants are resistant to the different formae speciales of the mildew pathogen *Blumeria graminis*, like for example the isolates *Blumeria graminis* f. sp. *hordei, Blumeria graminis* f. sp. *tritici, Blumeria graminis* f. sp. *avenae*.

The identification of ADF3 from barley as a factor mediating a non-race-specific resistance to different isolates of *Blumeria graminis* f. sp. *hordei* will now be illustrated in the following. Furthermore, experiments will be illustrated verifying the use of ADF3 for producing transgenic plants or plant cells having increased resistance to *Blumeria graminis* f. sp.

*hordei*. Said experiments only serve for illustrating the general aspects of the present invention and are by no means to be understood as exclusive.

EXPERIMENTS

1. Identification of ADF3 from Barley

The identification of factors involved in the non-race-specific resistance mechanism in barley mediated by mlo has usually been performed with mutation screening methods (Freialden-hoven et al., vide supra). Herein, barley cultivars containing mlo alleles and being resistant to isolates of *Blumeria graminis* f. sp. *hordei* are assumed. The identification of factors interacting with the Mlo locus is conducted by selection of plants, which subsequent to mutagenesis are sensitive for an infection with isolates of *Blumeria graminis* f. sp. *hordei* despite an mlo genotype. It is the disadvantage of said identification methods that they considerably depend on the sensitivity and the stringency of the screening method for the evidence of a modified infection type. This circumstance as well as the existence of the genetic redundancy of different types of *Gramineae* may be the explanation why further components of the mlo mediated non-race-specific mechanism could hitherto not be identified.

Thus, within the scope of the present invention, a completely different approach was selected for identifying factors influencing the mlo-mediated resistance in barley. To this end, a screening method based on double-stranded RNA interference was conducted, by which genes influencing broad-spectrum resistance, as is mediated by recessive "loss of function" mlo alleles, were supposed to be identified.

With this, a screening method was used within the scope of the present invention, by which it is possible to specifically turn off all alleles of a gene by RNAi. To this end, a cDNA library containing epidermis-specific cDNA from barley was used, which was provided by Dr. Patrick Schweizer (IPK Gatersleben, Germany).

Herein, the production of such an epidermis-specific cDNA library from barley is conducted as follows:

| | |
|---|---|
| Library: | HO |
| Plant: | *Hordeum vulgare* |
| Cultivar: | Ingrid BC mlo5 |
| Tissue: | Epidermis was removed from 7-day-old plants, which had been inoculated with *Blumeria graminis hordei* or *tritici*, 6 and 24 h after inoculation |
| Competent cells: | XL10_Gold by Stratagene |
| Vector: | pBluescript SK+ |
| Insertion sites: | EcoRI (5' end of the cDNA), XhoI (3' end of the cDNA)", |
| Selection of transformed cells: | ampicillin |

The cDNA bank was established by means of a kit by Strategene (pBluescriptII XR cDNA Library Construction Kit, Catalogue No. 200455). The selection of the transformed cells was performed using ampicillin.

The thus isolated cDNA fragments were then cloned into the vector pUAMBN by means of the Gateway® technology by Invitrogen. The use of the Gateway® technology is described in detail in Walhout et al. (Walhout et al. (2000) "GATEWAY recombinational cloning: Application of the cloning of large numbers of open reading frames or ORFeomes", in Applications of Chimeric Genes and Hybrid Proteins, San Diego: ACADEMIC PRESS Inc., pp. 575-592).

The cDNA fragments were amplified by PCR using Gateway®-compatible oligonucleotides with the following sequences:

(SEQ ID NO: 92)
HO-attB-For:
5'-GGG GAC AAG TTT GTA CAA AAA AGC AGG <u>CTG TGG ATC CCC CGG GCT GCA GG</u>-3'

The underlined sequence is specific for the cDNA library.

(SEQ ID NO: 93)
HO-attB-Rev:
5'-GGG GAC CAC TTT GTA CAA GAA AGC TGG <u>GTT AGG GCG AAT TGG GTA CCG GG</u>-3'

The underlined sequence is specific for the cDNA library.

Then, these amplified PCR fragments were inserted into the vector pDONR (Invitrogen) by BP recombination according to the Gateway® technology and were then transferred into the vector pUAMBN by LR recombination according to the Gateway® technology.

In detail, cloning was conducted as follows:
1. Colony PCR (50 µl each in a 96-well plate) from HO library
2. From these PCR reactions, 1 µl each were used in 4 µl BP Gateway reaction:
   1 µl DNA (about 75 ng)
   1 µl vector pDonr201 (about 75 ng)
   1 µl BP reaction buffer
   1 µl BP enzyme
   1 µl H₂O The microtiter plates were incubated for 24 h at room temperature (RT); the complete setups were transformed in 50 µl chemocompetent *E. coli* (DH5α) (1 h at 4° C.; 2 min at 42° C.); the complete transformations were plated on LB-Kan.

3. Then, colonies were picked and grown in microtiter plates and a Millipore 96-well mini preparation was made. The DNA was taken up in 50 µl.
4. 1 µl of the mini preparations was used in 4 µl LR reaction in each case.
   1 µl DNA (about 75 ng)
   1 µl vector pUAMBN (about 75 ng)
   1 µl LR reaction buffer
   1 µl LR enzyme
   1 µl H₂0

The microtiter plates were incubated for 24 h at RT; the complete setups were transformed in 50 µl chemocompetent *E. coli* (DH5α) (1 h at 4° C.; 2 min at 42° C.); the complete transformations were plated on LB-Kan.

5. Then, colonies were picked and grown in microtiter plates and a Millipore 96-well mini preparation was made. The DNA was taken up in 50 µl.

The pUAMBN vector has a polyubiquitin promoter from maize, followed by two Gateway® recombination cassettes in reversed orientation, which are separated by the third intron of the barley Mla1 resistance gene (see FIG. 2).

By means of said arrangement of the vector it is ensured that the PCR amplified fragments are located in sense and antisense direction in the vector. As the same PCR fragment is cloned into the vector once in sense and once in antisense direction, a double-stranded oligo-nucleotide molecule, which is capable of triggering an RNAi response in the plants, is formed after transfection of the vector into the plant cell and after expression of the sequences.

For biolistic transfection, the Particle Delivery System Biolistic® PDS-1000/He (Bio-Rad) was used. The method was performed according to the manufacturer's instructions. To this end, gold particles were coated with the corresponding DNA. For coating the gold particles, 5 µl DNA (1 µg/µl), 50 µl 2.5 M $CaCl_2$ and 20 µl 0.1 M spermidine were typically applied onto previously prepared gold particles. The particles were then pelleted by means of a table centrifuge and washed with 140 µl 70% ethanol and 140 µl 100% ethanol. After another centrifugation step, the coated gold particles were resuspended in 48 to 60 µl 100% ethanol. Subsequently, the epidermal cells were bombarded with the coated particles according to the manufacturer's instructions.

For transfection with the GUS reporter plasmid, the so-called Single-Cell Transient Expression Assay, as described by Shirasu et al., was used (Shirasu et al. (1999), Plant J., 17, 293-299). To this end, the reporter plasmid containing the GUS gene was coated onto gold particles. Coating and bombarding of the leaves was conducted as illustrated above. The bombarded leaves were transferred to 1% agar plates, which were mixed with 8% benzimidazole, and incubated for 4 hours at 18° C. Subsequently, the leaves were stained and microscopically examined for GUS activity.

The GUS construct is described in Nielsen et al. (Nielsen et al. (1999) Physiol. Mol. Plant. Pathol., 54, 1-12).

In experiments, in which the dsRNAi constructs were transfected together with the GUS constructs, the corresponding DNA constructs were mixed prior to coating onto the gold particles. The experiments were then performed correspondingly.

Groups of five double-stranded RNAi (dsRNAi) constructs, each containing one barley gene in form of inverted repeats in the previously described manner in pUAMBN, were transfected into the epidermal cells of individual barley leaves together with a plasmid mediating the constitutive expression of the reporter protein β-glucuronidase (GUS).

Subsequently, the transformed samples were inoculated with *Blumeria graminis* f. sp. *hordei* (Bgh) for 96 hours after ballistic transfection. 48 hours after inoculation, the leaves were stained with respect to GUS activity and individual transformed epidermal cells, which had been inoculated with Bgh spores, were examined microscopically for the penetration success of the fungus. The barley cultivars, which were transfected with the two mentioned vectors, were both the Mlo wild-type and mildew-resistant mlo genotypes as well as genotypes conferring a race-specific resistance to certain mildew isolates (Mla1, Mla6, Mla12, Mlg).

The following barley cultivars were used:
Cultivar Golden Promise (Mlo): Max Planck Institute, Cologne, Germany
Cultivar I10 (Mla12): near isogenic to cv Ingrid
Cultivar BCPallasMla1
Cultivar BCPallasMla6
Cultivar BCPallasMlg
Cultivar BCIngridmlo5
Cultivar BCIngridmlo3
The following mildew isolates were used:
*Blumeria graminis* f. sp. *hordei* K1
*Blumeria graminis* f. sp. *hordei* A6
*Blumeria graminis* f. sp. *tritici* JIW2

In this procedure, a gene, whose expression is silenced by the dsRNAi construct, can then be considered as part of the Mlo non-race-specific resistance mechanism if it effects an increased sensitivity to the Bgh pathogen in the resistant mlo genotype, but does not influence the race-specific resistance in the Mla1-, Mla6-, Mla12-, Mlg-genotypes.

Herein, penetration success is examined microscopically by means of, for example, observing the degree of haustorium formation.

In this manner, the barley gene, which is referred to as ADF3 or HvADF3 in the following, could be identified. Said barley gene had a high amino acid sequence similarity to the already previously described actin-depolymerizing factors from *Arabidopsis thaliana* and *Zea mays*. The ADF3 from barley has the sequence shown in SEQ ID No. 1. A sequence alignment with other ADFs from *Arabidopsis thaliana* is shown in FIG. 1.

The following penetration rates were observed during silencing the expression of ADFs. The data represent average values and standard deviations of three independent experiments:

BCIngridmlo3:         penetration rate 17% ± 1%    control: 0% ± 1%
BCIngridmlo5:         penetration rate 15% ± 3%    control: 0% ± 0%
Golden Promise (Mlo): penetration rate 27% ± 1%    control: 13% ± 1%

2. Interactions of HvADF3 with the Actin Cytoskeleton

An exact examination of the effects of both the overexpression and the silencing of HvADF3 on the cytoskeleton showed that both the overexpression and the silencing lead to an almost complete loss of phalloidine-stainable actin filaments.

For this experiment, epidermal leaf cells from barley were transfected with a plasmid expressing dsRED (RFP) in order to label the transfected cells. In addition in some experiments, a constitutively active variant of HvADF3 bearing an $S^6A$ amino acid substitution rendering the protein inaccessible for N-terminal phosphorylation was expressed. A corresponding mutant was described for ADF3 from maize (Smertenko et al., Plant J 14, 187-193).

For generating the HvADF3-($S^6A$) mutant, a PCR mutagenesis method was utilised:

Primer: HvADF3-CA-F (contains HindIII site and mutation Ser6→Ala6):

(SEQ ID NO: 94)
5'-TTT AAG CTT GCC ACC ATG GCA AAC GCT TCA <u>GCA</u> GGT GCT GGG-3'

Primer: HvADF3-CA-R (contains MluI site):

(SEQ ID NO: 95)
5'-GTT ACG CGT CTA GTG TGC GCG CTC CTT GA-3'

The substitution of serine 6 with alanine 6 was inserted into the wild-type gene of HvADF3 by designing the corresponding primers. The PCR product was cut with the restriction enzymes given in the above and was ligated into the overexpression vector pUbi-MCS-Nos, which had previously been cut with the same restriction enzymes.

Figure 3:
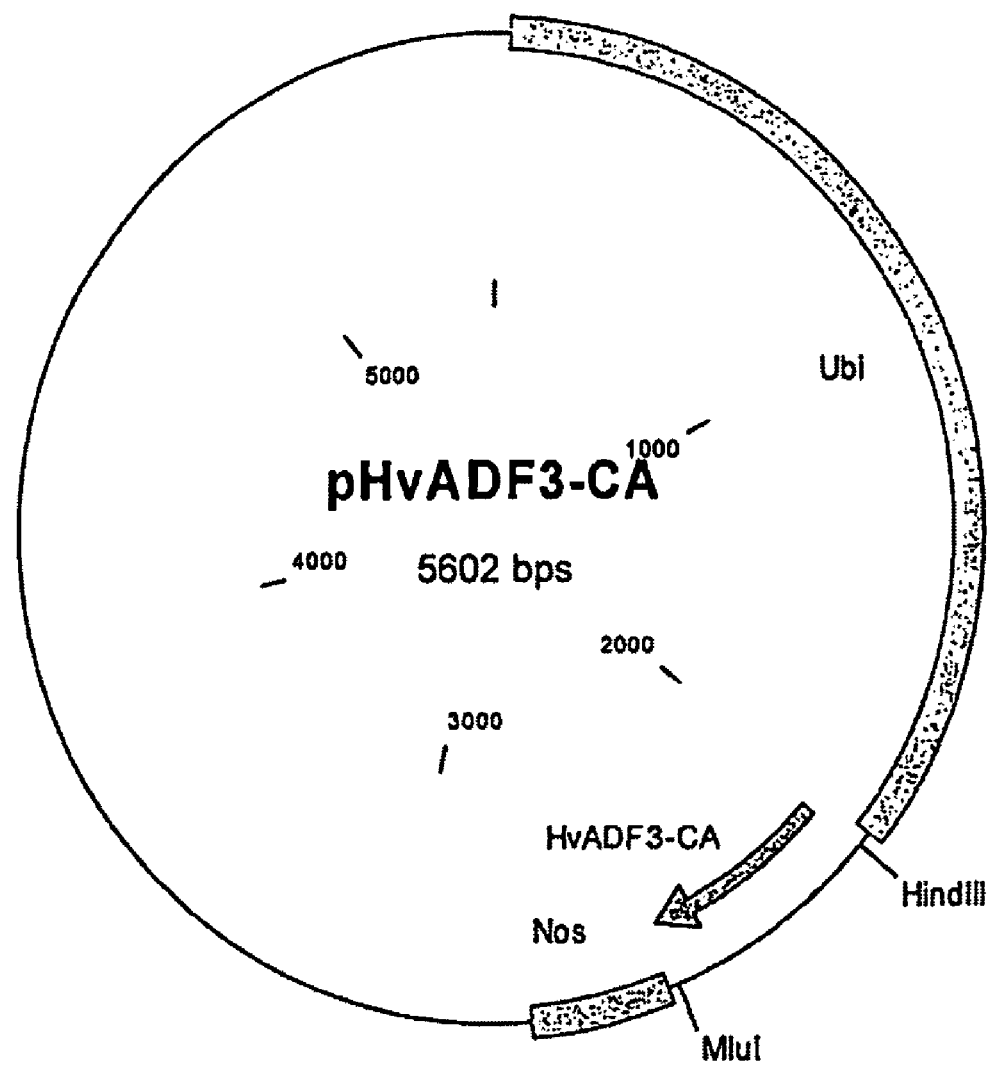
FIG. 3 shows the vector pHvADF3-CA.

The resulting overexpression vector (pHvADF3-CA, FIG. 3) contains a maize polyubiquitin promoter (pUbi), the mutated HvADF3 gene (HvADF3-CA), and a nopaline synthase transcription termination sequence (NOS).

For generating the silencing vectors, the sequence of HvADF3 (SEQ ID No. 45) was amplified with specific Gateway primers and recombined into the vector pUAMBN (see above) via the Gateway technology. The following primers were used:

Primer HvADF3-Gate-F (contains attB1 region):

(SEQ ID NO: 96)
5'-GGG GAC AAG TTT GTA CAA AAA AGC AGG CT GCC ACC ATG GCA AAC GCT TCA TCA GG-3'

Primer HvADF3-Gate-R (contains attB2 region):

(SEQ ID NO: 97)
5'-GGG GAC CAC TTT GTA CAA GAA AGC TGG GTT AGT GTG CGC GCT CCT TGA-3'

HvADF3-specific sequences are underlined.

As described in the above, said vectors were then used for transfecting the plants.

Figure 4:
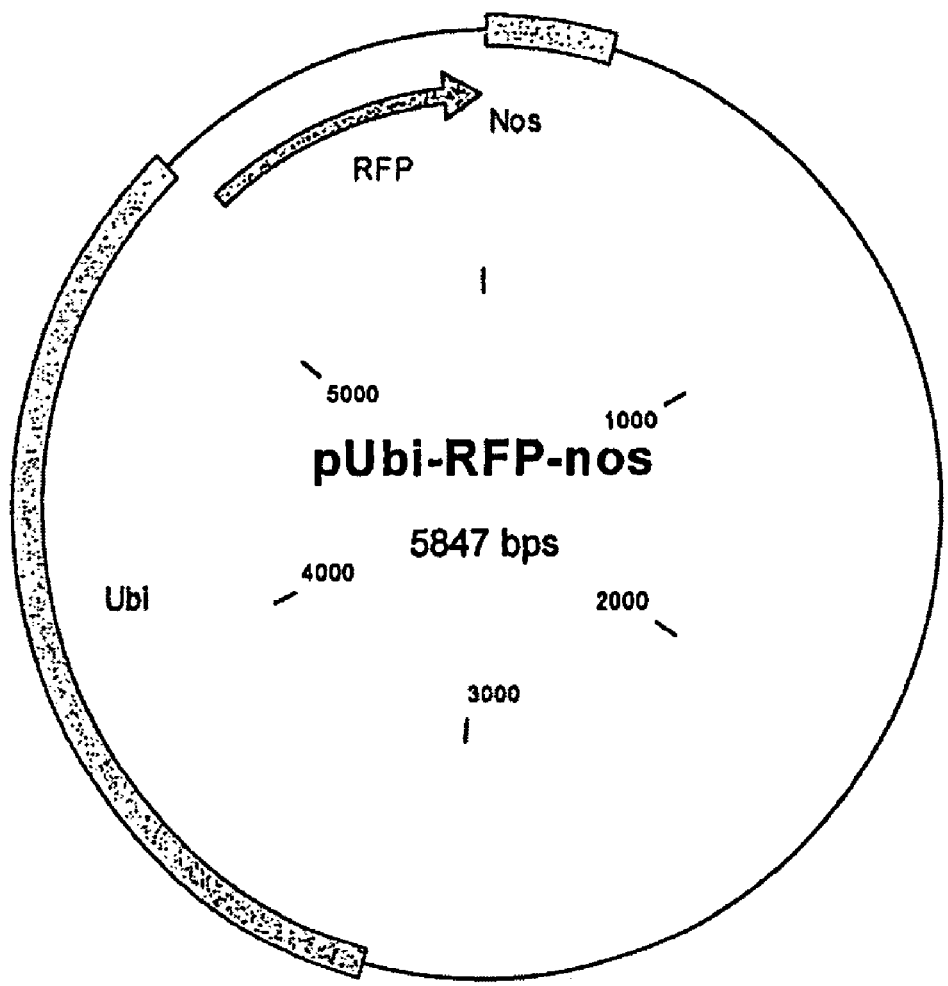
FIG. 4 shows the vector pUbi-RFP-nos.

The dsRED vector (pUbi-RFP-Nos, FIG. 4) has a maize polyubiquitin promoter (pUbi), the coding gene for the red fluorescent protein (*Discosoma* sp. fluorescent protein FP583; RFP), and a nopaline synthase transcription termination sequence (NOS). The GenBank accession number for RFP is AF168419.

The experiments were conducted in BCIngridmlo5.

Figure 5:
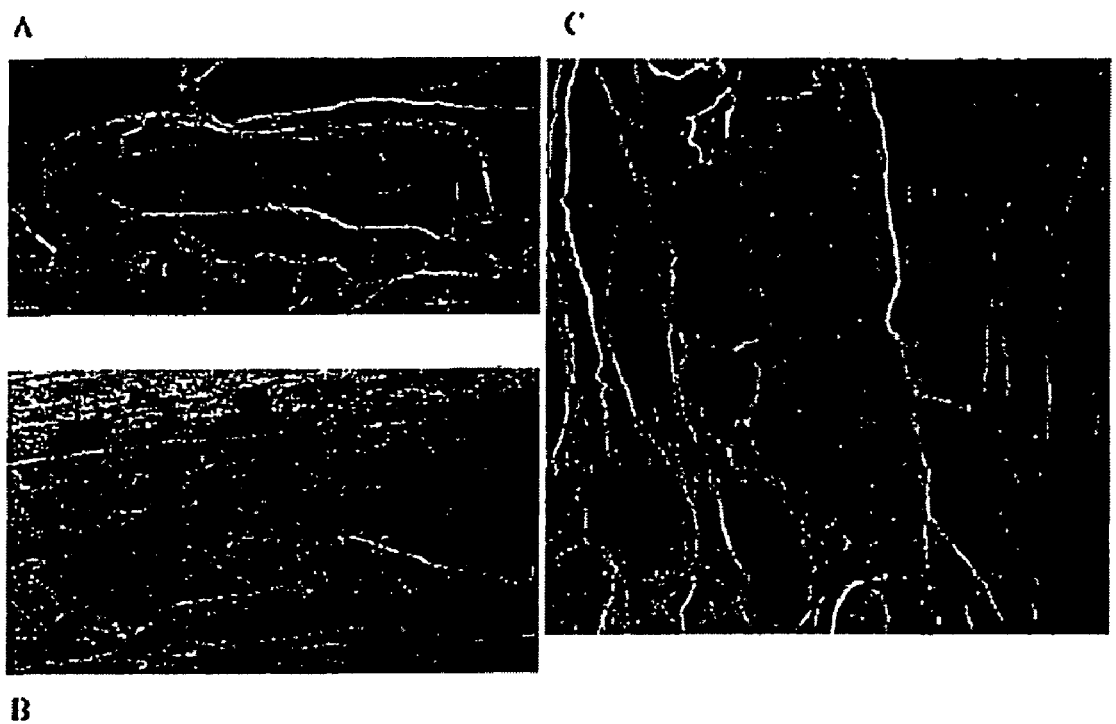
FIG. 5 shows the visualization of the actin cytoskeleton in transfected individual epidermal leaf cells from oat by means of phalloidine staining. The cells were transfected with a plasmid expressing dsRED (RFP) in order to label bombarded cells. In case no additional gene was expressed (control, A), stained actin fibers could be detected within the labeled cells and in neighboring cells. Both in the case of dsRNAi-based silencing of HvADF3 (B) and in the case of overexpression of a constitutively active variant of HvADF3 bearing an $S^6A$ amino acid substitution preventing an N-terminal phosphorylation of the protein (C), actin fibers were only visible in the neighboring cells, but not in the cells labeled with dsRED.

In case no additional HvADF3 (S$^6$A) was expressed, stained actin fibers could be detected both within the bombarded cell and in the neighboring cells (FIG. 5 *a*). However, in case of simultaneous expression of dsRED and HvADF3 (S$^6$A), stainable actin fibers could only be detected in the neighboring cells, but not in the bombarded cells labeled with dsRED, irrespective of whether HvADF3 was silenced (see FIG. 5 *b*) or overexpressed (see FIG. 5*c*).

In order to further examine the HvADF3 function in barley, the effect of the overexpression or the silencing of HvADF3 on the mobility of peroxisomes was examined. Peroxisomes are known to be moved along actin filaments (Mathur (2002) Plant Physiology, Vol. 128, 1031-1045). Herein, barley peroxisomes were visualized by co-transformation of a plasmid expressing a variant of the Green Fluorescent Protein (GFP) with a peroxisomal targeting sequence (Mathur et al., vide supra). Herein, epidermal leaf cells from barley were transfected either only with the GFP construct or together with the already mentioned mutant of HvADF3 (S$^6$A). The expression of said mutant corresponds to an increase of the content and the activity of ADF3.

With the aid of the PCR method, a so-called peroxisome target sequence (PTS) was fused C-terminally to the green fluorescent protein. Said sequence consists of the three amino acids serine (S), arginine (R), and leucine (L) (Jedd, G. et al. (2002) Plant Cell Physiol 43, 384-392).

Primer GFP-F (contains HindIII site and binds in GFP sequence):

(SEQ ID NO: 98)
5'-GCG AAG CTT GCC ACC ATG GTG AGC AAG GGC GAG-3'

Primer GFP-PTS-R (contains additional PTS and MluI site, binds in GFP sequence):

5'-AAG ACG CGT TTA GAG GCG GGA CTT GTA CAG CTC G-3'

The PCR was conducted with a GFP sequence as template.

The PCR product was cut with the restriction enzymes given in the above and was ligated into the overexpression vector pUBI-MCS-Nos, which had previously been cut with the same restriction enzymes.

Figure 6:
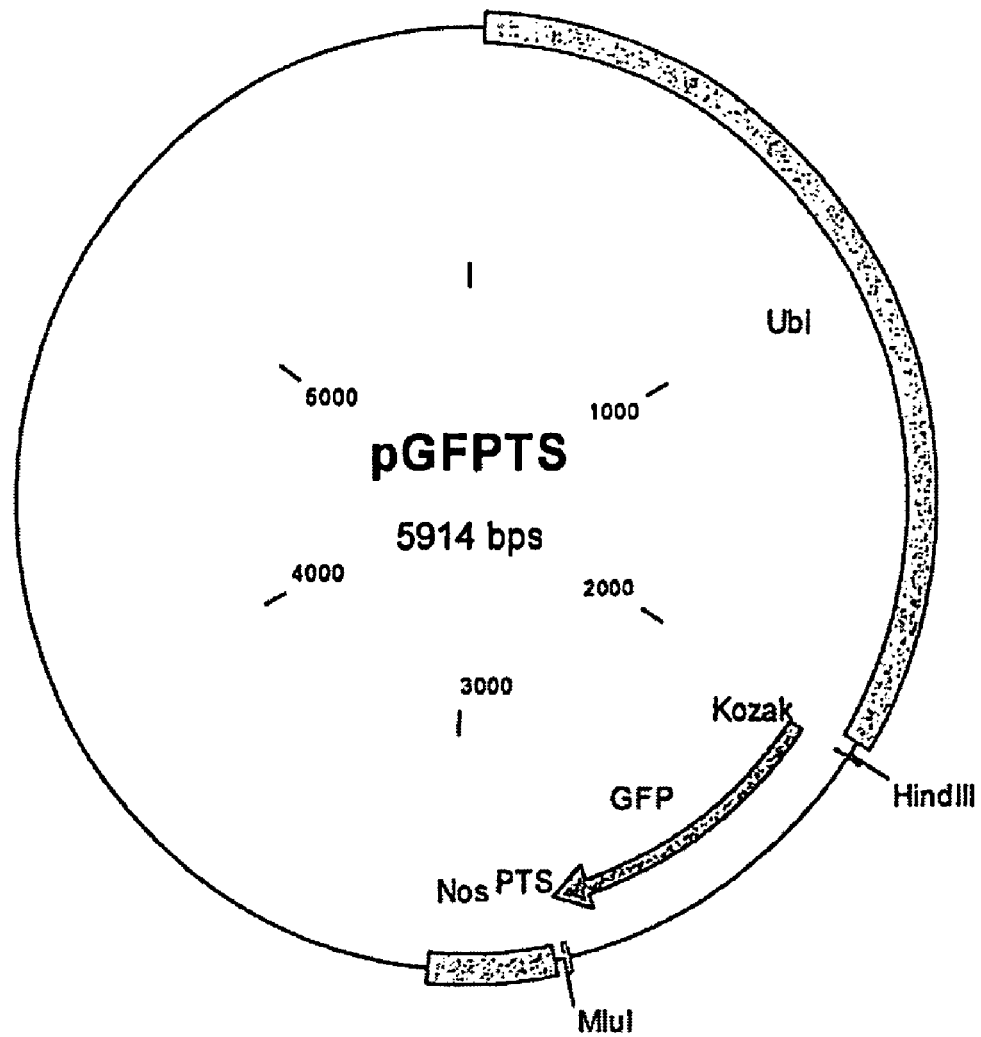
FIG. 6 shows the vector pGFPTS.

The GFP peroxisome target sequence vector (pGFPTS, FIG. 6) has a maize polyubiquitin promoter (pUbi), the coding gene for the green fluorescent protein including the peroxisome target sequence (GFPTS), and a nopaline synthase transcription terminator sequence (NOS).

The overexpression of HvADF3 was performed as described in the above. The silencing experiments were also performed as described in the above.

Overexpressing, but also silencing (data not shown), of HvADF3 caused a drastic reduction or even a total stop of peroxisomal movement and often led to the formation of peroxisomal aggregates (see FIG. 7). While in case of control transfection with GFP alone GFP-labeled peroxisomes constantly move within the bombarded cell (see FIG. 7*a*), the movement of the peroxisomes in case of co-expression of HvADF3 (S$^6$A) is considerably reduced, which finally leads to an aggregation of the peroxisomes (see FIG. 7*b*).

In summary, these results show that the overexpression and also the silencing of HvADF3 results in a loss of phalloidine-stainable actin filaments of the cytoskeleton, which leads to impairment of intracellular, actin filaments mediated transport processes.

3. Resistance of Plants, which are Altered with Respect to the Content or the Activity of HvADF3 as Compared to the Wild-Type The previously described interference of the intracellular transport mechanisms as a result of overexpression or silencing of HvADF3 can have the consequence that transport-dependent defense mechanisms, like, for example, vesicle aggregation at infection sites, can be the reason that, in the experiments leading to the identification of HvADF3, an increased penetration rate in actually resistant mlo genotypes was observed. It was therefore examined whether overexpression or silencing of HvADF3 also leads to a non-race-specific resistance to different Bgh isolates.

Therefore, those cells were examined, which had been transfected with HvADF3 overexpression constructs.

An exact analysis of such transfected cells led to the result that the development of the pathogen at later points in time was either arrested or at least considerably slowed down. While 72 hours after the infection the development of fungal structures in stomata cells, which were located in the vicinity of the transfected cells, appeared to be normal, the fungal structures of spores, which attacked the transfected cells, were only weakly developed. Here, it has to be observed that stomata cells retain a remaining sensitivity for mildew infection also in mlo genotypes.

For said experiments, epidermal leaf cells from barley were co-transfected with a plasmid for the GUS reporter together with a plasmid coding for HvADF3($S^6A$), as was described in the above. Four hours after bombardment, the leaves were infected with Bgh conidia, and 22 hours after inoculation the leaves were stained with respect to GUS activity and fungal structures. FIGS. 8*a* and *b* show the fungal development in a transfected epidermal leaf cell. FIG. 8*c* shows the fungal development in a stomata cell. The expression of HvADF3($S^6A$) corresponds to an overexpression of HvADF3. The experiments were performed in BCIngridmlo5 plants.

As can be seen from the FIGS. 8a, b, and c, the fungus can only form very short hyphae in cells, in which HvADF3 is overexpressed, which prevents the establishment of an effective infection. In contrast, the fungal structures in stomata cells, which have not been transfected, are fully developed (see FIG. 8c). It thus appears that, while in case of a successful penetration of the cell wall the fungal pathogen at first benefits from the impaired actin cytoskeleton of the host, it cannot, however, establish a successful infection as intact actin filaments are apparently necessary for maintaining a compatible interaction. Therefore, a non-race-specific resistance to different Bgh isolates can be achieved by increasing or reducing the content and/or the activity of ADF3 in barley.

The previously described experiments are all based on a transient expression by particle bombardment. The result thus obtained can easily be transferred to stably transformed transgenic plants, in which the expression of ADFs is increased or reduced permanently. Stably transformed plants can, for example, be produced as is described in the following.

The nucleic acid sequence for ADF3 from *Arabidopsis thaliana*, which is given in SEQ ID No. 11, can be amplified via the following primers:

```
Fra224      atggctaatgcagcatcagg

Fra 255     tcaattggctcggcttttga
```

Figure 9:
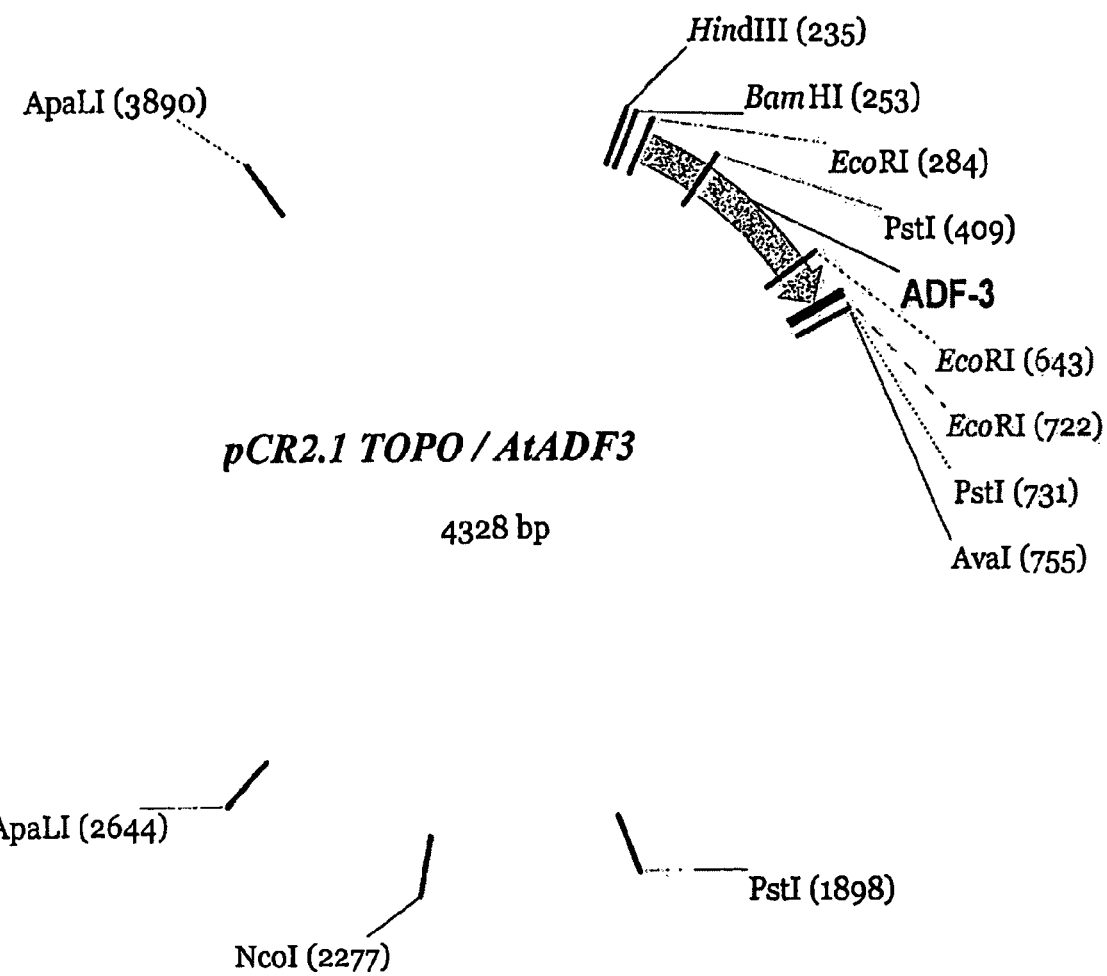
FIG. 9 shows the vector pCR2.1 TOPO with inserted AtADF3 gene.

For transformation, the obtained fragment is cloned into a binary vector. Beforehand, subcloning into the vector pCR®2.1 TOPO (Invitrogen, Karlsruhe, Germany) is performed, from which the gene can be recleaved via the enzymes EcoRV and HindIII (see FIG. 9). The overhanging ends are filled in with Klenow enzyme.

Figure 10:
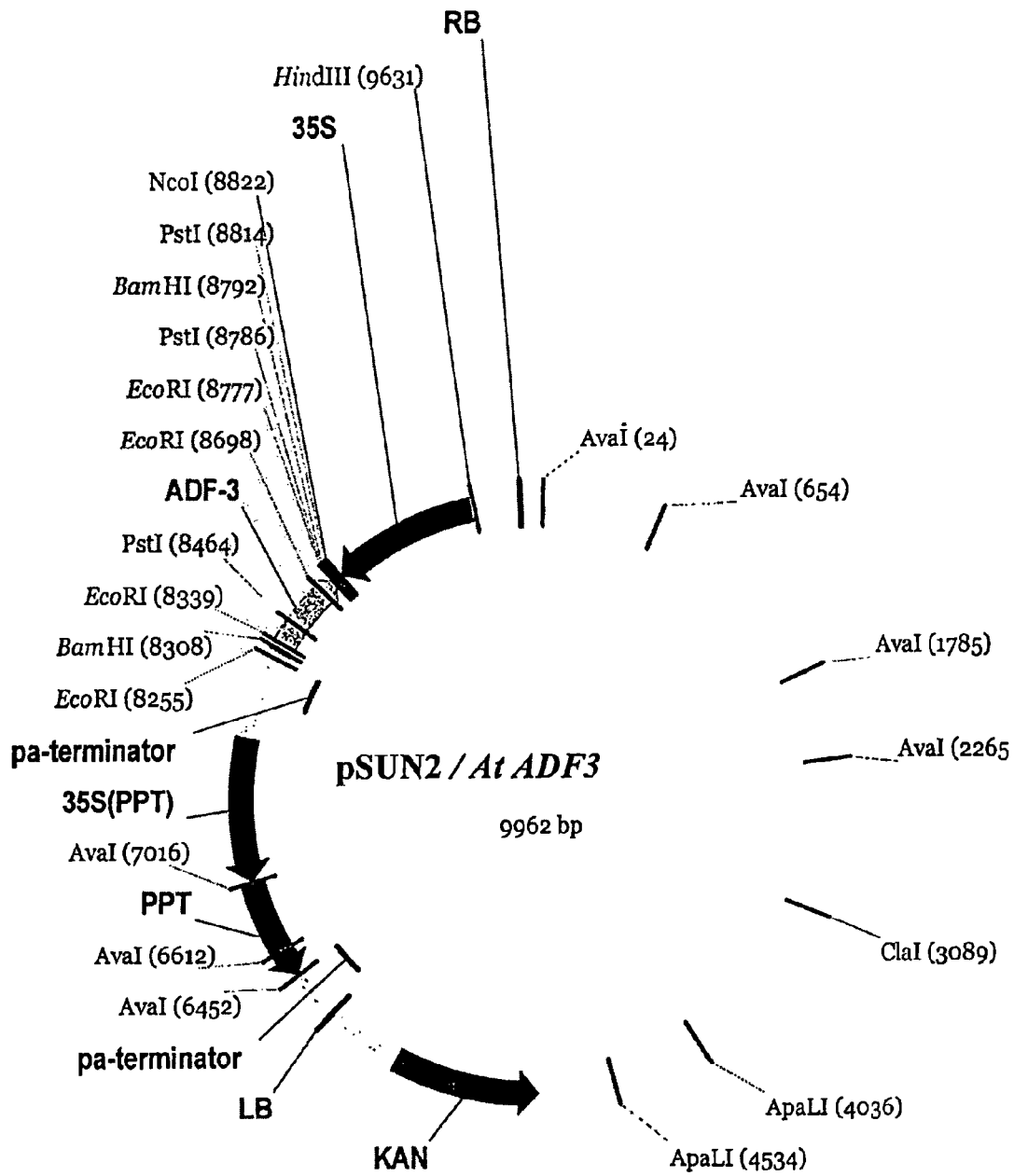
FIG. 10 shows the vector pSUN2 with inserted AtADF3 gene.

For constitutive expression of AtADF3, the fragment generated in the above is ligated into the dephosphorylated binary vector pSUN2, which has been opened with SmaI (see FIG. 10).

Figure 11:
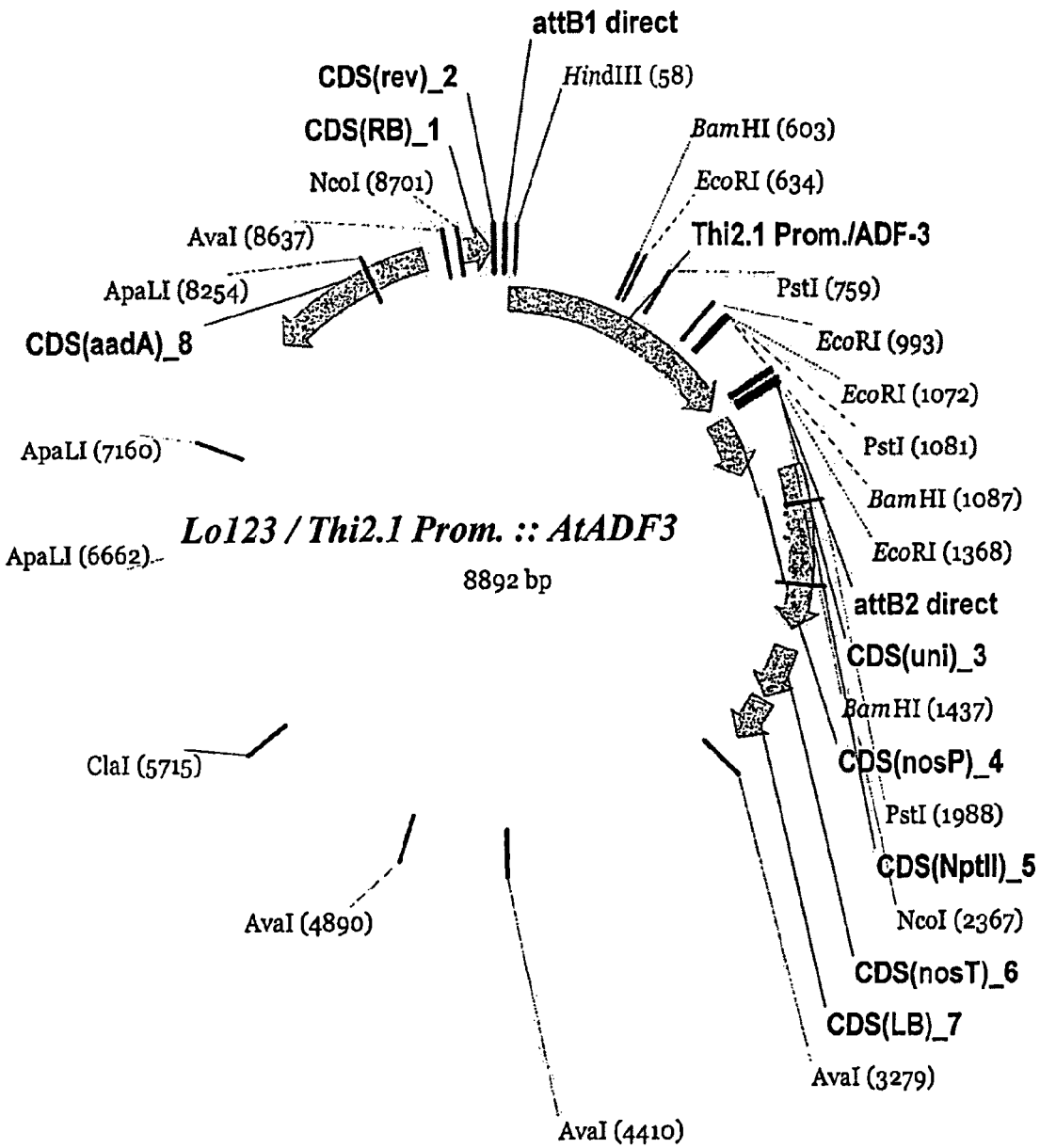
FIG. 11 shows the vector Lo123 with inserted AtADF3 gene.

In order to also allow the pathogen-inducible expression of AtADF3, the latter is cut out from pSUN2 with BglII and XbaI and ligated into the vector Lo215. This vector already contains the Thi2.1 promoter from *Arabidopsis thaliana* (Acc. No. L41244; Epple, P., Apel, K. and Bohlmann, H. (1995) An *Arabidopsis thaliana* thionine gene is inducible via a signal transduction pathway different from that for pathogenesis-related proteins, Plant Physiol. 109 (3), 813-820), which is induced by pathogen infection, which has already been shown via a downstream GUS gene. AtADF3 is cloned into the site of the GUS gene by cutting out the latter from the vector using SacI and SmaI, dephosphorylating and filling in the vector, and ligating the AtADF3 fragment into the vector. Via a homologous recombination (Gateway® reaction, Invitrogen, Karlsruhe, Germany), the promoter/gene construct was then subcloned into the binary vector Lo123 (see FIG. 11).

The transformation is conducted according to the floral dip method (modified according to Clough and Bent, 1998). After being harvested, the seeds are sterilized with chlorine gas overnight and subsequently laid out on selection plates. The addition of antibiotics is conducted in dependency on the plant resistance marker. In case of pSUN2, BASTA is added; in case of Lo123, kanamycin is added. After sterilization, the seeds are laid out on the selection plates and are stored for stratification for two days at 4° C. in a cooling chamber. Subsequently, they are further observed under short-day conditions. After about 10 days, the first selection of the plants can be performed. Non-transgenic plants will lose color during selection, while transgenic plants having the corresponding resistance gene remain green. Those plants remaining green after the first selection are selected a second time under same conditions. Those plants still maintaining their color during the second selection can then be transferred to soil. The plants are selfed and the resulting T2 seed populations are subjected to phytopathological analysis.

For analyzing the resistance of the transgenic *Arabidopsis thaliana* plants against pathogenic fungi, inoculations with the biotrophic oomycetes or fungi *Peronospora parasitica* and *Erysiphe cichoracearum* are performed.

a) Infection with *Peronospora parasitica*

5 to 8-week-old plants are sprayed with a conidia spore suspension (about $10^6$ spores/ml). The inoculated plants are covered with a plastic bag and kept dark and moist overnight in a cooling chamber at about 16° C. After one day, the plastic bag is slightly opened and later on entirely removed. Six days after inoculation, the plants are once again covered with the plastic bag overnight, which induces sporulation. On the following day, the leaves are examined for the occurrence of conidiophores. Over the following days, the intercellular growth of the fungus leads to the induction of weak chloroses to strong necroses in the leaves. These symptoms are quantified and tested for significance.

b) Infection with *Erysiphe cichoracearum*

The biotrophic mildew fungus is cultivated on *Arabidopsis thaliana* plants. For infecting the 4-week-old transgenic *Arabidopsis* plants, conidiophores are taken from the surface of the leaves by means of a fine brush and are applied onto the leaves of the transgenic plants. The plants are incubated for 7 days at 20° C. 7 days after inoculation, the conidiophores (conidia carriers) on the leaves will become visible and chloroses and necroses will emerge over the following days. These symptoms are quantified and tested for significance.

c) Results

The transgenic *Arabidopsis* plants expressing AtADF3 constitutively or pathogen-inducibly exhibit a significantly increased resistance to both *Peronospora parasitica* and to *Erysiphe cichoracearum*, as compared to the non-transgenic wild-type plants.

The invention claimed is:

1. A method for the production of a transgenic plant or a plant cell with increased pathogen resistance, comprising introducing into the plant or plant cell a double stranded RNAi construct comprising a sense sequence and an anti-sense sequence that is complementary to the sense sequence, the sense sequence has at least 80% sequence identity to SEQ ID NO:45, wherein the content and/or the activity of at least one endogenous actin-depolymerising factor (ADF) in the transgenic plant or plant cell is decreased as compared to a wild-type plant or plant cell.

2. The method according to claim 1, wherein the at least one endogenous ADF is an ADF which has the consensus sequences identified in SEQ ID NO: 89, 90 and/or 91.

3. The method according to claim 1, wherein the construct further comprises a promoter and a terminal sequence functional in plants.

4. A method for the production of a transgenic plant with increased pathogen resistance, comprising the following steps:
- a) producing a vector comprising the following nucleic acid sequences in 5' to 3' orientation: a promoter sequence functional in plants, operatively linked thereto an anti-sense sequence with from 20 to 300 contiguous bases of SEQ ID NO: 45, and sense sequence that is complementary to the antisense sequence to form dsRNA, wherein the sense and antisense sequences are identical or homologous to a part of at least one endogenous actin-depolymerising factor (ADF), operatively linked thereto a termination sequence functional in plants;
- b) transferring the vector to plant cells to produce transformed plant cells; and
- c) producing a transgenic plant from the transformed plant cells.

5. The method according to claim 3, wherein the vector contains further regulatory and functional sequences in addition to promoter and termination sequences.

6. The method according to claim 5, wherein the regulatory sequences are enhancers, replication signals, selection markers and/or sequences, which allow propagation of the vectors in bacteria and/or a transient and/or permanent replication in plant cells.

7. The method according to claim 3, wherein the vector is a plasmid, cosmid and/or recombinant virus.

8. The method according to claim 7, wherein the vector is pBR322, a pUC vector, M13mp vector or a vector which is derived from the Ti or Ri plasmid of Agrobacteria.

9. The method according to claim 3, wherein the promoter sequence is a constitutive promoter, a tissue-specific promoter, a leaf-specific promoter, a development-specific promoter, a light-inducible promoter, a wound-inducible or pathogen-inducible promoter.

10. The method according to claim 3, wherein the vector is transferred to the plants by transformation, transfection, injection, biolistic methods and/or electroporation.

11. The method according to claim 1, wherein the transgenic plant or plant cell shows an increased resistance to pathogens selected from the group consisting of *Blumeria graminis* f. sp. *hordei, tritici, avenae, secalis, lycopersici, vitis, cucumis, cucurbitae, pisi, pruni, solani, rosae, fragariae, rhododendri, mali* and *nicotianae*.

12. The method according to claim 11, wherein the plant or plant cell shows increased resistance to *Blumeria graminis* f. sp. *hordei*.

13. The method according to claim 1, wherein the transgenic plant is a monocotyledonous plant.

14. The method according to claim 13, wherein the transgenic plant is barley or wheat.

15. The method according to claim 1, wherein the transgenic plant is a dicotyledonous plant.

16. The method of claim 13, wherein the monocotyledonous plant belongs to the genus *Avena* (oat), *Triticum* (wheat), *Secale* (rye), *Hordeum* (barley), *Oryza* (rice), *Panicum, Pennisetum, Setaria, Sorghum* (millet), or *Zea* (maize).

17. The method of claim 1, wherein the at least one endogenous ADF is identified in SEQ ID NO: 1.

18. A transgenic plant or plant cell with increased pathogen resistance, comprising a double stranded RNAi construct comprising a sense sequence and an antisense sequence that is complementary to the sense sequence, wherein the sense sequence has at least 80% sequence identity to SEQ ID NO:45, wherein the content and/or activity of at least one endogenous actin-depolymerising factor (ADF) is altered compared to a wild-type plant or plant cell.

19. The transgenic plant or plant cell according to claim 18, wherein the at least one ADF is an ADF having the consensus sequences identified in SEQ ID NO: 89, 90 and/or 91.

20. The transgenic plant or plant cell according to claim 18, wherein the endogenous ADF has at least 80% sequence identity to SEQ ID NO: 1.

21. The transgenic plant or plant cell according to claim 18, wherein the transgenic plant or plant cell shows an increased resistance to pathogens selected from the group consisting of *Blumeria graminis* f. sp. *hordei, tritici, avenae, secalis, lycopersici, vitis, cucumis, cucurbitae, pisi, pruni, solani, rosae, fragariae, rhododendri, mali* and *nicotianae*.

22. The transgenic plant or plant cell according to claim 18, wherein the transgenic plant is a monocotyledonous plant.

23. The transgenic plant or plant cell according to claim 18, wherein the at least one ADF, the content and/or activity of which is altered compared to the wild-type plant or plant cell, is ADF3 from barley, and wherein the plant is barley and the pathogen, against which the plant is resistant, is *Blumeria graminis* f. sp. *hordei*.

24. A transgenic plant cell or plant with increased pathogen resistance, produced by the method according to claim 1.

25. An isolated nucleic acid comprising a nucleic acid molecule selected from the group consisting of:
- a) a nucleic acid molecule coding for the actin-depolymerising factor 3 (ADF3) of SEQ ID NO: 1, and
- b) a nucleic acid molecule coding for an ADF polypeptide which is at least 80% identical to SEQ ID NO: 1.

26. The isolated nucleic acid molecule according to claim 25, wherein the nucleic acid molecule comprises the sequence as set forth in SEQ ID NO: 45 or 46.

27. An expression vector, comprising:
a promoter sequence functional in plants,
operatively linked thereto the nucleic acid according to claim 25,
operatively linked thereto a termination sequence functional in plants.

28. The method of claim 1, wherein the at least one endogenous ADF has at least 80% sequence identity to SEQ ID NO: 1.

29. The method of claim 4, wherein the at least one endogenous ADF has at least 80% sequence identity to SEQ ID NO: 1.

* * * * *